(12) United States Patent
Cutting et al.

(10) Patent No.: US 12,171,734 B2
(45) Date of Patent: Dec. 24, 2024

(54) PATHOGENIC BACTERIA

(71) Applicant: Sporegen Limited, London (GB)

(72) Inventors: Simon Cutting, London (GB); Hong Huynh, London (GB)

(73) Assignee: Sporegen Limited, London (GB)

( * ) Notice: Subject to any disclaimer, the term of this patent is extended or adjusted under 35 U.S.C. 154(b) by 280 days.

(21) Appl. No.: 16/970,708

(22) PCT Filed: Feb. 15, 2019

(86) PCT No.: PCT/GB2019/050409
§ 371 (c)(1),
(2) Date: Aug. 18, 2020

(87) PCT Pub. No.: WO2019/162652
PCT Pub. Date: Aug. 29, 2019

(65) Prior Publication Data
US 2020/0375931 A1    Dec. 3, 2020

(30) Foreign Application Priority Data
Feb. 20, 2018  (GB) ..................... 1802720

(51) Int. Cl.
| | |
|---|---|
| A61K 31/195 | (2006.01) |
| A23L 33/10 | (2016.01) |
| A61K 9/107 | (2006.01) |
| A61K 38/12 | (2006.01) |
| A61P 31/04 | (2006.01) |

(52) U.S. Cl.
CPC .......... *A61K 31/195* (2013.01); *A23L 33/127* (2016.08); *A61K 9/107* (2013.01); *A61K 38/12* (2013.01); *A61P 31/04* (2018.01); *A23V 2002/00* (2013.01)

(58) Field of Classification Search
None
See application file for complete search history.

(56) References Cited

U.S. PATENT DOCUMENTS

| | | |
|---|---|---|
| 2009/0274673 A1 | 11/2009 | Eskandarian |
| 2015/0147303 A1 | 5/2015 | Hsieh |

FOREIGN PATENT DOCUMENTS

| | | |
|---|---|---|
| WO | 2014085576 | 5/2014 |

OTHER PUBLICATIONS

Arguelles-Arias et al. (Microbial Cell Factories 2009, 8:63).*
Fracchia et al. (Biosurfactants and Bioemulsifiers Biomedical and Related Applications Present Status and Future Potentials (2012)).*
Boottanun et al. (AMB Expr (2017) 7:16).*
Chapter 4 of Cryopreservation and Freeze-Drying Protocols (2007); ed. by John G. Day and Glyn N. Stacey.*
Hindler, Janet A., et al., "Methods for Antimicrobial Dilution and Disk Susceptibility Testing of Infrequently Isolated or Fastidious Bacteria", Clinical and Laboratory Standards Institute, Oct. 2015, M45, 3rd ed.
Lau, Jennifer T., et al., "Capturing the diversity of the human gut microbiota through culture-enriched molecular profiling", Genome Medicine (2016) 8:72.
Lawley, Trevor D., et al., "Targeted Restoration of the Intestinal Microbiota with a Simple, Defined Bacteriotherapy Resolves Relapsing Clostridium difficile Disease in Mice", PLOS Pathogens, Oct. 2012, vol. 8, Issue 10.
Lee, Na-Ri, et al., "In vitro evaluation of new functional properties of poly-γ-glutamic acid produced by Bacillus subtilis D7", Saudi Journal of Biological Sciences (2014), 21, 153-158.
Lessa, Fernanda C., et al., "Current Status of Clostridium difficile Infection Epidemiology", Clinical Infectious Diseases (2012);55(S2):S65-70.
Lessa, Fernanda C., et al., "Burden of Clostridum difficile Infection in the United States", The New England Journal of Medicine, Feb. 26, 2015, 372;9, 825-834.
Liu, Jun, et al., "γ-Polyglutamic acid (γ-PGA) produced by Bacillus amyloliquefaciens C06 promoting its colonization on fruit surface", International Journal of Food Micobiology 42 (2010), 190-197.
Lopez-Serrano, Pilar, et al., "Environmental risk factors in inflammatory bowel diseases. Investigating the hygiene hypothesis: A Spanish case-control study", Scandinavian Journal of Gastroenterology, 2010; 45: 1464-1471.
Ma, Zongwang, et al., "Isolation and characterization of a new iturinic lipopeptide, mojavensin A produced by a marine-derived bacterium Bacillus mojavensis B0621A", The Journal of Antibiotics, 2012, 65: 317-322.
Makovitzki, Arik, et al., "Antimicrobial Lipopolypeptides Composed of Palmitoyl Di- and Tricationic Peptides: In Vitro and in Vivo Activities, Self-Assembly to Nanostructures, and a Plausible Mode of Action", American Chemical Society: Biochemistry, 2008, 47, 10630-10636.
Malick, Afshan, et al., "Production of exopolysaccharides by selected Bacillus strains: Optimization of media composition to maximize the yield and structural characterization", International Journal of Biological Macromolecules, 2017.

(Continued)

*Primary Examiner* — Patricia Duffy
*Assistant Examiner* — Garen Gotfredson
(74) *Attorney, Agent, or Firm* — FisherBroyles LLP; Adam K. Whiting; Adelaide K. Leitzel

(57) ABSTRACT

The present invention relates to pathogenic bacteria, and is particularly concerned with treating, preventing or ameliorating bacterial infections using novel antibiotic compositions. The invention is especially useful for treating infections of *Bacillus* and Clostridia species, such as *Clostridium difficile, Staphylococcus aureus* and *Mycobacterium* spp. The invention extends to pharmaceutical compositions comprising such formulations. The invention also extends to methods for identifying aerobic *Bacillus* spp., which exhibit antibacterial activity against other bacteria, such as *C. difficile*, and to methods for isolating active antibacterial compositions from these aerobic *Bacillus* spp.

36 Claims, 37 Drawing Sheets
Specification includes a Sequence Listing.

(56) References Cited

OTHER PUBLICATIONS

Marteyn, Benoit, et al., "Breathing life into pathogens: the influence of oxygen on bacterial virulence and host responses in the gastrointestinal tract", Cellular Microbiology (2011), 13(2), 171-176.
Meena, Khem Raj, et al., "Lipopeptides as the Antifungal and Antibacterial Agents: Applications in Food Safety and Therapeutics", Bio Med Research International, 2014, vol. 2015, Article ID 473050, 9 pgs.
Ines, Mnif, et al., "Lipopeptides Biosurfactants, Main Classes and New Insights for Industrial; Biomedical and Environmental Applications", Biopolymers: Peptide Science, 2015, 57 pgs.
Nakano, Michiko M., et al., "Anaerobic Growth of a "Strict Aerobe" (Bacillus Subtilis)", Annual Review of Microbiology, 998; vol. 52: 165-190.
Harwood, Colin R., et al., "Molecular Biological Methods for Bacillus", Modern Microbiological Methods, 1990.
Nicholson, W.L., "Roles of Bacillus endospores in the environment", Cellular and Molecular Life Sciences, 59 (2002) 410-419.
Nielsen, H. Bjorn, et al., "Identification and assembly of genomes and genetic elements in complex metagenomic samples without using reference genomes", Nature Biotechnology, 2014, 11 pgs.
Orenstein, Robert, et al., "Saftey and Durability of RBX2660 (Mirobiota Suspension) for Recurrent Clostridium difficile Infection: Results of the PUNCH CD Study", Clinical Infectious Diseases, 2016:62 (Mar. 1).
Orsod, Mohamed, et al., "Characterization of Expolysaccharides Produced by Bacillus cereus and *Brachybacterium* sp. Isolated from Asia Sea Bass (*Lates calcarifer*)", Malaysian Journal of Microbiology, vol. 8(3) 2012, pp. 170-174.
O'Toole, George, et al., "Biofilm Formation as Microbial Development", Annual Reviews Microbiology, 2000, 54:49-79.
Ott, Stephan, J., et al., "Efficacy of Sterile Fecal Filtrate Transfer for Treating Patients With Clostridium difficile Infection", Gastroenterology 2017; 152:799-811.
Permpoonpattana, Patima, et al., "Immunization with Bacillus Spores Expressing Toxin A Peptide Repeats Protects against Infection with Clostridium difficile Strains Producing Toxins A and B", American Society for Microbiology—Infection and Immunity, Jun. 2011, vol. 79, No. 6, pp. 2295-2302.
Petrof, Elaine O., et al., "From Stool Transplants to Next-generation Microbiota Therapeutics", Gastroenterology (2014), doi: 10.1053/j.gastro.2014.01.004.
Phetcharaburanin, Jutarop, et al., "The spore-associated protein BclA1 affects the susceptibility of animals to colonization and infection by Clostridium difficile", Molecular Microbiology (2014) 92(5), 1025-1038.
Phister, Trevor G., et al., "Identification of Bacilysin, Chlorotetaine, and Iturin A Produced by *Bacillus* sp. Stran CS93 Isolated from Pozol, a Mexican Fermented Maize Dough", Applied and Environmental Microbiology, Jan. 2004, vol. 70, No. 1, pp. 631-634.
Popiolski, Tatiane M., et al., "Preparation of Polymeric Micelles of Poly(Ethylene Oxide-b-Lactic Acid) and their Encapsulation With Lavender Oil", Materials Research, 2016; 19(6): 1356-1365.
Qin, Junjie, et al., "A human gut microbial gene catalogue established by metagenomic sequencing", Nature, vol. 464, Mar. 4, 2010, pp. 59-67.
Razafindralambo, H., et al., "Surface-Active Properties of Surfactin/Iturin A Mixtures Produced by Bacillus subtilis", American Chemical Society, 1997, vol. 13, No. 23;6026-6031.
Sambol, Susan P., et al., "Infection of Hamsters with Epidemiologically Important Strains of Clostridium difficile", The Journal of Infectious Diseases, 2001; 183:1760-1766.
Smith, C. Jeff, et al., "Transferable Tetracycline Resistance in Clostridium difficile", Antimicrobial Agents and Chemotherapy, Jun. 1981, vol. 19, No. 6, pp. 997-1003.
Smits, L.P., et al., "Therapeutic Potential of Fecal Microbiota Transplantation", Gastroenterology (2013), doi: 10.1053/i.gastro.2013.08.058.
Stein, Torsten, "Bacillus subtilis antibiotics: structures, syntheses and specific functions", Molecular Microbiology (2005) 56(4), 845-857.
Strachan, David P., "Hay fever, hygiene, and household size", BMJ, vol. 299, Nov. 18, 1989, pp. 1259-1260.
Tam, Nguyen K.M., et al., "The Intestinal Life Cycle of Bacillus subtilis and Close Relatives", Journal of Bacteriology, Apr. 2006, vol. 188, No. 7, pp. 2692-2700.
Tvede, M., et al., "Rectal bacteriotherapy for recurrent Clostridium difficile-associated diarrhoea: results from a case series of 55 patients in Denmark 2000-2012", Clincial Microbiology and Infection, 2014:1-6.
Vater, J., "Lipopeptides, an attractive class of microbial surfactants", Progress in Colloid & Polymer Science, 72:12-18 (1986).
Wust, Jurg, et al., "Investigation of an Outbreak of Antibiotic-Associated Colitis by Various Typing Methods", Journal of Clinical Microbiology, Dec. 1982, vol. 16, No. 6, pp. 1096-1101.
Xu, Zhihui, et al., "Contribution of Bacillomycin D in Bacillus amyloliquefaciens SQR9 to Antifungal Activity and Biofilm Formation", Applied and Environmental Microbiology, Feb. 2013, vol. 79, No. 3, pp. 808-815.
Yoshida, S., et al., "Antimicrobial Activity of Culture Filtrate of Bacillus amyloliquefaciens RC-2 Isolated from Mulberry Leaves", The American Phytopathological Society—Biological Control, 2001, vol. 91, No. 2, pp. 181-187.
Youssef, Noha H., et al., "Comparison of methods to detect biosurfactant production by diverse microorganisms", Journal of Microbiological Methods 2004, (56), pp. 339-347.
Zhao, Xin, et al., "Identification and classification of known and putative antimicrobial compounds produced by a wide variety of *Bacillales* species", BioMed Central Genomics, (2016) 17:882, 18 pgs.
Zhi, Yan, et al., "Genome and transcriptome analysis of surfactin biosynthesis in Bacillus amyloliquegfaciens MT45", Scientific Reports, Jan. 23, 2017, 7:40976, 13 pgs.
Abriouel, Hikmate, et al., "Diversity and applications of Bacillus bacteriocins", Federation of European Microbiological Societies, Rev 35 (2011) 201-232.
Alou, Maryam Tidjani, et al., "Bacillus mediterraneensis", a new bacterial species isolated from the human gut microbiota, New Microbes and New Infections (2016), doi: 10.1016/j.nmni.2016.05.006.
Ayed, Hanen Ben, et al., "Isolation and biochemical characteristion of a bacteriocin-like substance produced by Bacillus amyloliquefaciens An6", Journal of Global Antimicrobial Resistance, Feb. 4, 2015.
Ayukekbong, James A., et al., "The threat of antimicrobial resistance in developing countries: causes and control strategies", Antimicrobial Resistance and Infection Control (2017) 6:47.
Baranova, Ekaterina, et al., "SbsB structure and lattice reconstruction unveil Ca2+ triggered S-layer assembly", Structural and Molecular Microbiology (2012).
Bauer, MP, "Clostridium difficile infection in Europe: a hospital-based survey", Center for Infectious Disease Control Netherlands, Bilthoven; et al., Lancvet 377:63-73, 2011.
Bechet, Max, et al., "Structure, biosynthesis, and properties of kurstakins, nonribosomal lipopeptides from *Bacillus* spp.", Appl Microbiol Biotechnol (2012) 95:593-600.
Bloomfield, Sally F., et al., "Time to abandon the hygiene hypothesis: new perspectives on allergic disease, the human microbiome, infectious disease prevention and the role of targeted hygiene", Perspectives in Public Health, Jul. 2016, vol. 136, No. 4.
Browne, Hilary P., et al., "Culturning of 'unculturable' human microbiota reveals novel taxa and extensive sporulation", Host-Microbiota Interactions Laboratory, et al., 2016.
Burke, Kristin E., et al., "Clostridium difficile Infection: A Worldwide Disease", Gut and Liver, vol. 8, No. 1, Jan. 2014, pp. 1-6.
Cartman, Stephen T., et al., "Bacillus subtilis Spores Germinate in the Chicken Gastrointestinal Tract", Applied and Environmental Microbilogy, Aug. 2008, vol. 74, No. 16, p. 5254-5258.
Casula, Gabriella, et al., "Bavillus Probiotics: Spore Germination in the Gastrointestinal Tract", Applied Environmental Microbiology, May 2002, vol. 68, No. 5, p. 2344-2352.

(56) References Cited

OTHER PUBLICATIONS

Chun, Jongsik, et al., "Phylogenetic analysis of Bacillus subtilis and related taxa based on partial gyrA gene sequences", Antonie van Leeuwenhoek 78: 123-127, 2000.

Colenutt, Clair, et al., "Use of Bacillus subtilis PXN21 spores for suppression of Clostridium difficile infection symptoms in a murine model", Federation of European Microbilogical Societies, Mar. 2014, p. 1-8.

Collins, Deirdre A., et al., "Epidemiology of Clostridium difficile infection in Asia", Antimicrobial Resistance & Infection Control, 2013, 2:21, p. 1-9.

Costello, S.P., et al., "Faecal microbiota transplant for recurrent Clostridium difficile infection using long-term frozen stool is effective: clinical efficacy and bacterial viability data", AP&T Alimentary Pharmacology and Terapeutics, 2015; 42: 1011-1018.

Cui, Xiaohong, et al., "Mechanism of Surfactant Micelle Formation", American Chemical Society, Jun. 2008, 24, 10771-10775.

Deleu, Magali, et al., "Effect of Fengycin, a Lipopeptide Produced by Bacillus subtilis, on Model Biomembranes", Biophysical Journal, vol. 94, Apr. 2008, 2667-2679.

Depestel, Daryl D., et al., "Epidemiology of Clostridium difficile Infection", Journal of Pharmacy Practice, 2013, 26 (5), 464-475.

Drekonja, Dimitri, et al., "Fecal Microbiota Transplantation for Clostridium difficile Infection", Annals of Internal Medicine, vol. 162, No. 9, May 5, 2015.

Duitman, Erwin H., et al., "The mycosubtilin synthetase of Bavillus subtilis ATCC6633: A multifunctional hybrid between a peptide synthetase, an amino transferase, and a fatty acid synthase", PNAS, Nov. 9, 1999, vol. 96, No. 23, 13294-13299.

European Food Safety Authority, "Guidance on the assessment of bacterial susceptibility to antimicrobials of human and veterinary importance", EFSA Journal, 2012; 10(6):2740.

Ege, Markus J., et al., "Exposure to Environmental Microorganisms and Childhood Asthma", The New England Journal of Medicine, Feb. 2011, vol. 364, No. 8, 701-709.

Fagan, Robert P., et al., "Biogenesis and functions of bacterial S-layers", Nature Reviews—Microbiology, Mar. 2014, vol. 12, 211-222.

Fakhry, S., et al., "Characterization of spore forming Bacilli isolated from human gastrointestinal tract", The Society for Applied Microbiology, Journal of Applied Microbiology 105, Jul. 2008, 2178-2186.

Geeraerts, Sofie, et al., "Bacillus amyloliquefaciens as prophylactic treatment for Clostridium difficile associated disease in a mouse model", Department of Pathology, et al., 2015, 1-23.

Gerding, Dale N., "Clindamycin, Cephalosporins, Fluoroquinolones, and Clostridium difficile—Associated Diarrhea: This is an Antimicrobial Resistance Problem", Clinical Infectious Diseases, Mar. 2004, vol. 38, 646-648.

Ghelardi, E., et al., "Survival and persistence of Bacillus clausii in the human gastrointestinal tract following oral administration as spore-based probiotic formulation", Journal of Applied Microbilogy 119, 2015, 552-559.

Gough, Ethan, et al., "Systematic Review of Intestinal Microbiota Transplantation (Fecal Bacteriotherapy) for Recurrent Clostridium difficile Infection", Clinical Infectious Diseases, Nov. 2011, 53(10), 994-1002.

Gu, Shenghua, et al., "Bacterial Community Mapping of the Mouse Gastrointestinal Tract", PLOS One, Oct. 2013, vol. 8, Issue 10.

Gupta, Arjun, et al., "Community-acquired Clostridium difficile infection: an increasing public health threat", Infection and Drug Resistance, Mar. 2014, 63-72.

Hong, Huynh A., et al., "The use of bacterial spore formers as probiotics", FEMS Microbiology Reviews 29, 2005, 813-835.

Hong, Huynh A., et al., "Bacillus subtilis isolated from the human gastrointestinal tract", Research in Microbiology 160, 2009, 134-143.

Hong, Huynh A., et al., "Defining the natural habitat of Bacillus spore-formers", Research of Microbiology 160, 2009, 375-379.

Hong, Huynh A., et al., "Mucosal Antibodies to the C-terminus of Toxin A Prevent Colonization of Clostridium difficile", American Society for Microbiology, Feb. 2017.

Hong, Huynh A., et al., "The Spore Coat Protein CotE Facilitates Host Colonization by Clostridium difficile", The Journal of Infectious Diseases, Dec. 2017, 216, 1452-1459.

Horn, Joshua N., et al., "Characterization of a potent antimicrobial lipopeptide via coarse-grained molecular dynamics", Biochimica et Biophysica Acta 1818, 2012, 212-218.

Horn, Joshua N., et al., "Simulating the Mechanism of Antimicrobial Lipopeptides with All-Atom Molecular Dynamics", American Chemical Society, 2013, 52, 560-5610.

Illinskaya, Olga N., et al., "Secretome of Intestinal Bacilli: A Natural Guard against Pathologies", Frontiers in Microbiology, Sep. 2017, vol. 8, Article 1666.

Inbaraj, B. Stephen, et al., "Thy synthesis and characterization of poly (y-glutamic acid)-coated magnetite nanoparticles and their effects on antibacterial activity and cytotoxicity", Nanotechnology (22), 2011.

International Search Report and Written Opinion of PCT/GB2019/050409, mailed May 23, 2019.

Isa, Mohd Hafz Mohd, et al., "Recovery and purification of surfactin from fermentation broth by a two-step ultrafiltration process", Journal of Membrane Science (296), 2007, 51-57.

Jauregi, Paula, et al., "Micelle size characterization of lipopeptides produced by B. subtilis and their recovery by the two-step ultrafiltration process", Separation and Purification Technology (104), 2013, 175-182.

Kelly, Denise, et al., "Importance of microbial colonization of the gut in early life to the development of immunity", Mutation Research (622), Feb. 2007, 58-69.

Khoruts, Alexander, et al., "Understanding the mechanisms of faecal microbiota transplantation", Nature Reviews—Gastroenterology & Hepatology, Jun. 2016.

Kim, P.I., et al., "Purification and characterization of a lipopeptide produced by Bacillus thuringiensis CMB26", Journal of Applied Microbiology, Mar. 2004, 97, 942-949.

Klich, Maren A., et al., "Iturin A: potential new fungicide for stored grains", Mycopathologia (127), 1994, 123-127.

Lagier, Jean-Christophe, et al., "Microbial culturomics: paradigm shift in the human gut microbiome study", Clinical Microbiology and Infection, vol. 18, No. 12, Dec. 2012, 1185-1193.

Lagier, Jean-Christophe, et al., "The Rebirth of Culture in Microbiology through the Example of Culturomics to Study Human Gut Microbiota", Clinical Microbiology Reviews, Jan. 2015, vol. 28, No. 1.

Ferreira, William T., et al. "Micellar antibiotics of bacillus." Pharmaceutics 13.8 (2021): 1296.

\* cited by examiner

A

B

A

B

SEQUENCE LISTING

```
<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: Iturin A
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Asn
<220> FEATURE:
<221> NAME/KEY: MISC_FEATURE
<222> LOCATION: (6)..(6)
<223> OTHER INFORMATION: D-Asn
```

```
<400> SEQUENCE: 1

Asn Xaa Xaa Gln Pro Xaa Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Iturin AL
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Asn
<220> FEATURE:
<221> NAME/KEY: MISC_FEATURE
<222> LOCATION: (6)..(6)
<223> OTHER INFORMATION: D-Asn

<400> SEQUENCE: 2

Asn Xaa Xaa Gln Pro Xaa Ser
1               5

<210> SEQ ID NO 3
<211> LENGTH: 7
<212> TYPE: PRT
<213> ORGANISM: Artificial Sequence
<220> FEATURE:
<223> OTHER INFORMATION: Iturin C
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Asn
<220> FEATURE:
<221> NAME/KEY: MISC_FEATURE
<222> LOCATION: (6)..(6)
<223> OTHER INFORMATION: D-Asn

<400> SEQUENCE: 3

Asn Xaa Xaa Gln Pro Xaa Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Mycosubtilin
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Asn
<220> FEATURE:
<221> NAME/KEY: MISC_FEATURE
<222> LOCATION: (6)..(6)
<223> OTHER INFORMATION: D-Ser

<400> SEQUENCE: 4

Asn Xaa Xaa Gln Pro Xaa Asn
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Bacillomycin D
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Asn
<220> FEATURE:
<221> NAME/KEY: MISC_FEATURE
<222> LOCATION: (6)..(6)
<223> OTHER INFORMATION: D-Ser

<400> SEQUENCE: 5

Asn Xaa Xaa Pro Glu Xaa Thr
1               5

<210> SEQ ID NO 6
<211> LENGTH: 7
<212> TYPE: PRT
<213> ORGANISM: Artificial Sequence
<220> FEATURE:
<223> OTHER INFORMATION: Bacillomycin F
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Asn
<220> FEATURE:
<221> NAME/KEY: MISC_FEATURE
<222> LOCATION: (6)..(6)
<223> OTHER INFORMATION: D-Asn

<400> SEQUENCE: 6

Asn Xaa Xaa Gln Pro Xaa Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Bacillomycin L
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Asn
<220> FEATURE:
<221> NAME/KEY: MISC_FEATURE
<222> LOCATION: (6)..(6)
<223> OTHER INFORMATION: D-Asn

<400> SEQUENCE: 7

Asn Xaa Xaa Ser Gln Xaa Thr
1               5

<210> SEQ ID NO 8
<211> LENGTH: 7
```

```
<212> TYPE: PRT
<213> ORGANISM: Artificial Sequence
<220> FEATURE:
<223> OTHER INFORMATION: Bacillomycin LC
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Asn
<220> FEATURE:
<221> NAME/KEY: MISC_FEATURE
<222> LOCATION: (6)..(6)
<223> OTHER INFORMATION: D-Ser

<400> SEQUENCE: 8

Asn Xaa Xaa Ser Gln Xaa Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Esperin
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (6)..(6)
<223> OTHER INFORMATION: D-Leu

<400> SEQUENCE: 9

Glu Leu Xaa Val Asp Xaa Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Lichenysin
<220> FEATURE:
<221> NAME/KEY: MISC_FEATURE
<222> LOCATION: (1)..(1)
<223> OTHER INFORMATION: Glu or Gln
<220> FEATURE:
<221> NAME/KEY: MISC_FEATURE
<222> LOCATION: (2)..(2)
<223> OTHER INFORMATION: Leu or Ile
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: Val or Ile
<220> FEATURE:
<221> NAME/KEY: MISC_FEATURE
<222> LOCATION: (6)..(6)
<223> OTHER INFORMATION: D-Leu
<220> FEATURE:
<221> NAME/KEY: MISC_FEATURE
<222> LOCATION: (7)..(7)
<223> OTHER INFORMATION: Val or Ile

<400> SEQUENCE: 10

Xaa Xaa Xaa Xaa Asp Xaa Xaa
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: Pumilacidin
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (6)..(6)
<223> OTHER INFORMATION: D-Leu
<220> FEATURE:
<221> NAME/KEY: MISC_FEATURE
<222> LOCATION: (7)..(7)
<223> OTHER INFORMATION: Val or Ile

<400> SEQUENCE: 11

Glu Leu Xaa Leu Asp Xaa Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Surfactin
<220> FEATURE:
<221> NAME/KEY: MISC_FEATURE
<222> LOCATION: (2)..(2)
<223> OTHER INFORMATION: Val, Leu or Ile
<220> FEATURE:
<221> NAME/KEY: MISC_FEATURE
<222> LOCATION: (3)..(3)
<223> OTHER INFORMATION: D-leu
<220> FEATURE:
<221> NAME/KEY: MISC_FEATURE
<222> LOCATION: (4)..(4)
<223> OTHER INFORMATION: Ala, Val, Leu or Ile
<220> FEATURE:
<221> NAME/KEY: MISC_FEATURE
<222> LOCATION: (6)..(6)
<223> OTHER INFORMATION: D-Leu
<220> FEATURE:
<221> NAME/KEY: MISC_FEATURE
<222> LOCATION: (7)..(7)
<223> OTHER INFORMATION: Val, Leu or Ile

<400> SEQUENCE: 12

Glu Xaa Xaa Xaa Asp Xaa Xaa
1               5

<210> SEQ ID NO 13
<211> LENGTH: 10
<212> TYPE: PRT
<213> ORGANISM: Artificial Sequence
<220> FEATURE:
<223> OTHER INFORMATION: Fengycin A
<220> FEATURE:
<221> NAME/KEY: MISC_FEATURE
<222> LOCATION: (2)..(2)
<223> OTHER INFORMATION: Orn
<220> FEATURE:
<221> NAME/KEY: MISC_FEATURE
<222> LOCATION: (3)..(3)
<223> OTHER INFORMATION: D-Tyr
<220> FEATURE:
<221> NAME/KEY: MISC_FEATURE
<222> LOCATION: (4)..(4)
<223> OTHER INFORMATION: aThr
<220> FEATURE:
```

```
<221> NAME/KEY: MISC_FEATURE
<222> LOCATION: (6)..(6)
<223> OTHER INFORMATION: D-Ala
<220> FEATURE:
<221> NAME/KEY: MISC_FEATURE
<222> LOCATION: (9)..(9)
<223> OTHER INFORMATION: D-Ala

<400> SEQUENCE: 13

Glu Xaa Xaa Xaa Glu Xaa Pro Gln Thr Ile
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Fengycin B
<220> FEATURE:
<221> NAME/KEY: MISC_FEATURE
<222> LOCATION: (2)..(2)
<223> OTHER INFORMATION: D-Orn
<220> FEATURE:
<221> NAME/KEY: MISC_FEATURE
<222> LOCATION: (3)..(3)
<223> OTHER INFORMATION: D-Tyr
<220> FEATURE:
<221> NAME/KEY: MISC_FEATURE
<222> LOCATION: (4)..(4)
<223> OTHER INFORMATION: D-aThr
<220> FEATURE:
<221> NAME/KEY: MISC_FEATURE
<222> LOCATION: (6)..(6)
<223> OTHER INFORMATION: D-Val

<400> SEQUENCE: 14

Glu Xaa Xaa Xaa Glu Xaa Pro Gln Thr Ile
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Plipastatin A
<220> FEATURE:
<221> NAME/KEY: MISC_FEATURE
<222> LOCATION: (2)..(2)
<223> OTHER INFORMATION: D-Orn
<220> FEATURE:
<221> NAME/KEY: MISC_FEATURE
<222> LOCATION: (4)..(4)
<223> OTHER INFORMATION: D-aThr
<220> FEATURE:
<221> NAME/KEY: MISC_FEATURE
<222> LOCATION: (6)..(6)
<223> OTHER INFORMATION: D-Ala
<220> FEATURE:
<221> NAME/KEY: MISC_FEATURE
<222> LOCATION: (9)..(9)
<223> OTHER INFORMATION: D-Tyr

<400> SEQUENCE: 15

Glu Xaa Thr Xaa Glu Xaa Pro Gln Xaa Ile
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Plipastatin B
<220> FEATURE:
```

```
<221> NAME/KEY: MISC_FEATURE
<222> LOCATION: (2)..(2)
<223> OTHER INFORMATION: D-Orn
<220> FEATURE:
<221> NAME/KEY: MISC_FEATURE
<222> LOCATION: (4)..(4)
<223> OTHER INFORMATION: D-aThr
<220> FEATURE:
<221> NAME/KEY: MISC_FEATURE
<222> LOCATION: (6)..(6)
<223> OTHER INFORMATION: D-Ala
<220> FEATURE:
<221> NAME/KEY: MISC_FEATURE
<222> LOCATION: (9)..(9)
<223> OTHER INFORMATION: D-Tyr

<400> SEQUENCE: 16

Glu Xaa Thr Xaa Glu Xaa Pro Gln Xaa Ile
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Bacillopeptin
<220> FEATURE:
<221> NAME/KEY: MISC_FEATURE
<222> LOCATION: (1)..(1)
<223> OTHER INFORMATION: D-Asn
<220> FEATURE:
<221> NAME/KEY: MISC_FEATURE
<222> LOCATION: (4)..(4)
<223> OTHER INFORMATION: D-Ser
<220> FEATURE:
<221> NAME/KEY: MISC_FEATURE
<222> LOCATION: (6)..(6)
<223> OTHER INFORMATION: Beta amino acid
<220> FEATURE:
<221> NAME/KEY: MISC_FEATURE
<222> LOCATION: (8)..(8)
<223> OTHER INFORMATION: D-Tyr

<400> SEQUENCE: 17

Xaa Ser Glu Xaa Thr Xaa Asn Xaa
1               5
```

PATHOGENIC BACTERIA

The present invention relates to pathogenic bacteria, and is particularly concerned with treating, preventing or ameliorating bacterial infections using novel antibiotic formulations. The invention is especially useful for treating infections of *Bacillus* and Clostridia species, such as *Clostridium difficile, Staphylococcus aureus* and *Mycobacterium* spp. The invention extends to pharmaceutical compositions comprising such formulations. The invention also extends to methods for identifying aerobic *Bacillus* spp., which exhibit antibacterial activity against other bacteria, such as *C. difficile*, and to methods for isolating active antibacterial compositions from these aerobic *Bacillus* spp.

*C. difficile* infection (CDI) is a nosocomial infection mainly affecting the elderly and the young. However, studies have shown an increasing rate of CDI in young people and healthy individuals without a history of antibiotic use (i). Clindamycin resistance has historically been one of the largest contributing factors in the development of CDI in humans and animals (2). CDI rates are higher in developed countries, such as the US and UK, although antibiotics are more heavily used in developing countries. Perhaps, the distribution of hyper-virulent strains and variations in diets and hygiene contribute to this difference in rates of CDI.

Faecal microbiota transplantation (FMT) has been shown to be highly effective in the treatment of recurrent CDI. A single treatment has reliably been shown to resolve 85-90% of cases while two treatments, up to 100% (3-6). The scientific rationale for FMT is based on two assumptions, either that patients with dysbiosis have lost their healthy microbiota, or that the microbiota is unable to retain its normal functionality. Traditional FMT techniques aim to transfer a stable, viable and diverse microbial community contained in stool preparations from healthy donors. The therapeutically active agent(s) could comprise bacteria, components of faecal water (e.g., the virome) or potentially products of the donor's human cells (7).

Due to the potential long-term safety concerns of FMT (8, 9), there has been a shift to the use of defined mixtures of bacteria (i.e., bacteriotherapy) that have been derived from donor faeces. In a seminal study using mice, cocktails of intestinal bacteria were isolated from the faeces of healthy animals that suppressed CDI in infected mice (10). Interestingly, the intestinal microbiota of treated animals was shown to shift towards that of healthy animals with an increased bacterial diversity. The six species included obligate and facultative anaerobic species representing three of the four predominantly intestinal microbiota phyla (*Staphylococcus warneri, Enterococcus hirae, Lactobacillus reuteri, Anaerostipes* sp. Nov., *Bacteroidetes* sp. Nov, and *Enterorhabdus* sp. nov.). In this study, autoclaved faeces, faecal filtrates and individual strains failed to suppress infection leading to the conclusion that these bacteria displaced the *C. difficile* population by competition. However, FMT has not yet been shown to be effective when used as a primary CDI treatment without the use of antibiotics in conjunction.

The study described above together with others using defined or mixed populations of faecal bacteria (11, 12) suggest competitive exclusion as the mechanism for suppression of CDI and that the active agents emanate from the bacterial fraction. Therefore, it is possible that the activity might arise from one or more components derived from the bacteria. For example, antimicrobial compounds or metabolites produced by the transplanted bacteria or bacteriophages integrated into the bacterial genome (prophages), which are subsequently activated and released following transfer to the patient. With FMT, stool water together with bacteria is transferred to the patient and this fraction is itself rich in bacterial debris, proteins, antimicrobial compounds, metabolic products and oligonucleotides/DNA. Using just the faecal filtrate, symptoms of CDI were abolished in five patients exhibiting chronic-relapsing infection following nasojejunal transfer of the sterile filtrate (7). Symptoms were eliminated for 6 months post-transfer confirming that the sterile stool water could abolish relapsing CDI. The active agent present in faecal water has remained elusive and no protein candidate was identified. Two explanations were proposed, first, fragments of the bacterial cell wall or DNA that might stimulate (via pattern recognition receptors) the host immune system to facilitate growth of beneficial bacteria. Second, through the transfer of bacteriophage virions or induction of temperate bacteriophages, that directly or indirectly, suppress growth of *C. difficile*.

The human microbiota contains anywhere from 100-1000 bacteria species with considerable diversity between individuals (13,14). This population is dominated by strict anaerobes, and so an important question has been how they transfer between individuals. This can now be partly explained by the remarkable finding that about 60% of genera found in the human GI-tract are spore-forming bacteria representing 30% of the total intestinal microbiota (15). In this study, spore-forming bacteria isolated from human faeces were cultured anaerobically and then identified using analysis of the 16S rRNA. Clearly, spores (endospores) have the ability to survive outside of the host indefinitely and so are well-suited for transfer to other humans.

The present invention arises from the inventors' work in attempting to overcome the problems associated with the prior art.

There are two types of spore forming bacteria, aerobic and anaerobic species. Since the GI-tract is considered anoxic, it has been long assumed that anaerobic bacteria predominate and are therefore likely to be more important than the aerobic counterparts. As described herein, the inventors have appreciated that aerobic spore forming bacteria are present in the GI-tract of humans and animals, and that they are acquired from the environment and therefore form a so-called 'allochthonous' population. The aerobic community of spore formers is mostly *Bacillus* species. These aerobic spore formers are mostly unnoticed using microbiome-based methods for bacterial detection, because they often exist as spores, and thus are refractory to extraction methods. Instead, they are best detected using culture-based methods. The inventors have therefore shown that it is in fact the aerobic cohort that is important, and not the anaerobic cohort, with regard to *C. difficile* infection (CDI). It is known that certain antibiotics kill aerobic *Bacillus* (as well as other bacteria), and, as described in the Examples, the antibiotic, clindamycin, is used, as it is particularly relevant to CDI. The use of clindamycin, therefore, provides an opportunity for CD spores to germinate and outgrow, that is to say, a niche is provided. The inventors have shown that some *Bacillus* species produce large amounts of a novel antibacterial composition, (AmyCide® or AmyCidin™), which exhibits biosurfactant and/or antimicrobial activity, and is surprisingly able to lyse not only *C. difficile*, but also other bacteria of medical or veterinary importance (e.g., those that infect animals, such as shrimp).

Hence, in a first aspect of the invention, there is provided a live or dead spore, or a live or dead vegetative cell of *Bacillus amyloliquefaciens* and/or *Bacillus subtilis*, or extracellular material produced by the live cell, or disrupted cell homogenate, for use in treating, preventing or ameliorating a bacterial infection.

Advantageously, the inventors have shown that these bacteria can be used prophylactically and therapeutically. Surprisingly, and preferably, the use of allochthonous bacteria (rather than anaerobic, autochthonous bacteria) can be used to effectively combat bacterial infections.

In one embodiment, it is preferred that a live spore of *B. amyloliquefaciens* and/or *Bacillus subtilis*, is used to combat the bacterial infection. In another embodiment, it is preferred that a dead spore of *B. amyloliquefaciens* and/or *B. subtilis*, is used. In yet another embodiment, a dead cell of *B. amyloliquefaciens* and/or *B. subtilis*, is used to combat the bacterial infection. The skilled person will appreciate that there are several ways in which the bacterial spore or cell may be killed or rendered non-viable, such as irradiation (e.g., Gamma radiation), or heating (e.g., pasteurisation). The dead cell may comprise a broken or a disrupted cell, i.e., one that has been mechanically or physically disrupted by, for example, sonication or an enzyme, such as lysozyme etc. In this embodiment, the disrupted cell's integuments and exopolysaccharides (EPS) etc. would exhibit the antibacterial activity. Hence, in a further embodiment, it is preferred that the disrupted cell homogenate of *B. amyloliquefaciens* and/or *B. subtilis* cells, is used. However, in a most preferred embodiment, a live vegetative cell of *B. amyloliquefaciens* and/or *B. subtilis*, or extracellular material produced by the live cell, is used to combat the infection. As described in the Examples, the inventors have shown that the supernatant extract (which does not include vegetative cells or spores, i.e., a cell-free sample) surprisingly exhibits antibacterial activity. Thus, in another preferred embodiment, a cell-free sample (e.g., the supernatant) comprising extracellular material produced by the live vegetative cell or disrupted cell homogenate may be used to combat the bacterial infection.

Preferably, the *B. amyloliquefaciens* strain that is used is selected from a group consisting of: SG18, SG57, SG137, SG136, SG185, SG277 and SG297. Most preferably, the *B. amyloliquefaciens* strain is SG277 or SG297.

Preferably, the *B. subtilis* strain is selected from a group consisting of SG17, SG83 and SG140. Most preferably, the *B. subtilis* strain is SG140.

In one embodiment, one or more strains of *B. amyloliquefaciens*, or extracellular material produced by the cell or disrupted cell homogenate, is used. In other words, any *B. amyloliquefaciens* strain selected from a group consisting of: SG18, SG57, SG137, SG136, SG185, SG277 and SG297, may be used. Alternatively, in another embodiment, more than one *B. amyloliquefaciens* strain selected from a group consisting of: SG18, SG57, SG137, SG136, SG185, SG277 and SG297, may be used. For example, SG277 and SG297 could be used simultaneously, or SG18 and SG57 could be used simultaneously, and so on.

In another embodiment, one or more strains of *B. subtilis*, or extracellular material produced by the cell or disrupted cell homogenate, is used. In other words, any *B. subtilis* strain selected from a group consisting of: SG17, SG83 and SG140, may be used. Alternatively, in another embodiment, more than one *B. subtilis* strain selected from a group consisting of: SG17, SG83 and SG140, may be used. For example, SG17 and SG83 could be used simultaneously, or SG17 and SG140 could be used simultaneously, and so on.

In yet another embodiment, one or more strains of *B. amyloliquefaciens* may be used in combination with one or more strains of *B. subtilis*, or extracellular material produced by the corresponding cell or disrupted cell homogenate therefrom. For example, *B. amyloliquefaciens* strain SG277 may be used with *B. subtilis* strain SG17, or *B. amyloliquefaciens* strain SG297 may be used with *B. subtilis* strain SG140, and so on.

The inventors have prepared novel antibacterial formulations comprising combinations of the various *B. amyloliquefaciens* and *B. subtilis* strains.

Accordingly, in a second aspect, there is provided an antibacterial formulation comprising a live or dead spore, or a live or dead vegetative cell of one or more *B. amyloliquefaciens* strains and/or one or more *B. subtilis* strains, or extracellular material produced by the live cell, or disrupted cell homogenate; and, optionally a pharmaceutically acceptable carrier or vehicle.

Preferably, the one or more *B. amyloliquefaciens* strains is selected from a group consisting of SG18, SG57, SG137, SG136, SG185, SG277 and SG297. SG277 and SG297 are the most preferred strains.

Preferably, the one or more *B. subtilis* strains is selected from a group consisting of SG17, SG183, and SG140. SG140 is the most preferred strain.

Preferably, the antibacterial formulation of the second aspect comprises a live or dead spore, or a live or dead vegetative cell, or extracellular material produced by the live cell, or disrupted cell homogenate therefrom, of at least one *B. amyloliquefaciens* strain and at least one *B. subtilis* strain. Preferably, the antibacterial formulation comprises a live or dead spore, or a live or dead vegetative cell, or extracellular material produced by the live cell, or disrupted cell homogenate therefrom, of a plurality of *B. amyloliquefaciens* strains and a plurality of *B. subtilis* strains.

Preferably, the live spore, dead spore, or live vegetative cell or dead cell, or the extracellular material produced by the live cell or disrupted cell homogenate therefrom, in accordance with the first or second aspect comprises an antibacterial composition.

The inventors believe that it is this antibacterial composition which is responsible for the surprising antibacterial activity exhibited.

Preferably, the antibiotic composition comprises: (i) a member of the Surfactin family, or an active derivative thereof.

Preferably, the antibiotic composition comprises: (ii) a member of the Iturin family, or an active derivative thereof.

The inventors have surprisingly demonstrated a synergistic effect between lipopeptides and antibiotics. The inventors believe that lipopeptides facilitate the formation of micelles. This process advantageously concentrates the antibiotics, stabilises them and enables killing of bacteria such as *C. difficile*. The inventor's data show that this is a universal strategy of many Bacilli (*B. amyloliquefaciens*, *B. subtilis* etc), and believe that the basic mechanism is that of forming micelles and concentrating antibiotics, and it is this synergy that promotes killing of pathogens including intestinal pathogens.

Thus, in a third aspect of the invention there is provided an antibiotic composition comprising: (i) an antibiotic and (ii) a lipopeptide selected from the group consisting of: a member of the Surfactin family; a member of the Iturin family; and a member of the Fengycin family or an active derivative of any of these lipopeptides.

The skilled person would understand that the term antibiotic relates to an antimicrobial compound.

In a fourth aspect, there is provided an antibiotic composition according to the third aspect, for use in therapy.

In a fifth aspect, there is provided an antibiotic composition according to the third aspect, for use in treating, preventing or ameliorating a bacterial infection.

In a sixth aspect of the invention, there is provided a method of treating, preventing or ameliorating a bacterial infection, the method comprising administering, to a subject in need of such treatment, a therapeutically effective amount of either:

(i) a live or dead spore, or a live or dead vegetative cell of *B. amyloliquefaciens* and/or *B. subtilis*, or extracellular material produced by the live cell, or disrupted cell homogenate; or (ii) an antibiotic composition comprising: (i) an antibiotic, and (ii) a lipopeptide selected from the group consisting of: a member of the Surfactin family; a member of the Iturin family; and a member of the Fengycin family or an active derivative of any of these lipopeptides.

In a seventh aspect of the invention, there is provided the use of the antibiotic composition according to the third aspect as a foodstuff or dietary supplement.

In an eighth aspect of the invention, there is provided a dietary supplement or foodstuff comprising the antibiotic composition according to the third aspect.

In some embodiments, the composition may be a probiotic, for example, when delivered in combination with a live spore or a live vegetative cell of *B. amyloliquefaciens* and/or *B. subtilis*. The foodstuff may be a beverage.

In another embodiment, the foodstuff may be a medical foodstuff, or "medical food". The skilled person would understand that the term "medical food" refers to a foodstuff that has a health claim associated with it.

It will be appreciated that the term "antibiotic composition" as used herein is responsible for the antibacterial activity exhibited by any of the live spore, dead spore, or live vegetative cell or dead cell, or the extracellular material produced by the live cell, or the disrupted cell homogenate, in accordance with the first aspect, or the formulation of the second aspect, or the composition of the third aspect, and any of the uses or methods described herein. The bacterial infection, which may be treated, prevented or ameliorated in accordance with any aspect of the invention may be a Gram-positive or a Gram-negative bacterial infection (see Table 7).

Preferably, the bacterial infection which may be treated, prevented or ameliorated is a Gram-positive bacterial infection. Examples of Gram-positive bacteria, which may be combated, include those in the phylum Firmicutes, which includes *Clostridium* spp., *Bacillus* spp., *Listeria* spp., *Mycobacterium* spp., *Lactobacillus*, *Staphylococcus* spp., *Streptococcus* spp. and *Enterococcus* spp. The bacterium may be *Bacillus* spp., preferably *B. anthracis* or *B. cereus* or *B. pumilis* or *B. clausii* or *B. megaterium* or *B. firmus* or *B. aquimaris*. The bacterium may be *Staphylococcus* spp., preferably *S. aureus* or *S. epidermis*. The bacterium may be *Listeria* spp., preferably *L. monocytogenes*. The bacterium may be *Enterococcus* spp., preferably *E. faecalis*. The bacterium may be *M. smegmatis*. The bacterium may be *M. tuberculosis*. The bacterium may be *Lactobacillus*, preferably *L. mucosae* or *L. fermentum* or *L. rhamnosus*.

Preferably, the bacterium is *Clostridium* spp., or *Staphylococcus* spp., and preferably *C. difficile* or *S. aureus*.

Most preferably, however, the bacterium is *Clostridium* spp., and most preferably *C. difficile*.

The inventors have demonstrated that, surprisingly, Chlorotetaine has antimicrobial activity against *C. difficile*. Accordingly, the invention also extends to Chlorotetaine, or a derivative or analogue thereof, for use in treating, preventing or ameliorating a *C. difficile* infection. The invention also extends to pharmaceutical compositions comprising Chlorotetaine, or a derivative or analogue thereof, for use in treating, preventing or ameliorating a *C. difficile* infection.

Accordingly, in another aspect, there is provided a method of treating, preventing or ameliorating a *C. difficile* infection, the method comprising administering or having administered to a subject in need of such treatment, a therapeutically effective amount of Chlorotetaine or a derivative or analogue thereof.

The inventors have also shown that the composition of the invention is active against *Mycobacterium* spp. Thus, preferably the bacterial infection which may be treated, prevented or ameliorated is a *Mycobacterium* spp., infection.

Preferably, the *Mycobacterium* spp., is *Mycobacterium tuberculosis* or *M. leprae* and most preferably *M. tuberculosis*.

Examples of Gram-negative bacteria, which may be combatted, include Enterobaceriaceae, such as *Salmonella* spp., and *Escherichia* spp., and *Campylobacter* spp., *Pseudomonas* spp. and *Vibrio* spp. The bacterium may be *Enterobacter* spp., preferably *E. aerogenes*. The bacterium may be *Escherichia* spp., preferably *E. coli*. The bacterium may be *Salmonella* spp., preferably *S. typhimurium*. The bacterium may be *Pseudomonas* spp., preferably *P. aeruginosa*. Preferably, the bacterium is *Vibrio* spp., preferably *V. parahaemolyticus* or *V. hareyi*.

The inventors have realised that the antibacterial activity observed against Gram-positive bacteria is bacteriocidal and in some cases bacteriolytic, whereas the activity observed against Gram-negative bacteria is bacteriostatic. Preferably, therefore, the antibiotic composition produced by the *Bacillus* strain of the invention exhibits bacteriocidal or bacteriolytic properties.

Where the lipopeptide is a member of the Iturin family, or active derivative thereof, the member of the Iturin family, or active derivative thereof may be selected from a group consisting of: Iturin A, Iturin $A_L$, Iturin C, Mycosubtilin, Bacillomycin D, Bacillomycin F, Bacillomycin L, Bacillomycin LC and Bacillopeptin.

In one embodiment, the general formula for members of the Iturin family or active derivative thereof may be as set out in formula I below, wherein R1 to R5 is any amino acid, and preferably R1 is Asn or Asp, R2 is Pro, Gln or Ser, R3 is Glu, Pro or Gln, R4 is Ser or Asn and R5 is Thr, Ser or Asn:

[I]

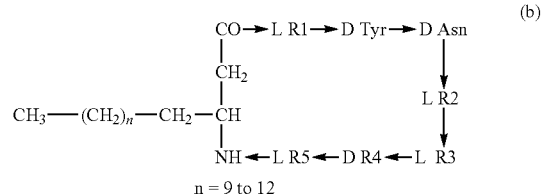

(b)

$n = 9$ to $12$

The member of the Iturin family, or active derivative thereof, may be Iturin A [SEQ ID NO:1], Iturin $A_L$ [SEQ ID NO:2], Iturin C [SEQ ID NO:3], Mycosubtilin [SEQ ID NO:4], or Bacillomycin D [SEQ ID NO:5], Bacillomycin F [SEQ ID NO:6], Bacillomycin L [SEQ ID NO:7], Bacillomycin LC [SEQ ID NO:8], Bacillopeptin A, Bacillopeptin B or Bacillopeptin C [SEQ ID NO: 17] the sequences of which are shown below:

| | | |
|---|---|---|
| Bacillomycin D | L-Asn-D-Tyr-D-Asn-L-Pro-L-Glu-D-Ser-L-Thr | n-$C_{14}$, i-$C_{15}$, ai-$C_{15}$ |
| Bacillomycin F | L-Asn-D-Tyr-D-Asn-L-Gln-L-Pro-D-Asn-L-Thr | i-$C_{16}$, i-$C_{17}$, ai-$C_{17}$ |
| Bacillomycin L | L-Asp-D-Tyr-D-Asn-L-Ser-L-Gln-D-Ser-L-Thr | n-$C_{14}$, i-$C_{15}$, ai-$C_{15}$ |
| Bacillomycin LC* | L-Asn-D-Tyr-D-Asn-L-Ser-L-Glu-D-Ser-L-Thr | n-$C_{14}$, i-$C_{15}$, ai-$C_{15}$, i-$C_{16}$ |
| Iturin A | L-Asn-D-Tyr-D-Asn-L-Gln-L-Pro-D-Asn-L-Ser | n-$C_{14}$, i-$C_{15}$, ai-$C_{15}$ |
| Iturin $A_L$ | L-Asn-D-Tyr-D-Asn-L-Gln-L-Pro-D-Asn-L-Ser | n-$C_{16}$, i-$C_{16}$ |
| Iturin C | L-Asn-D-Tyr-D-Asn-L-Gln-L-Pro-D-Asn-L-Ser | n-$C_{14}$, i-$C_{15}$, ai-$C_{15}$ |
| Mycosubtilin | L-Asn-D-Tyr-D-Asn-L-Gln-L-Pro-D-Ser-L-Asn | n-$C_{16}$, i-$C_{16}$, ai-$C_{17}$ |
| Bacillopeptin A, B and C: | cyclo[D-Asn-Ser-Glu-D-Ser-Thr-βAA-Asn-D-Tyr] | [SEQ ID NO: 17] | wherein the βAA for each of Bacillopeptin A, B and C is set out under R in Formula XIII below:

[XIII]

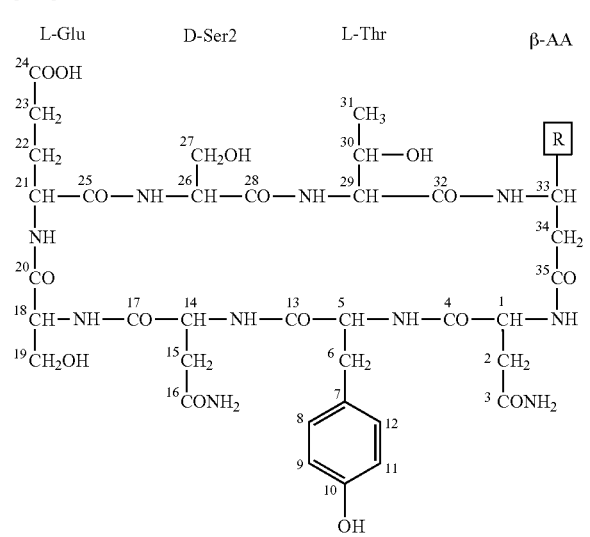

Preferably, the member of the Iturin family is Iturin A, or active derivative thereof. It will be appreciated that Iturin A is a lipopeptide. The Iturin A, or active derivative thereof, may be the $C_{14}$, $C_{15}$ or $C_{16}$ isoform. Active derivatives of Iturin A may therefore comprise any of the $C_{14}$, $C_{15}$ or $C_{16}$ isoforms. Most preferably, the Iturin A, or active derivative thereof, is the $C_{15}$ Iturin isoform.

In one embodiment, Iturin A may have an amino acid sequence as set out in SEQ ID NO: 1:

[SEQ ID NO: 1]
L-Asn-D-Tyr-D-Asn-L-Gln-L-Pro-D-Asn-L-Ser

Wherein n-$C_{14}$, i-$C_{15}$, ai-$C_{15}$

It will be appreciated that the member of the Surfactin family is a cyclic lipopeptide. In one embodiment where the lipopeptide is a member of the Surfactin family, the general formula for the members of the Surfactin family may be set out in formula II below, wherein R1-R4 is any amino acid, and preferably R1 is glutamine or glutamic acid, R2 is leucine or valine, R3 is valine, leucine or alanine, and R4 is leucine or valine.

[II]

The member of the Surfactin family may be selected from a group consisting of: Esperin [SEQ ID NO: 9], Lichenysin [SEQ ID NO: 10], Pumilacidin [SEQ ID NO: 11] and Surfactin [SEQ ID NO: 12].

| | | |
|---|---|---|
| Esperin | L-Glu-L-Leu-D-Leu-L-Val-L-Asp-D-Leu-L-Leu-COOH | |
| Lichenysin | L-$XL_1$-L-$XL_2$-D-Leu-L-$XL_4$-L-Asp-D-Leu-L-$XP_7$ | i-$C_{13}$, ai-$C_{13}$, n-$C_{14}$, i-$C_{15}$, ai-$C_{15}$ |
| Pumilacidin | L-Glu-L-Leu-D-Leu-L-Leu-L-Asp-D-Leu-L-$XP_7$ | |
| Surfactin | L-Glu-L-$XS_2$-D-Leu-L-$XS_4$-L-Asp-D-Leu-L-$XS_7$ | i-$C_{14}$, n-$C_{14}$, i-$C_{15}$, ai-$C_{15}$ |

Wherein XL1 is Gln or Glu; XL2 is Leu or Ile; XL4 and XL7 are Val or Ile

XP7 is Val or Ile

XS2 is Val, Leu or Ile; XS4 is Ala, Val, Leu or Ile; XS7 is Val Lu or Ile.

Preferably, the member of the Surfactin family is Surfactin, or an active derivative thereof. In one embodiment, Surfactin may have an amino acid sequence as set out in SEQ ID NO: 12:

[SEQ ID NO: 12]
L-Glu-L-XS$_2$-D-Leu-L-XS$_4$-L-ASP-D-Leu-L-XS$_7$

Active derivatives of Surfactin may therefore comprise any of the $C_{12}$, $C_{13}$, $C_{14}$, $C_{15}$, $C_{16}$, or $C_{17}$ isoforms. Preferably, the Surfactin is the $C_{16}$ isoform. The Surfactin, or active derivative thereof, may be the $C_{12}$, $C_{13}$, $C_{14}$, $C_{15}$, $C_{16}$, or $C_{17}$ isoform. Most preferably, the Surfactin, or active derivative thereof, is the $C_{15}$ isoform.

In one embodiment, a Surfactin may have a structure as set out in formula III:

[III]

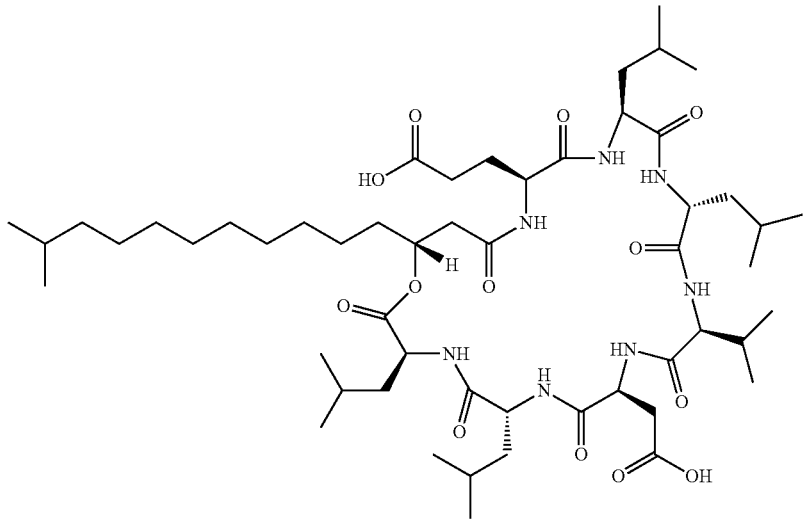

As described in the Examples, the members of the Iturin and Surfactin families act synergistically with each other to produce a surprising antibacterial activity. Therefore, preferably the composition comprises a member of the Iturin family, or active derivative thereof, and a member of the Surfactin family, or active derivative thereof. Preferably, the member of the Iturin family, or active derivative thereof, and member of the Surfactin family, or active derivative thereof, are used in a ratio of between 1:10 and 10:1, more preferably between 1:5 and 5:1, even more preferably between 1:3 and 3:1, more preferably between 1:2 and 2:1, and most preferably at a ratio of about 1:1.

It is especially preferred that the antibiotic composition of the third aspect, or that which contributes to the antibacterial activity exhibited by the live or dead spore, or a live or dead vegetative cell of *B. amyloliquefaciens* and/or *B. subtilis*, or extracellular material produced by the live cell, or disrupted cell homogenate, of the first aspect, or the formulation of the second aspect, comprises the $C_{15}$ isoform of Iturin A, and the $C_{15}$ isoform of Surfactin.

As described in Examples and above, the inventors have demonstrated surprising synergistic effects for compositions that comprise a biosurfactant (lipopeptides) and antibiotics. The inventors also believe that the presence of another biosurfactant, such as a glycolipid, in the antibiotic composition may be particularly advantageous.

Thus, in a preferred embodiment, the antibiotic composition of the third aspect further comprises a glycolipid. Preferably, the glycolipid is a Rhamnolipid or an active derivative thereof, and/or a Sophorolipid or an active derivative thereof.

Preferably, the glycolipid is a Rhamnolipid. The Rhamnolipid may be a Mono or Di Rhamnolipid.

Preferably, the Rhamnolipid is selected from the group consisting of the $C_8$, $C_{8:2}$, $C_{10}$, $C_{12}$, $C_{12:2}$, $C_{14}$ or $C_{14:2}$ isoforms.

Preferably, the Rhamnolipid is the C isoform.

In one embodiment, the Rhamnolipid has a general formula as set out in formula VIII:

[VIII]

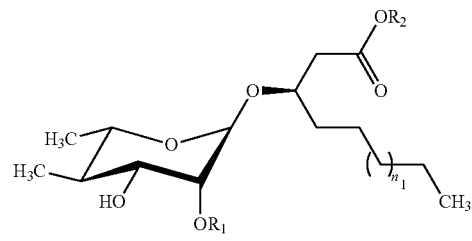

wherein $R_1$ $R_2$ and n, are as set out in the table below for each isoform:

| No. | Symbol | M. Form. | MW | $R_1$ | $n_1$ | $n_2$ | $R_2$ |
|---|---|---|---|---|---|---|---|
| 1 | Rha-$C_{8:2}$ | $C_{14}H_{22}O_7$ | 302.32 | H | 1 (−4H) | — | H |
| 2 | Rha-$C_8$ | $C_{14}H_{26}O_7$ | 306.35 | H | 1 | — | H |
| 3 | Rha-$C_{10}$ | $C_{16}H_{30}O_7$ | 334.41 | H | 3 | — | H |
| 4 | Rha-$C_{12:2}$ | $C_{18}H_{30}O_7$ | 358.43 | H | 5 (−4H) | — | H |
| 5 | Rha-$C_{12}$ | $C_{18}H_{34}O_7$ | 362.46 | H | 5 | — | H |
| 6 | Rha-$C_{14:2}$ | $C_{20}H_{34}O_7$ | 386.48 | H | 7 (−4H) | — | H |

In one embodiment, the Sophorolipid has a general formula as set out in formula IX:

IX

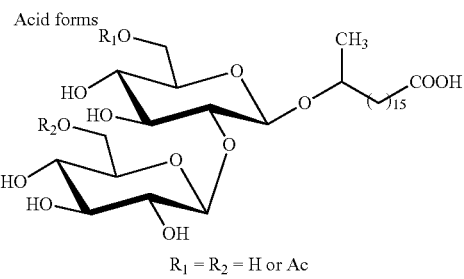

Acid forms $R_1 = R_2 = $ H or Ac

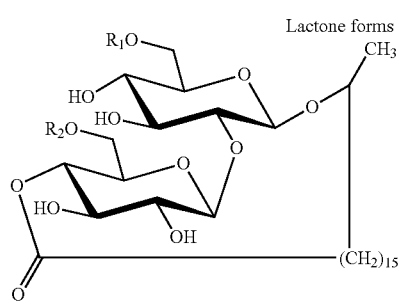

Lactone forms

SL-1: $R_1 = R_2 = $ Ac
SL-2: $R_1 = $ Ac, $R_2 = $ H
SL-3: $R_1 = $ H, $R_2 = $ Ac
SL-4: $R_1 = R_2 = $ H

As described above and in the Examples, the inventors have shown that a composition comprising the combination of lipopeptides and glycolipids is bacteriolytic.

The inventors have also surprisingly shown that the composition of the invention, when used in combination with antibiotic factors, results in synergistic effects, such that factors that are normally bacteriostatic that act by simply halting the growth and proliferation of bacterial cells, such as polyketides, display bacteriocidal activity when present in the antibiotic composition of the invention. The skilled person would understand that the term bacteriocidal refers to compositions that are capable of killing all of the bacteria present and are most preferable.

Without being bound to any particular theory, the inventors believe that lipopeptides, preferably together with glycolipids, produce mixed micelles that may incorporate or absorb other molecules such as antibiotics to have a synergistic antibacterial effect. Such that compositions that are separately bacteriostatic or bacteriolytic, when used in combination, have improved bacteriocidal properties.

Preferably, the antibiotic is Chlorotetaine or a polyketide, Bacilysin, Phoslactomycin or an active derivative thereof.

Preferably, the antibiotic is Chlorotetaine or a polyketide. Most preferably, the antibiotic is Chlorotetaine.

In one embodiment, the antibiotic is not Chlorotetaine.

The skilled person would understand that the Chlorotetaine may also be referred to as Chlorotetain.

In one embodiment Chlorotetaine has a structure as set out in formula XII:

[XII]

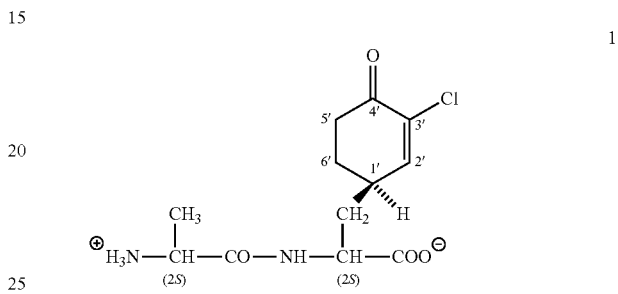

Accordingly, in a preferred embodiment, the antibiotic composition of the third aspect comprises: a lipopeptide and Chlorotetaine.

Preferably, the antibiotic composition of the third aspect comprises: a member of the surfactin family and Chlorotetaine.

In one embodiment, the antibiotic is a polyketide. The polyketide may be selected from a group consisting of Amicoumacin, Difficidin, Oxydifficidin and Salinipyrone A or an active derivative thereof of any one of these polyketides. Preferably, the polyketide is selected from the group consisting of Difficidin, Oxydifficidin and Amicoumacin.

The Amicoumacin may be Amicoumacin A, B or C. In one embodiment the Amicoumacin has a structure as set out in formula X:

[X]

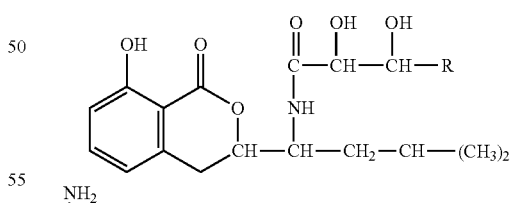

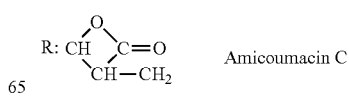

Preferably, the polyketide is Difficidin or Oxydifficidin.

In one embodiment, the Difficidin or Oxydifficidin has a structure as set out in formula XI:

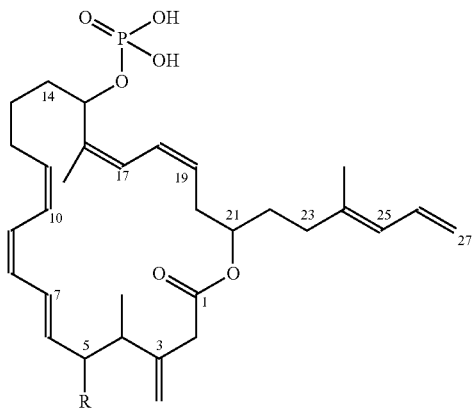

Difficidin R = H
Oxydifficidin R = OH

Accordingly, in a preferred embodiment, the antibiotic composition of the third aspect comprises: a member of the Surfactin family; and Difficidin or Oxydifficidin.

In another embodiment, the antibiotic composition of the third aspect comprises: a member of the Surfactin family and Difficidin or Oxydifficidin.

The antibiotic composition may comprise a member of the Fengycin family. In one embodiment, the general formula for members of the Fengycin family may be set out in formula IV below, wherein R1 to R3 is any amino acid, and preferably R1 is L or D Tyr, R2 is Ala or Val and R3 is L or D Tyr:

[IV]

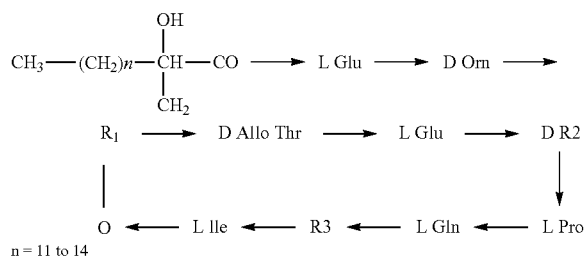

The member of the Fengycin family may be selected from a group consisting of: Fengycin A [SEQ ID NO: 13], Fengycin B [SEQ ID NO: 14], Plipastatin A [SEQ ID NO: 15] and Plipastatin B [SEQ ID NO: 16].

Preferably, the member of the Fengycin family comprises Fengycin A, or an active derivative thereof. The Fengycin A, or active derivative thereof, may be the $C_{15}$, $C_{16}$, $C_{17}$ or $C_{18}$ isoform. Most preferably, the Fengycin A is the $C_{15}$ Fengycin A isoform. The Fengycin A, or active derivative thereof, may be acetylated.

In one embodiment, Fengycin A may have an amino acid sequence as set out in SEQ ID NO: 13:

```
                                              [SEQ ID NO 13]
L-Glu-D-Orn-D-Tyr-D-aThr-L-Glu-D-Ala-L-Pro-L-Gln-L-
Try-L-Ile
```

Preferably, the member of the Fengycin family comprises Fengycin B, or an active derivative thereof. The Fengycin B, or active derivative thereof, may be the $C_3$, $C_{14}$, $C_{15}$ or $C_{16}$ isoform. Most preferably, the Fengycin B is the $C_{15}$ Fengycin B isoform. The Fengycin B, or active derivative thereof, may be acetylated.

In one embodiment, Fengycin B may have an amino acid sequence as set out in SEQ ID NO: 14:

```
                                              [SEQ ID NO: 14]
L-Glu-D-Orn-D-Tyr-D-aThr-L-Glu-D-Val-L-Pro-L-Gln-L-
Tyr-L-Ile
```

Preferably, the antibiotic composition in accordance with the invention comprises a further lipopeptide selected from a group consisting of: Mycosubtilin; Mojavensin A; and Kurstakin, or an active derivative of any of these lipopeptides.

The Mycosubtilin, or active derivative thereof, may be the $C_{17}$ isoform. In one embodiment, Mycosubtilin may have a structure as set out in formula V:

[V]

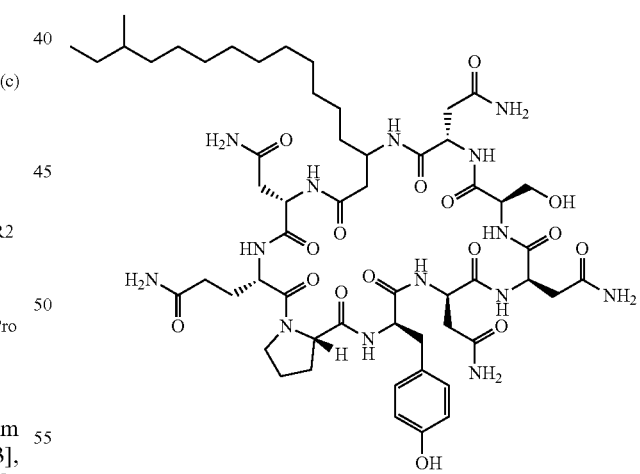

| | | |
|---|---|---|
| Fengycin A | L-Glu-D-Orn-D-Tyr-D-aThr-L-Glu-D-Ala-L-Pro-L-Gln-L-Tyr**-L-Ile | ai-$C_{15}$, i-$C_{16}$, n-$C_{16}$ |
| Fengycin B | L-Glu-D-Orn-D-Tyr-D-aThr-L-Glu-D-Val-L-Pro-L-Gln-L-Tyr**-L-Ile | ai-$C_{15}$, i-$C_{16}$, n-$C_{16}$, $C_{17}$ |
| Plipastatin A | L-Glu-D-Orn-L-Tyr-D-aThr-L-Glu-D-Ala-L-Pro-L-Gln-D-Tyr-L-Ile | n-$C_{16}$, ai-$C_{17}$ |
| Plipastatin B | L-Glu-D-Orn-L-Tyr-D-aThr-L-Glu-D-Val-L-Pro-L-Gln-D-Tyr-L-Ile | n-$C_{16}$, ai-$C_{17}$ |

The Mojavensin A, or active derivative thereof, may be the $C_{16}$ isoform. In one embodiment, Mojavensin A may have a structure as set out in formula VI:

[VI]

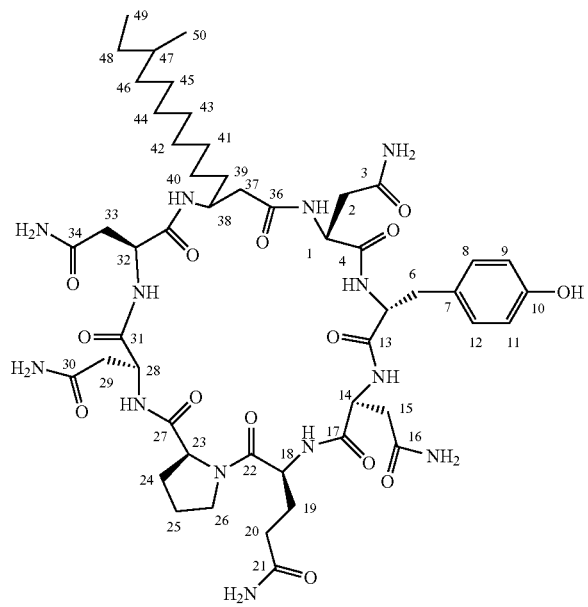

The Kurstakin, or active derivative thereof, may be the C isoform. Preferably, the Kurstakin is the $C_{15}$ Kurstakin isoform. In one embodiment, Kurstakin may have a structure as set out in formula VII:

[VII]

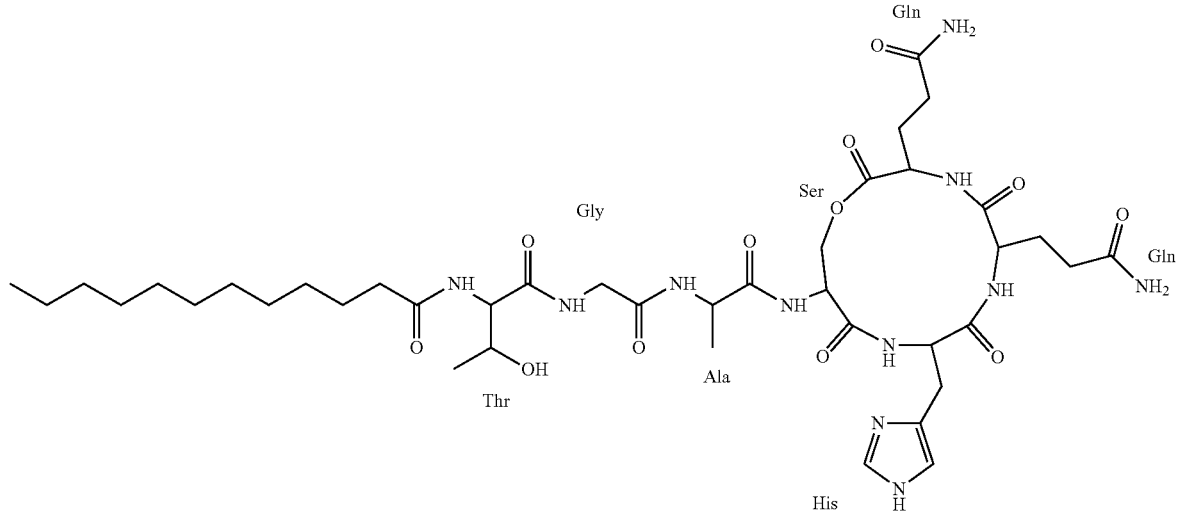

Preferably, the lipopeptide is Fengycin A, and, in a preferred embodiment, the antibiotic composition comprises the lipopeptides Iturin A, Surfactin and Fengycin A.

Preferably, the antibiotic composition comprises the lipopeptides Iturin A and Surfactin, and at least two further lipopeptides selected from a group consisting of: Fengycin A; Fengycin B; Mycosubtilin; Mojavensin A; and Kurstakin, or an active derivative of any of these lipopeptides.

Preferably, the antibiotic composition comprises the lipopeptides Iturin A and Surfactin, and at least three further lipopeptides selected from a group consisting of: Fengycin A; Fengycin B; Mycosubtilin; Mojavensin A; and Kurstakin, or an active derivative of any of these lipopeptides.

Preferably, the antibiotic composition comprises the lipopeptides Iturin A and Surfactin, and at least four further lipopeptides selected from a group consisting of: Fengycin A; Fengycin B; Mycosubtilin; Mojavensin A; and Kurstakin, or an active derivative of any of these lipopeptides.

In a most preferred embodiment, however, the antibiotic composition comprises the lipopeptides Iturin A, Surfactin, Fengycin A, Fengycin B, Mycosubtilin, Mojavensin A and Kurstakin, or active derivative thereof. As described in the Examples, there is surprising synergy between these compounds. Indeed, a total of 15 lipopeptides have thus far been identified and the antibacterial activity is greater than the sum of the parts.

Preferably, the antibiotic composition forms a complex having a molecular weight which is greater than 30 kDa, 4 kDa, 50 kDa, or 60 kDa. More preferably, the antibiotic composition forms a complex having a molecular weight greater than 70 kDa, 80 kDa, 90 kDa, or 100 kDa.

The inventors have surprisingly found that the antibacterial activity is water-soluble. Although most lipopeptides (such as Surfactin) are not water soluble, the inventors hypothesise that the combination of surfactants (for example, surfactins, iturins and/or fengycins etc.) with glycolipids (for example Rhamnolipids) renders the antibacterial activity water soluble, and more specifically makes the lipopeptide water soluble. The inventors have shown (see FIG. 20) that when combined, this high molecular weight complex of the active antibiotic composition is higher than that of the individual monomers, thereby indicating that micelles are preferably formed. Advantageously, these micelles act to promote cell lysis.

Preferably, therefore, the antibiotic composition forms micelles. The average diameter of the micelles may be between 1 nm and 500 nm, between 1 nm and 300 nm, between 1 nm and 200 nm, between 1 nm and 160 nm, between 1 nm and 100 nm, between 1 nm and 50 nm, between 1 nm and 15 nm, between 2 nm and 500 nm, between 2 nm and 300 nm, between 2 nm and 200 nm, between 2 nm and 160 nm, between 2 nm and 100 nm, between 2 nm and 50 nm, between 2 nm and 15 nm, between 3 nm and 500 nm, between 3 nm and 300 nm, between 3 nm and 200 nm, between 3 nm and 160 nm, between 3 nm and 100 nm, between 3 nm and 50 nm, between 3 nm and 15 nm, between 5 nm and 500 nm, between 5 nm and 300 nm, between 5 nm and 200 nm, between 5 nm and 160 nm, between 5 nm and 100 nm, between 5 nm and 50 nm, or between 5 nm and nm, between 10 nm and 500 nm, between 10 nm and 300 nm, between 10 nm and 200 nm, between 10 nm and 160 nm, between 10 nm and 100 nm, between 10 nm and 50 nm, or between 10 nm and 15 nm. Preferably the average diameter of the micelles is between 3 nm and 160 nm, and most preferably between 3 nm and 15 nm.

Advantageously, these micelles have been shown to aggregate into nanostructures, are more stable and resistant to degradation, have enhanced solubility and carry a higher antimicrobial activity than the monomeric form. The inventors believe that these micelles are stabilised or entrapped in the copious exopolysaccharides (EPS) that encase the vegetative cell mucilage. The 'active' strains described herein produce profuse biofilms and produced mucoid colonies, both attributes requiring the production of large amounts of extracellular polysaccharide.

The antibacterial activity of the antibacterial compositions described herein is believed to be associated with the cell envelope of the *Bacillus* strain producing the composition. Preferably, the antibiotic composition attaches to the cell surface of the *B. amyloliquefaciens* and/or *B. subtilis* and kills the bacterium, preferably *C. difficile*. Preferably, the antibiotic composition is associated with, or linked to, the *B. amyloliquefaciens* and/or *B. subtilis* cell wall, cell wall integuments or mucilage thereof. For example, the antibiotic composition may attach to the outer membrane vesicles. For example, when combating a Gram-positive bacterium, the cell envelope is a thick layer of peptidoglycan which is rich in lipoteichoic acids. Gram-positive bacteria are known to produce copious mucilage, and it can be assumed that they will have exopolysaccharides (EPS) associated with the outermost layers, as well as the possibility of poly-glutamic acid. Accordingly, although the inventors do not wish to be bound by any hypothesis, they believe that the EPS of the outer layers serves as a "glue" in which the active antibacterial molecules are embedded. Furthermore, the inventors hypothesise that this EPS material can dissociate from the cell wall, which may explain why activity in the cell free material (i.e., supernatant) is detected. In addition, some *Bacillus* species can form S-layers which lie above the peptidoglycan, and these are self-assembled layers, which are crystalline in nature. As such, the inventors believe that these strains have S-layers since some *Bacillus* strains do carry them, for example, *B. sphaericus, B. brevis, B. subtilis* as described in Sidhu & Olsen, Microbiology, 143: 1039-1052.

Accordingly, preferably the antibiotic composition of the invention further comprises cxopolysaccharide. For example, suitable cxopolysaccharides may include a monosaccharide, which may be galactose, fructose or glucose. The exopolysaccharide may also comprise arabinose. Each of these monomers were detectable in the samples tested.

Preferably, the antibiotic composition is substantially non-proteinaceous (though it will be appreciated that lipopeptides are present).

Preferably, the antibiotic composition comprises gamma-polyglutamic acid. The inventors have confirmed that the genomic sequences of preferred strains *B. amyloliquefaciens*, SG277 and SG297, both have genes involved in the biosynthesis of gamma-polyglutamic acid.

Taken together, therefore, the antibiotic composition of the invention preferably comprises a high molecular weight and non-proteinaceous complex, carrying a combination of exopolysaccharides and γ-PGA derived from the cell surface mucilage.

It will be appreciated that the antibiotic compositions and formulations according to the invention may be used in a monotherapy (i.e., the sole use of (i) a live or dead spore or a vegetative cell of *B. amyloliquefaciens* and/or *B. subtilis*, or extracellular material produced by the cell, or disrupted cell homogenate, or (ii) an antibiotic composition of the invention), for treating, ameliorating or preventing a bacterial infection, most preferably *Clostridium* spp., such as *C. difficile*. Alternatively, such antibiotic compositions and formulations according to the invention may be used as an adjunct to, or in combination with, known therapies for treating, ameliorating, or preventing bacterial infections, for example *Clostridium* spp. or *Bacillus* spp. For example, the agent may be used in combination with known agents for treating *Clostridium* spp. infections. Antibiotics used for *C. difficile* include clindamycin, vancomycin, and metrodinazole. Probiotics used for *C. difficile* include Lactobacilli spp., *Saccharomyces* spp. and *Bifidobacteria* spp.

The antibiotic compositions and formulations according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

The antibiotic compositions and formulations of the invention may be used in a number of ways. For instance, oral administration may be required, in which case the agents may be contained within a composition that may, for example, be ingested orally in the form of a tablet, capsule or liquid, which may include delivery of a composition present in food or a beverage. Antibiotic compositions and formulations of the invention may be administered by inhalation (e.g., intranasally). Compositions may also be formulated for topical use. For instance, creams or ointments may be applied to the skin. Alternatively, compositions may be delivered by sub-lingual administration.

Antibiotic compositions and formulations according to the invention may also be incorporated within a slow- or delayed-release device. Such devices may, for example, be inserted on or under the skin, and the medicament may be released over weeks or even months. The device may be located at least adjacent to the treatment site. Such devices may be particularly advantageous when long-term treatment with agents used according to the invention is required and which would normally require frequent administration (e.g., at least daily administration).

In a preferred embodiment, antibiotic compositions and formulations according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the antibiotic compositions and formulations that is required is determined by its biological activity and bioavailability, which in turn depends on the mode of administration, the physiochemical properties of the antibiotic compositions and formulations, and whether they are being used as a monotherapy or in a combined therapy. The frequency of administration will also be influenced by the half-life of the antibiotic compositions and formulations within the subject being treated. Optimal dosages to be administered may be determined by those skilled in the art, and will vary with the particular antibiotic compositions and formulations in use, the strength of the pharmaceutical composition, the mode of administration, and the advancement of the bacterial infection. Additional factors depending on the particular subject being treated will result in a need to adjust dosages, including subject age, weight, gender, diet, and time of administration.

Generally, a daily dose of between 0.001 µg/kg of body weight and 10 mg/kg of body weight of antibiotic composition or formulation according to the invention may be used for treating, ameliorating, or preventing bacterial infection, depending upon which antibiotic composition or formulation is used. More preferably, the daily dose is between 0.01 µg/kg of body weight and 1 mg/kg of body weight, more preferably between 0.1 µg/kg and 100pg/kg body weight, and most preferably between approximately 0.1 µg/kg and 10 µg/kg body weight.

The antibiotic composition or formulation may be administered before, during or after the onset of the bacterial infection. Daily doses may be given as a single administration (e.g., a single daily injection, or oral dose). Alternatively, the antibiotic composition or formulation may require administration twice or more times during a day. As an example, the antibiotic composition or formulation may be administered as two (or more depending upon the severity of the bacterial infection being treated) daily doses of between 0.07 µg and 700 mg (i.e., assuming a body weight of 70 kg). A patient receiving treatment may take a first dose upon waking and then a second dose in the evening (if on a two dose regime) or at 3- or 4-hourly intervals thereafter.

Alternatively, a slow release device may be used to provide optimal doses of antibiotic composition or formulation according to the invention to a patient without the need to administer repeated doses.

It will be appreciated that patients tend to get CDI when they are in hospital and taking antibiotics. Accordingly, it is preferred that the antibiotic compositions or formulations of the invention are administered prior to hospital entry (e.g., as prescribed over the counter), and then during the stay at hospital, and for a few days or weeks post-discharge. The antibiotic composition or formulation may therefore be used to prevent relapse of the bacterial infection.

Known procedures, such as those conventionally employed by the pharmaceutical industry (e.g., in vivo experimentation, clinical trials, etc.), may be used to form specific formulations of the antibiotic composition according to the invention and precise therapeutic regimes (such as daily doses of the antibiotic composition or formulation and the frequency of administration).

The invention also provides in a ninth aspect, a process for making the formulation according to the second aspect, the process comprising combining a therapeutically effective amount of a live or dead spore, or a live or dead vegetative cell of one or more *B. amyloliquefaciens* strains and/or one or more *Bacillus subtilis* strains, or extracellular material produced by the cell, or disrupted cell homogenate, with a pharmaceutically acceptable vehicle or carrier.

Preferably, the *B. amyloliquefaciens* strain that is used is selected from a group consisting of: SG18, SG57, SG137, SG136, SG185, SG277 and SG297. Most preferably, the *B. amyloliquefaciens* strain is SG277 or SG297. Preferably, the *B. subtilis* strain is selected from a group consisting of SG17, SG83 and SG140.

Preferably, the formulation comprises: (i) an antibiotic and (ii) a member of the Surfactin family, a member of the Iturin family and a member of the Fengycin family or an active derivative of any of these lipopeptides. Preferably, the formulation further comprises a glycolipid. Preferably, the formulation comprises: a member of the Surfactin family and Chlorotetaine. More preferably, the formulation comprises: a member of the Surfactin family; a Rhamnolipid and/or a Sophorolipid; and Chlorotetaine.

Preferably, the formulation comprises: an antibiotic; Iturin (preferably Iturin A); Surfactin; and at least one, two, three, four or five further lipopeptides selected from a group consisting of: Fengycin A; Fengycin B; Mycosubtilin; Mojavensin A; and Kurstakin, or an active derivative of any of these lipopeptides. Most preferably, the formulation comprises: an antibiotic; Iturin A; Surfactin; Fengycin A; Fengycin B; Mycosubtilin; Mojavensin A; and Kurstakin, or an active derivative of any of these lipopeptides.

A "subject" may be a vertebrate, mammal, or domestic animal. Hence, medicaments according to the invention may be used to treat any mammal, for example livestock (e.g., a horse), pets, or may be used in other veterinary applications. Most preferably, the subject is a human being.

A "therapeutically effective amount" of a live or dead spore, or a live or dead vegetative cell of one or more *B. amyloliquefaciens* strain and/or one or more *B. subtilis* strains, or extracellular material produced by the cell, is any amount which, when administered to a subject, is the amount of drug that is needed to treat the infection, or produce the desired effect.

For example, the therapeutically effective amount may be from about 0.001 µg to about 1 mg, and preferably from about 0.01 µg to about 100 µg. It is preferred that the amount of agent is an amount from about 0.1 µg to about 10 µg, and most preferably from about 0.5 µg to about 5 µg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The agent may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The agents and compositions of the invention may be administered sub-lingually, for example in the form of a slow release film, wafer or caplet.

To date, the scientific community focuses on anaerobes rather than aerobes to identify antibacterial activities. Surfactant molecules are known to form micelles at concentrations higher than the critical micelle concentration (CMC). Furthermore, acid precipitation and ultrafiltration is currently used to purify and concentrate antibacterial biosurfactants from anaerobes at concentrations greater than the CMC surfactants can be purified. As described in the Examples, the inventors have developed a new method which could be used for other pathogens (human or animal) for the identification of antibacterial activity. The inventors have shown that it is possible to identify aerobic bacteria exhibiting antibacterial activity by precipitating the high molecular weight fraction containing antibacterial complexes using ammonium sulphate. The inventors believe that the prior art methods using for example, ultrafiltration are unable to isolate the high molecular weight antimicrobial compounds.

Thus, in a tenth aspect of the invention, there is provided a method for identifying aerobic *Bacillus* spp. exhibiting antibacterial activity, the method comprising:—
(i) isolating aerobic spore forming bacteria;
(ii) aerobically culturing the isolated aerobic spore forming bacteria in culture medium;
(iii) sub-culturing aerobic bacteria from the culture medium of step (ii); and
(iv) carrying out an assay for the inhibition of bacterial cell growth using the sub-culture medium from step (iii) to identify aerobic *Bacillus* spp. exhibiting antibacterial activity.

Preferably, step (i) comprises isolating aerobic spore forming bacteria from faeces, most preferably homogenised faeces. For example, this may be achieved by plating on agar plates and incubation for about 1-4 days at about 30-42° C.

Preferably, step (ii) comprises aerobically culturing colonies of the isolated bacteria (preferably in rich liquid medium) for about 6-24 hours (e.g., at about 30-42° C., preferably with shaking).

Preferably, step (iii) comprises aerobically sub-culturing the culture from step (ii) (preferably in rich liquid medium) for about 12-36 hours (preferably, at about 30-42° C., and preferably with shaking).

Preferably, the method comprises a step of obtaining a supernatant from the culture of step (iii) prior to carrying out step (iv). Preferably, this step comprises removing the cells from the growth media to obtain the supernatant by centrifugation. For example, centrifugation may be conducted at at least 8000×g for at least 10 minutes. The supernatant may be sterile-filtered, for example through a suitable filter membrane, such as a 0.45 μm membrane.

Step (iv) may comprise any known assay useful to determine whether or not the sub-culture medium from step (iii) inhibits bacterial cell growth.

Preferably, following the step of assaying for the inhibition of bacterial cell growth, the method comprises a final step of processing the culture so as to precipitate a high molecular weight fraction comprising an antibacterial composition.

In one embodiment, this final step may comprise contacting either the raw culture or the supernatant with polyethylene glycol (PEG), or ethanol, or ethanol-water combinations to precipitate the high molecular weight fraction comprising an antibacterial composition. In a preferred embodiment, however, this final step comprises contacting either the raw culture or the supernatant with AmSO4.

Preferably, a final concentration of AmSO4 of between 5 and 50% (v/v), more preferably between 10 and 30% (v/v), even more preferably between 15 and 25% (v/v), and most preferably between 18 and 23% (v/v) is used.

The inventors believe that precipitating out the antibacterial composition is itself an important aspect of the invention, and enables the isolation of the antibacterial activity.

Thus, in a tenth aspect of the invention, there is provided a method for isolating an antibacterial composition from aerobic *Bacillus* spp. exhibiting antibacterial activity, the method comprising:—
(i) aerobically culturing *Bacillus* spp. cells in growth media;
(ii) processing the culture of step (i) so as to precipitate a high molecular weight fraction comprising an antibacterial composition.

In one embodiment, the method of the tenth aspect comprises testing the high molecular weight fraction precipitated in step (ii) for antibacterial activity against a bacterium using a suitable bacteriological assay. Preferably, however, the method of the tenth aspect is carried out after the method of the tenth aspect (i.e., isolation of the active antibacterial compounds after a useful antibacterial strain has been identified).

Preferably, the methods of the tenth and eleventh aspect are used to identify, and isolate antibacterial activity, from aerobic *Bacillus* bacteria that have antibacterial activity against gut pathogens, such as *Clostridium* spp., *C. difficile*, *E. coli*, *Salmonella* spp., *Campylobacter* spp. etc., in humans and also animals.

Preferably, step (i) of the method of the tenth aspect comprises culturing the aerobic *Bacillus* spp. cells in a suitable growth media, such as BHIB broth. Preferably, the cells are cultured overnight at about 37° C.

In one embodiment, step (ii) may comprise contacting either the raw culture or the supernatant with polyethylene glycol (PEG), or ethanol, or ethanol-water combinations to precipitate the high molecular weight fraction comprising an antibacterial composition. In a preferred embodiment, however, step (ii) comprises contacting either the raw culture or the supernatant with AmSO4. Preferably, a final concentration of AmSO4 of between 5 and 50% (v/v), more preferably between 10 and 30% (v/v), even more preferably between 15 and 25% (v/v), and most preferably between 18 and 23% (v/v) is used.

The high molecular weight fraction which is precipitated in the methods of the tenth and eleventh aspects may have a molecular weight of at least 10 kDa, 20 kDa, 30 kDa, 40 kDa, 50 kDa, or 60 kDa. More preferably, the high molecular weight fraction which is precipitated has a molecular weight of at least 70 kDa, 80 kDa, 90 kDa, or 100 kDa. Even more preferably, the high molecular weight fraction which is precipitated has a molecular weight of at least 150 kDa, 200 kDa, 150 kDa, or 300 kDa.

The methods of tenth and eleventh aspect preferably comprise:

obtaining the precipitate of the antibacterial composition, preferably by centrifugation.

For example, the centrifugation may be conducted at at least 8000×g for at least 15 minutes.

Preferably, the methods comprise:

resuspending the precipitate of the antibacterial composition, preferably in a suitable buffer, such as PBS.

Preferably, the methods comprise:

removing excess ammonium sulphate, PEG, ethanol, or ethanol-water combinations, for example using dialysis, and re-suspending the antibacterial composition, preferably in a suitable buffer, such as PBS.

Preferably, the methods comprise:

fractionating the antibacterial composition using chromatography, preferably size-exclusion chromatography, more preferably under denaturing conditions.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1A shows how groups of mice were dosed with clindamycin and suspensions of *Bacillus* isolated from the mouse GI-tract, challenged with spores of *C. difficile* strain 630, and then sacrificed and caecum samples taken; FIG. 1B is a graph showing the levels of toxin A determined in the caecum samples; and FIG. 1C is a graph showing the levels of *C. difficile* CFU determined in the caecum samples;

FIG. 2A is a graph showing the total number of aerobic bacteria identified in faecal samples taken from mice housed in either conventional cages (CC) or independently ventilated cages (IVCs); and FIG. 2B is a graph showing the heat-resistant, aerobic spore counts identified in the same faecal samples;

FIG. 3A shows cell free supernatants from overnight cultures of human isolates of *B. subtilis* (SG17, SG83, SG140) and *B. amyloliquefaciens* isolates (SG18, SG57, SG137, SG136, SG185, SG246, SG277, SG297) were filter-sterilised and used in a microdilution assay to quantify the level of inhibitory activity against *C. difficile* strain 630. The y-axis shows the maximum shows the maximum dilution of extracellular material required to inhibit growth of C. dilution of extracellular material required to inhibit growth of *C. difficile*. SG378 is a *B. amyloliquefaciens* strain that carried no activity and serves as a negative control; FIG. 3B shows a co-culture assay. Cell-free, sterile filtrate of SG277 was added to exponentially growing cultures ($OD_{600}$~0.5) of CD630. The time of addition is shown by an arrow. Growth was continued and $OD_{600}$ and viable counts (CFU/g) determined. Symbols: ○ CD630 untreated CFU; ● CD630+ SG277 filtrate; □ CD630 $OD_{600}$; and ■ CD630+SG277 filtrate $OD_{600}$;

FIG. 4A shows the stability of AmyCidem (AmyCidin™) in lyophilised form at different temperatures/storage conditions; FIG. 4B is a graph showing how SG277 was grown in BHIB medium; FIG. 4C is a graph showing how activity against CD630 determined using the microdilution assay varied for samples of the SG277 taken at hourly time points (from FIG. 4B). Increased inhibitory activity correlates with a higher dilution factor in the assay. Synthesis of activity in stationary phase defines activity as an antibiotic.

FIG. 5A shows an agar plate with a CD630 lawn; and FIG. 5B shows a plate with a CD630 lysed lawn;

FIG. 6A is a graph showing *C. difficile* CFU found in caecum samples taken from groups of mice (n=10) that were dosed (i.g.) five times with different prophylactic treatments using a schedule as shown in FIG. 1A; FIG. 6B is a graph showing toxin A levels in the caecum samples; and FIG. 6C is a graph showing toxin B levels in the caecum samples. Treatments were: SG277 overnight culture suspended in cell supernatant (277-SUP); SG277 overnight culture suspended in PBS (277-PBS); sterile cell-free supernatant of SG277 grown overnight (SUP); purified spores of SG277 (SPORES); overnight culture of SG378 suspended in their sterile cell-free supernatant (378); and animals received PBS buffer (naïve);

FIG. 7A shows survival curves for groups of hamsters (n=6) which were dosed (i.g.) with different prophylactic treatments before and after challenge with $10^2$ spores of CD630 (methods). Treatments were: 277-SUP, 277-PBS, SUP, SPORES, 378, and naïve. CD630 challenge was made 3 days after treatment (i.g.) after which animals were monitored for symptoms. Animals showing symptoms were sacrificed; FIG. 7B is a graph showing levels of CD630 CFU in caecum samples; FIG. 7B is a graph showing levels of CD630 CFU in caecum samples; and FIG. 7C is a graph showing levels of toxins A and B in caecum samples.

FIG. 8A shows an AmSO4 precipitation using 20%, 70% cuts or 20% followed by 70% (2×). Precipitates were run on 12% SDS-PAGE and Coomassie stained. A white Ghost Band (GB) was observed close to the dye front. Using a well diffusion assay only the 20% cut carried activity against *C. difficile* and biosurfactant activity; FIG. 8B shows the AmSO4 precipitation stained with Coomassie Blue (CB), Alcian blue (AB), Oil Red (OR) and unstained (US); Ghost band indicated by arrow. FIG. 8C is a graph showing the protein concentration and activity (i/dilution factor) of the AmSO4 (20%) precipitate solubilised in water and run through a Superdex 200 gel filtration column; and FIG. 8D shows a CsCl gradient centrifugation of an PEG precipitation of SG277 sterile filtrate fraction with 3 bands observed (B1, B2 and B3);

FIG. 9A is an electron microscope image of aggregates of the active fraction (B2 of FIG. 8D) following centrifugation through a CsCl gradient; and FIG. 9B is an electron microscope image of aggregates after size exclusion chromatography, the size marker is 100 nm;

FIG. 10A is an RP-HPLC chromatogram of SG277 biosurfactants. Following AMSO4 precipitation and size exclusion chromatography (SEC), the sample was analysed by RP-HPLC. Each fraction was analysed by MALDI-TOF to identify the active component(s) revealing different isoforms of Iturin A (fractions 1 to 5), Surfactin (fractions 10 to 15) and Fengycin A and B (fractions 7 to 9) as well as Mycosubtilin (fraction 6); and FIG. 10B shows activity to *C. difficile* using a microdilution assay. SEC fraction is the activity (1/128) of the crude SEC material before RP-HPLC analysis. Sum of individual fractions=mathematical total of positive peaks (1/125). Combined positive peaks=fractions with +ve activity were combined, evaporated and tested giving activity of 1/20. Combined all peaks=fractions 1-15 combined, evaporated and tested for anti-CD activity (1/640). Combined negative peaks=all negative fractions combined and tested for anti-CD activity (1/10).

Figure 18A:
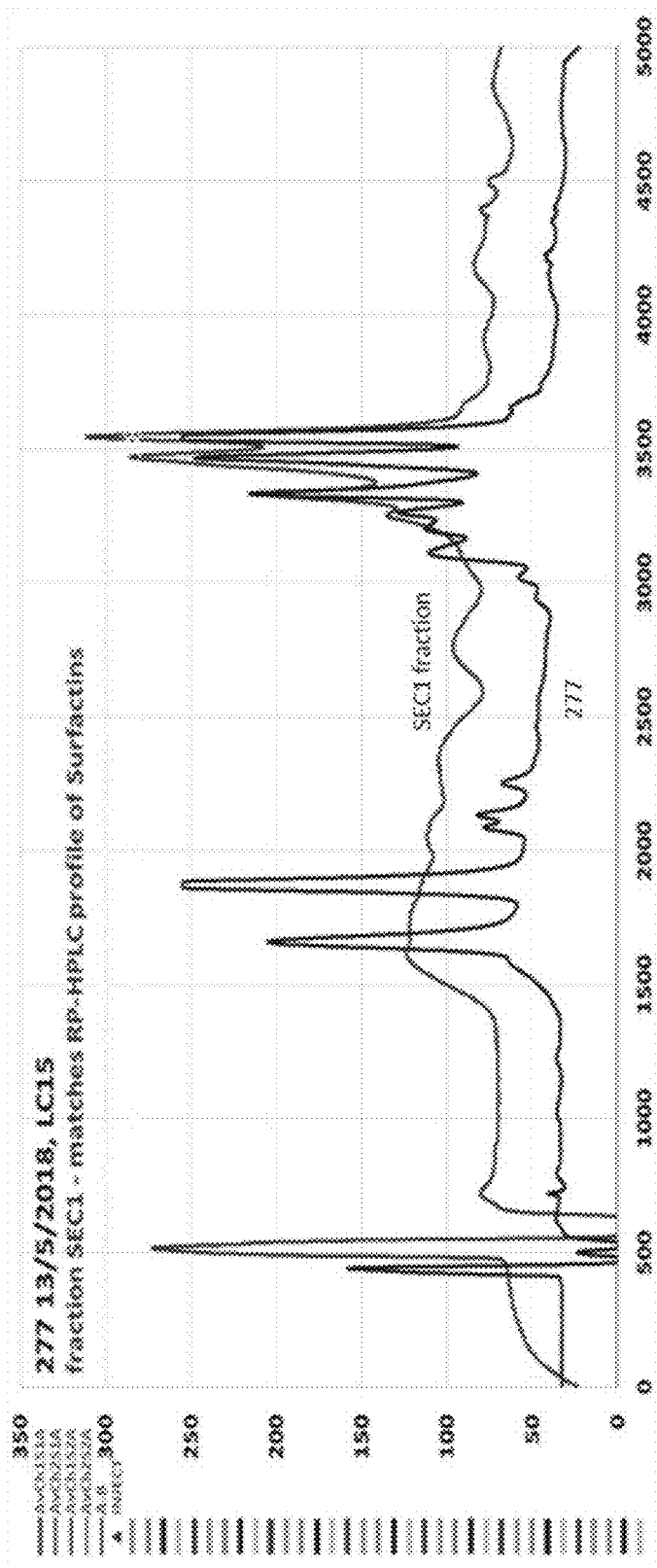
Figure 18B:
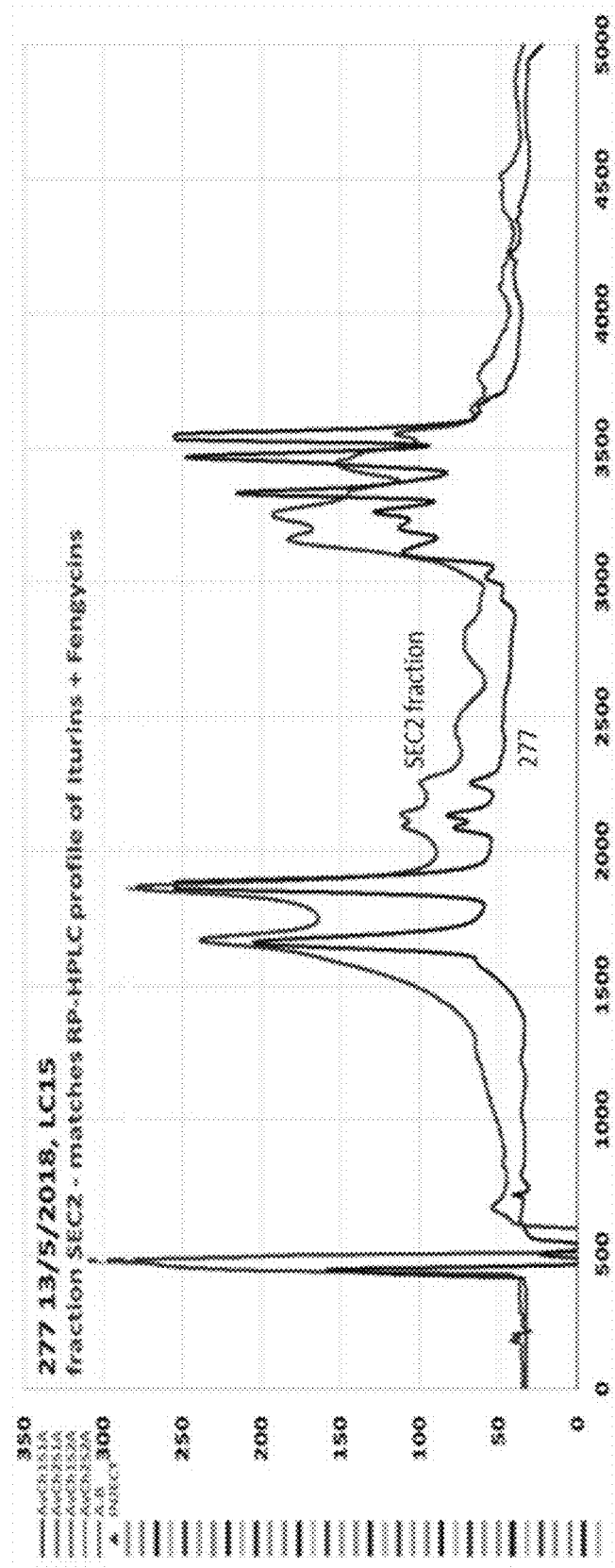
Figure 18C:
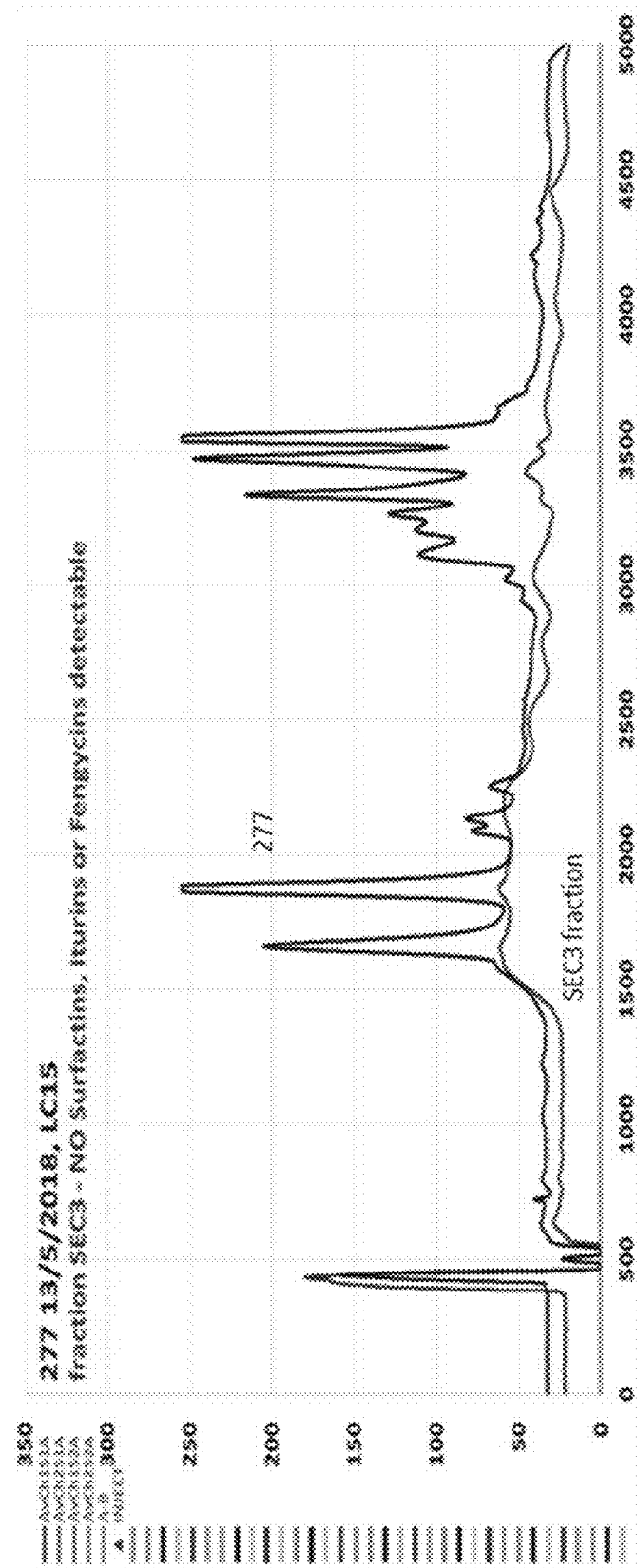

FIG. 18 shows RP-HPLC column profile of individual fractions from SEC-HPLC analysis, FIG. 18A shows that SEC-HPLC fraction 1 is surfactins since its chromotographic profile matches the surfactin peaks present in SG277's RP-HPLC profile, FIG. 18B shows that SEC-HPLC fraction 2 is a mixture of iturins and fengycins, since its chromatographic profile matches the iturin and fengycin peaks present in SG277's RP-HPLC profile, FIG. 18C shows no absorption at 220 nm (likely if there is no protein component) for SEC-HPLC fraction 3.

Figure 19:
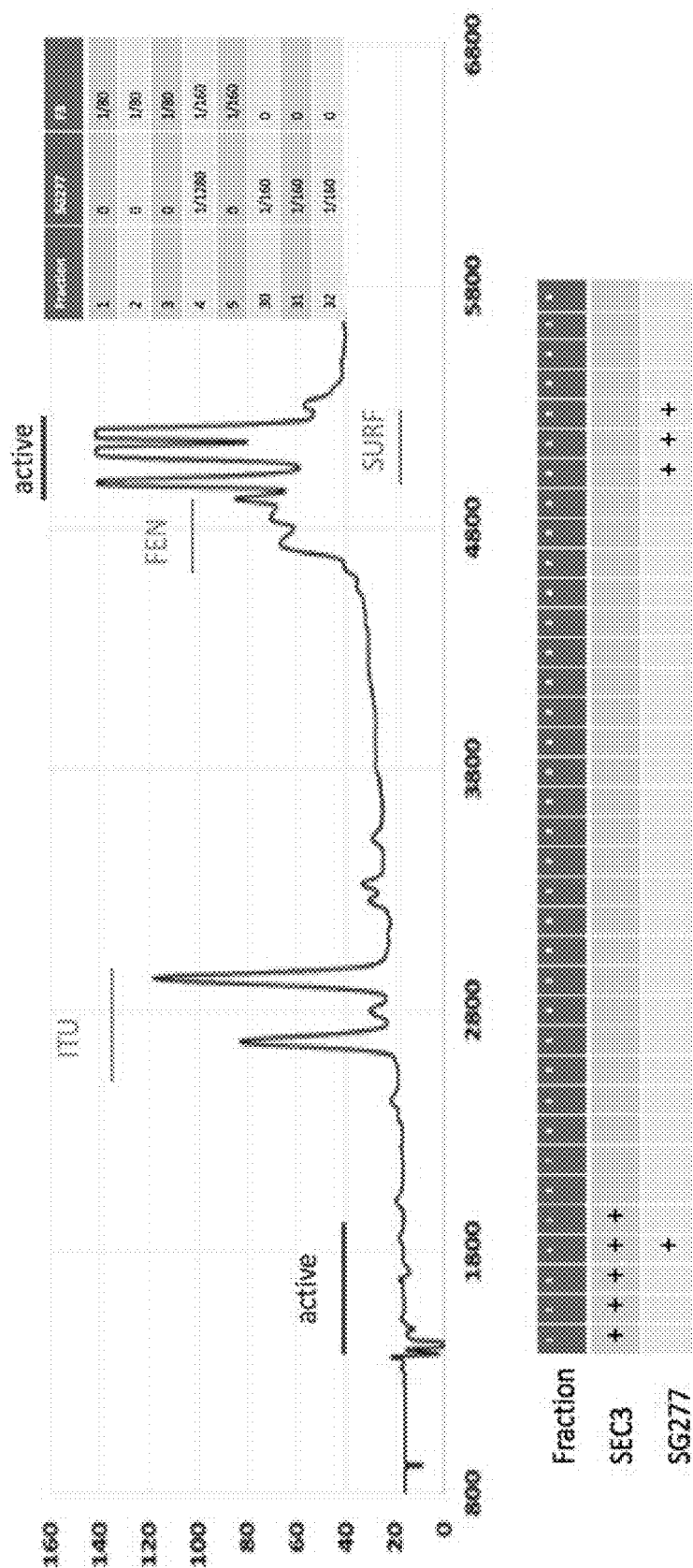

FIG. 19 shows a detailed analysis of SEC-HPLC fraction 3. Fraction 3 of SEC-HPLC analysis (from FIG. 17) was fractionated by RP-HPLC and resulting fractions examined for anti-CD630 activity (row=SEC3). In parallel, SEC crude material from SG277 was examined by RP-HPLC and fractions also examined for anti-CD activity (row=SG277). Fractions with activity are labelled+.

Figure 20:
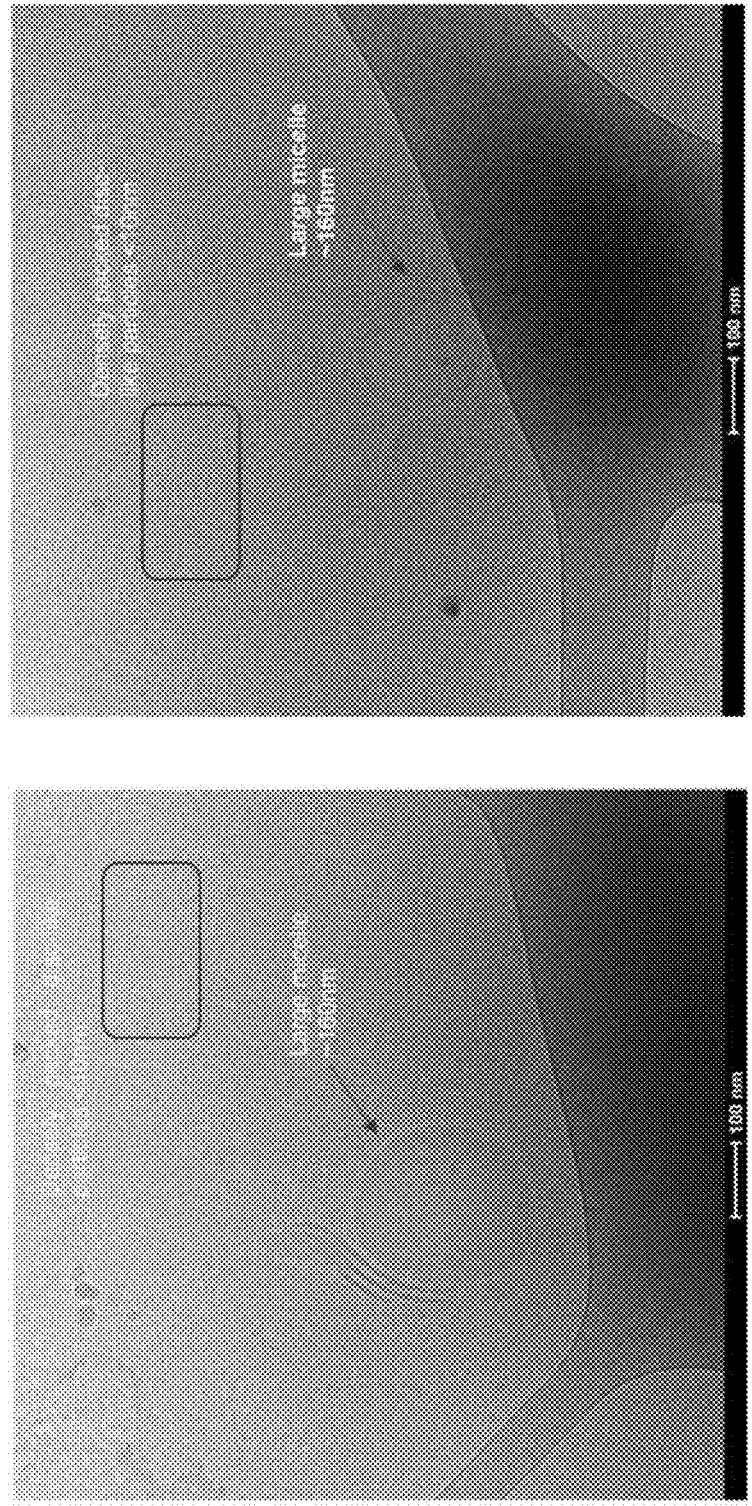

FIG. 20 shows Cryo-EM analysis of two independent samples of SEC material.

Figure 21A:
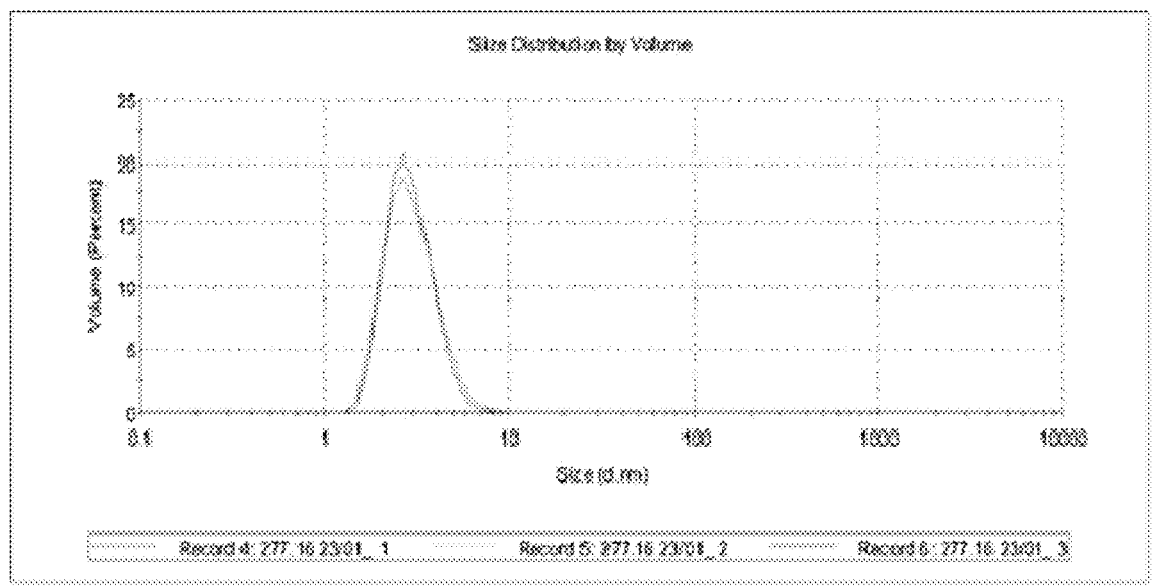
Figure 21B:
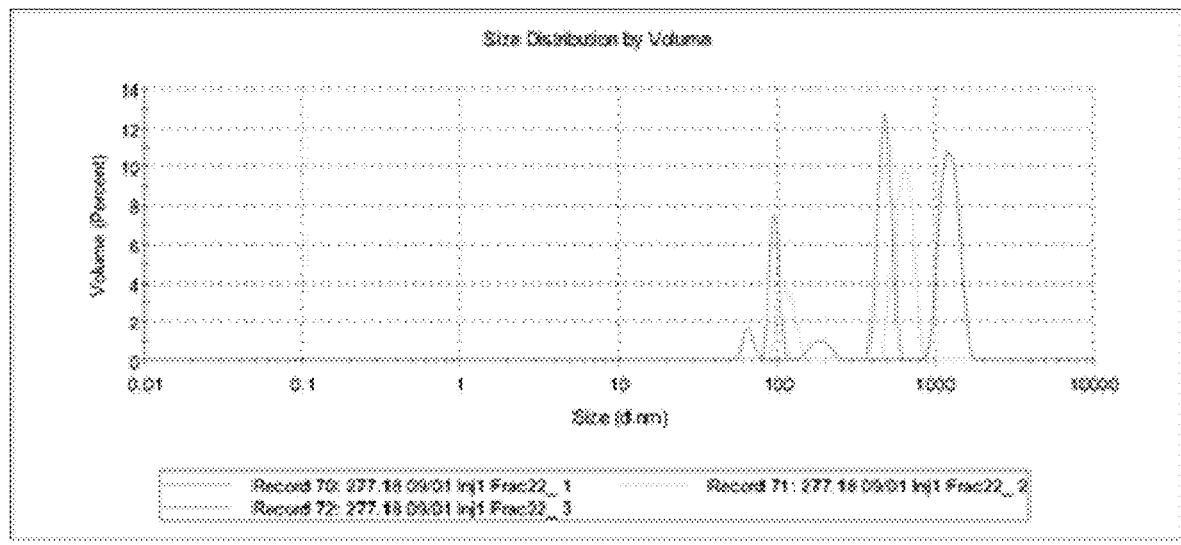

FIG. 21A shows Dynamic Light Scattering (DLS) analysis of the SEC fraction and FIG. 21B shows Dynamic Light Scattering of $C_{14}$ surfactin (fraction 13 from RP-HPLC).

Figure 22A:
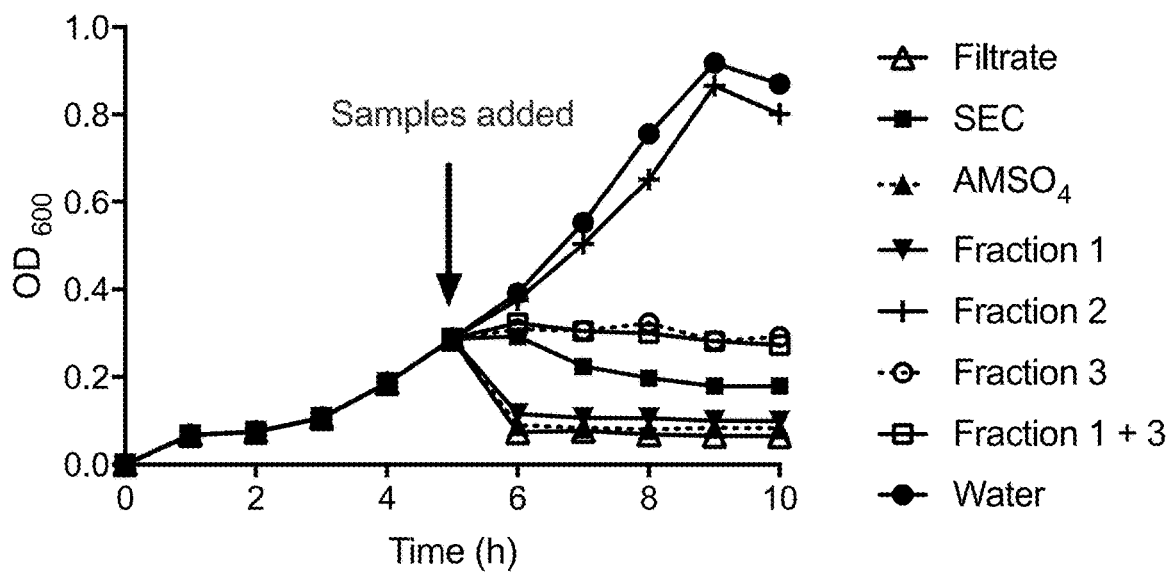
Figure 22B:
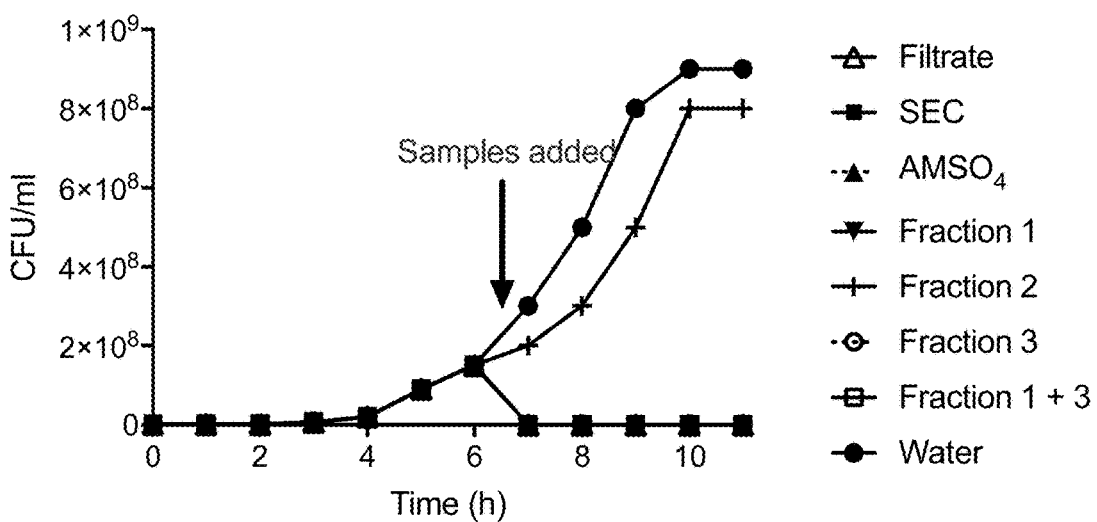

FIG. 22A shows OD600 measurements before and after addition of test material (samples), FIG. 22B shows CFU readings before and after addition of test material.

Figure 23:
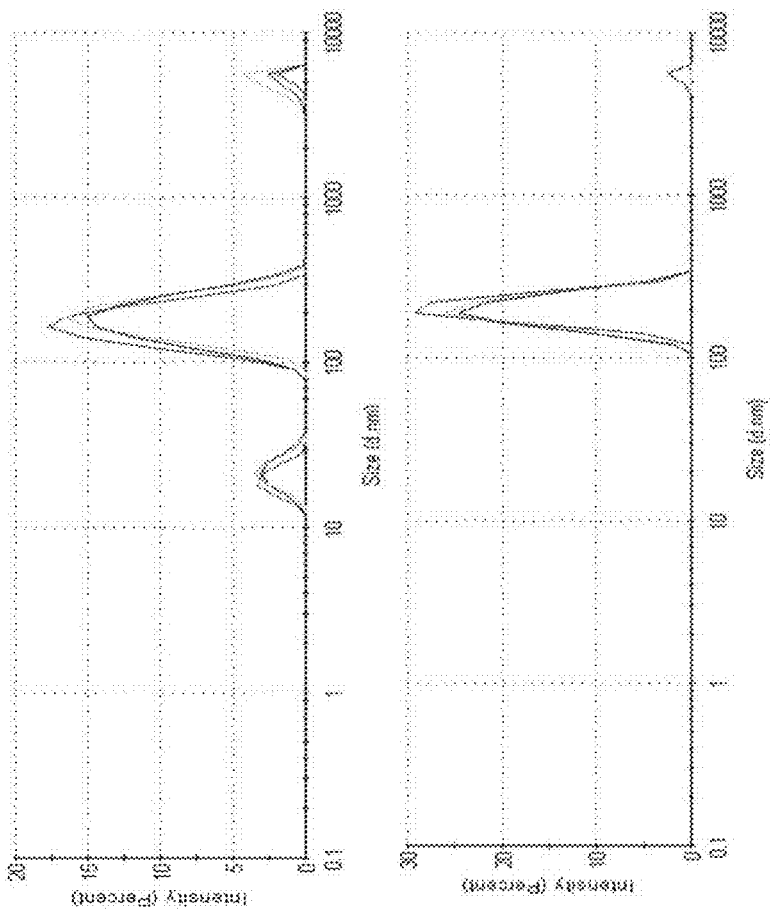
Figure 23:
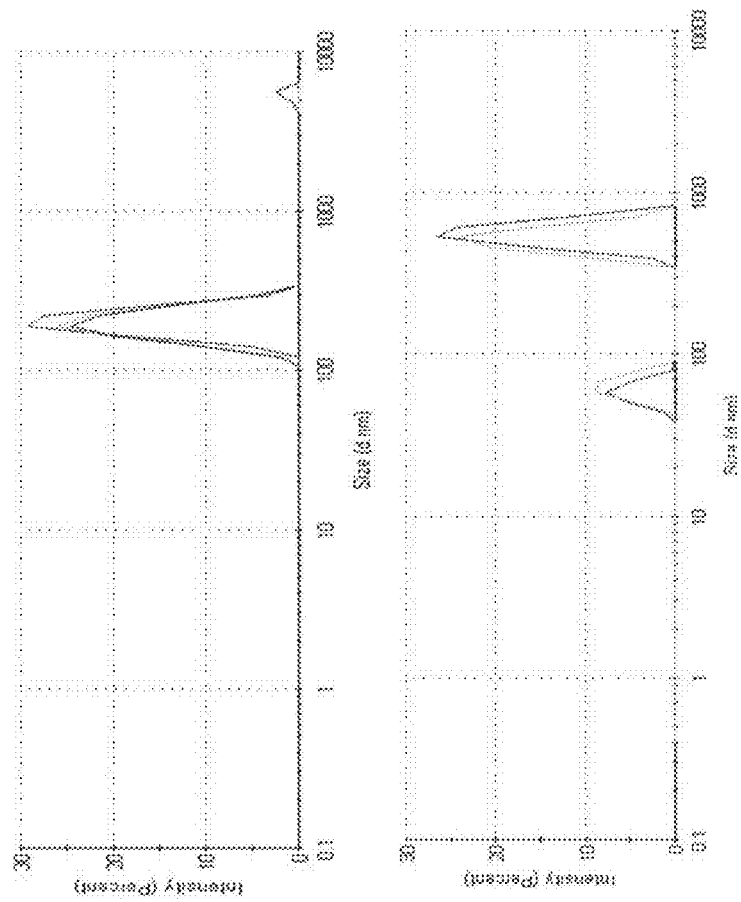

FIG. 23 shows DLS assessment of particle size in RP-HPLC fractions of iturins (I), fengycins (F) and surfactins (S) or combinations (I+F+S).

Figure 24:
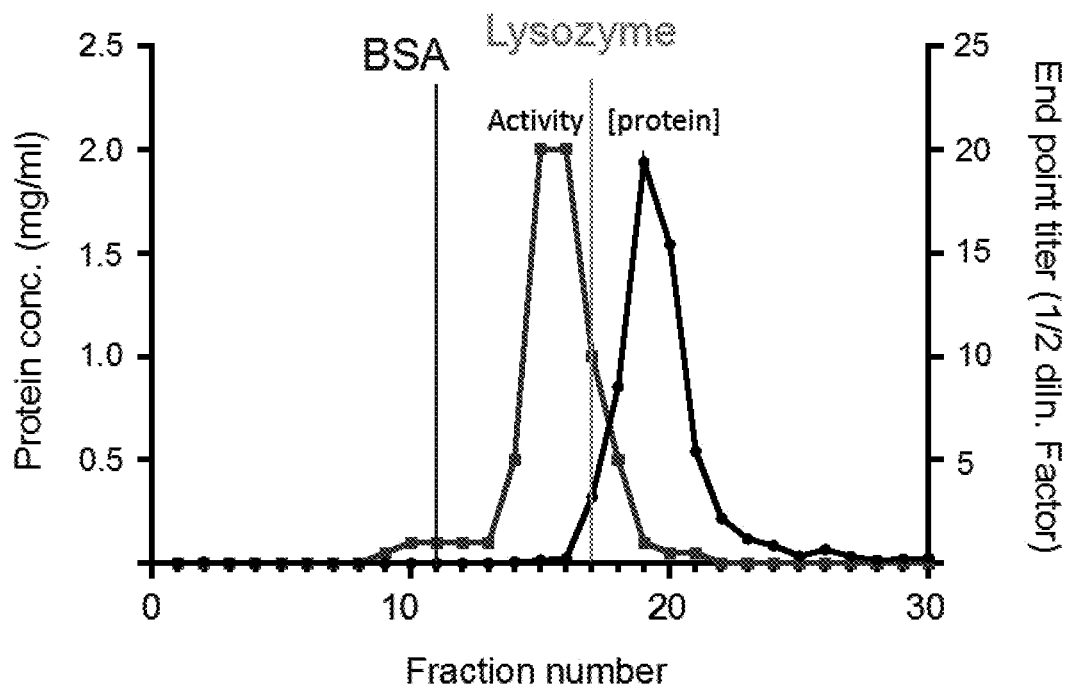

FIG. 24 shows SEC analysis of AmSO4 precipitate using internal protein markers (BSA and lysozyme).

Figure 25:
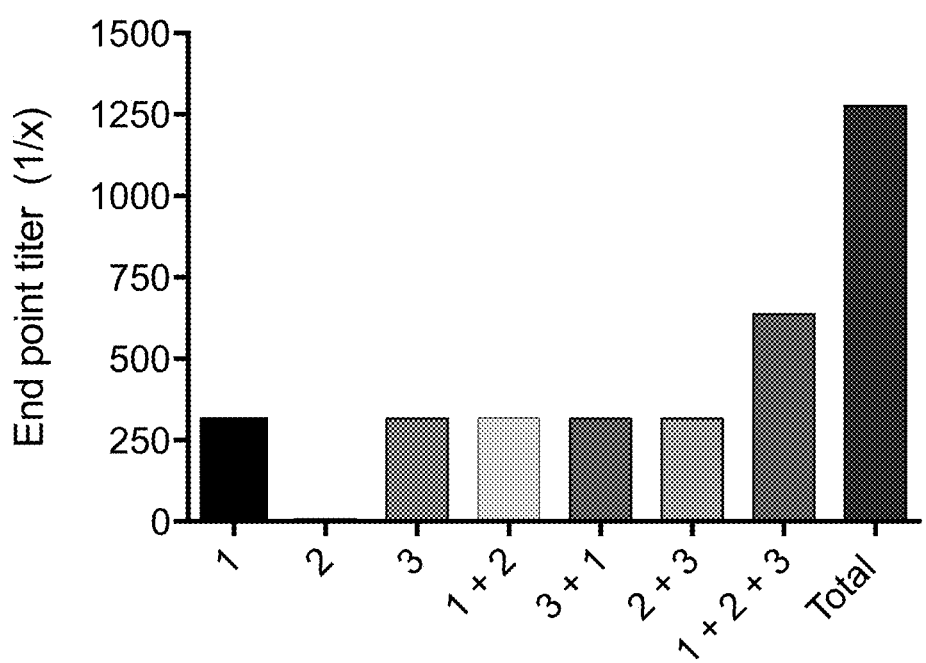

FIG. 25 shows the activity to CD630 of SEC-HPLC factions 1-3 either alone or in combination.

Figure 26:
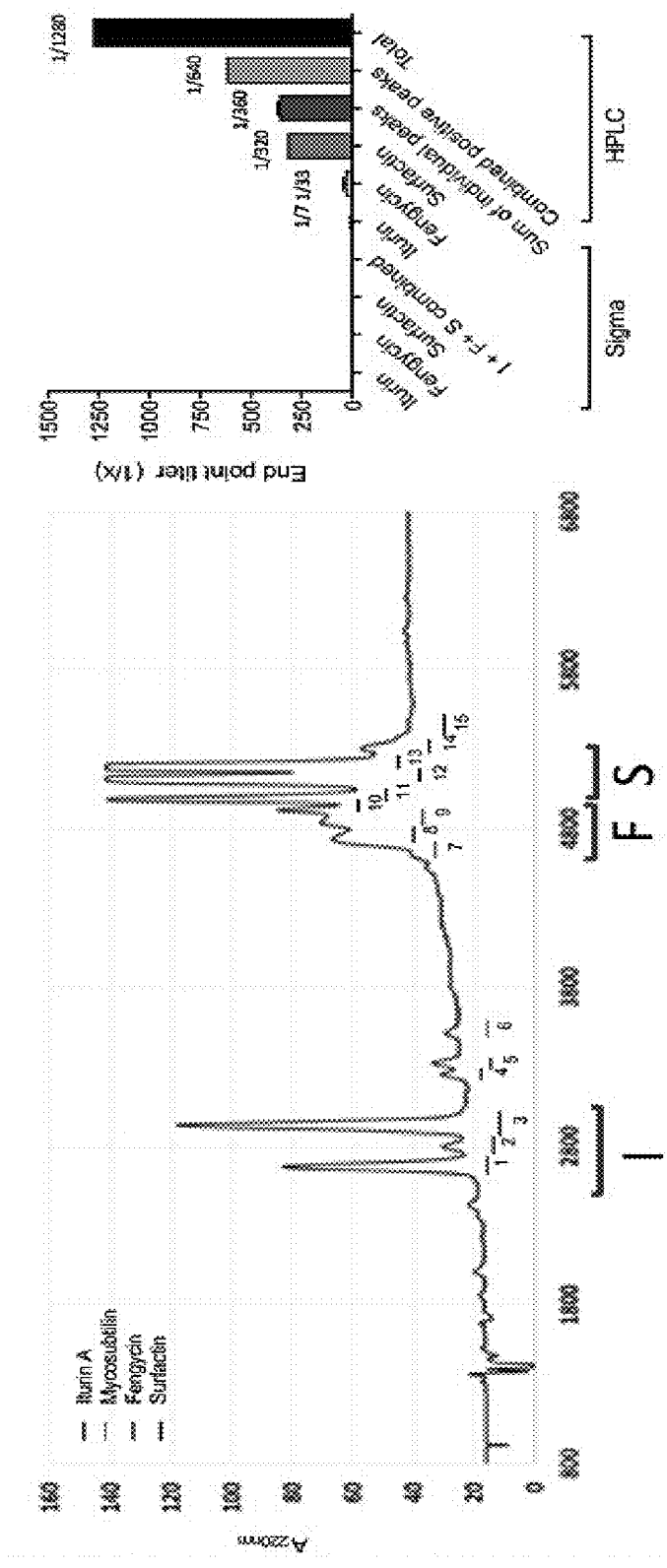

FIG. 26 shows the fractions from RP-HPLC fractionation, and the comparison with commercial samples of iturin, fengycin and surfactin with regard to anti-CD activity whether alone or in combination.

Figure 27:
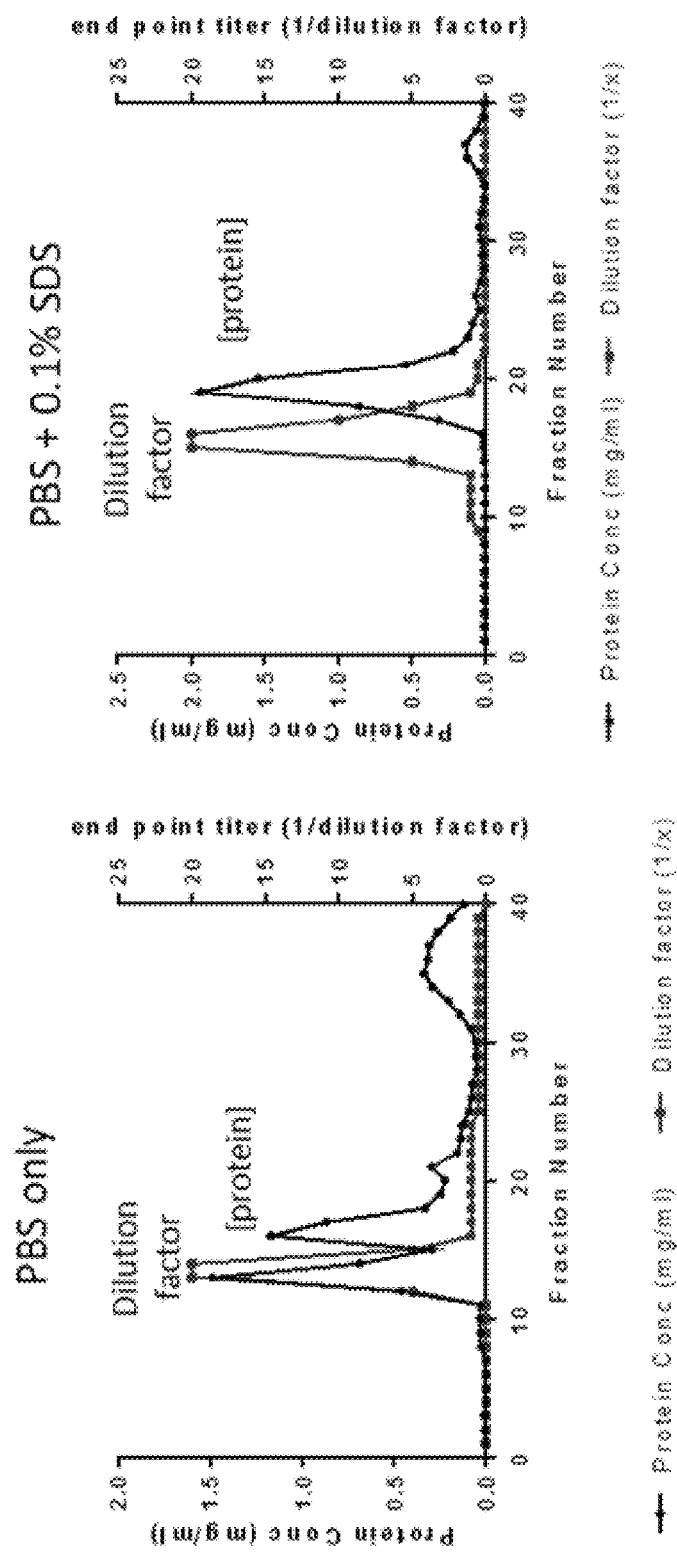

FIG. 27 shows analysis of AmSO4 precipitate by SEC using PBS or PBS+0.1% SDS, performed by determining the protein concentration and (A280 nm) and anti-CD630 activity using a microplate assay.

Figure 28:
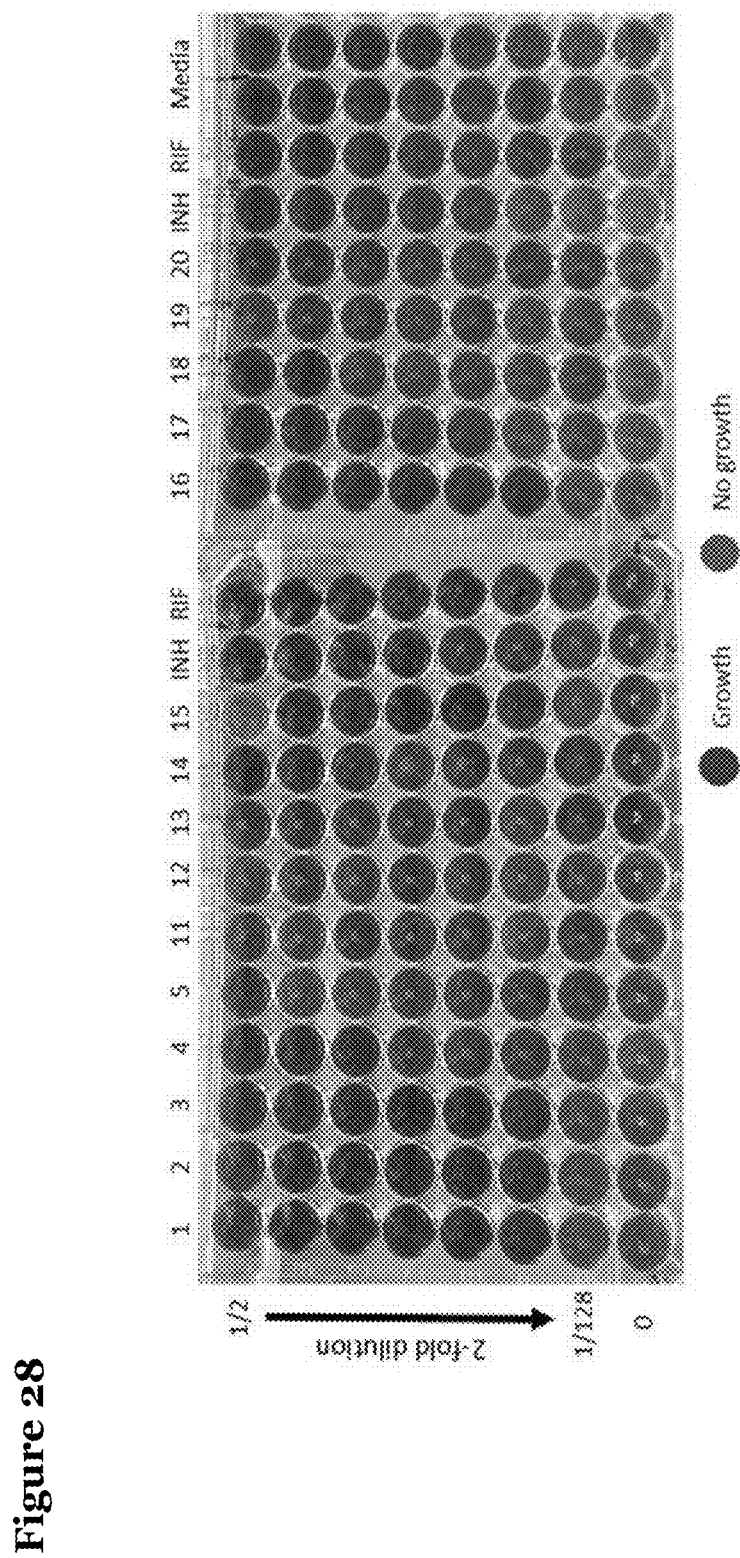

FIG. 28 shows REMA plate determining MIC of compounds for drug sensitive *M. tuberculosis* H37Rv. Conversion of resazurin (blue) to resorufin (pink) indicates mycobacterial growth. First blue well indicating no growth determines the MICs.

Figure 29:
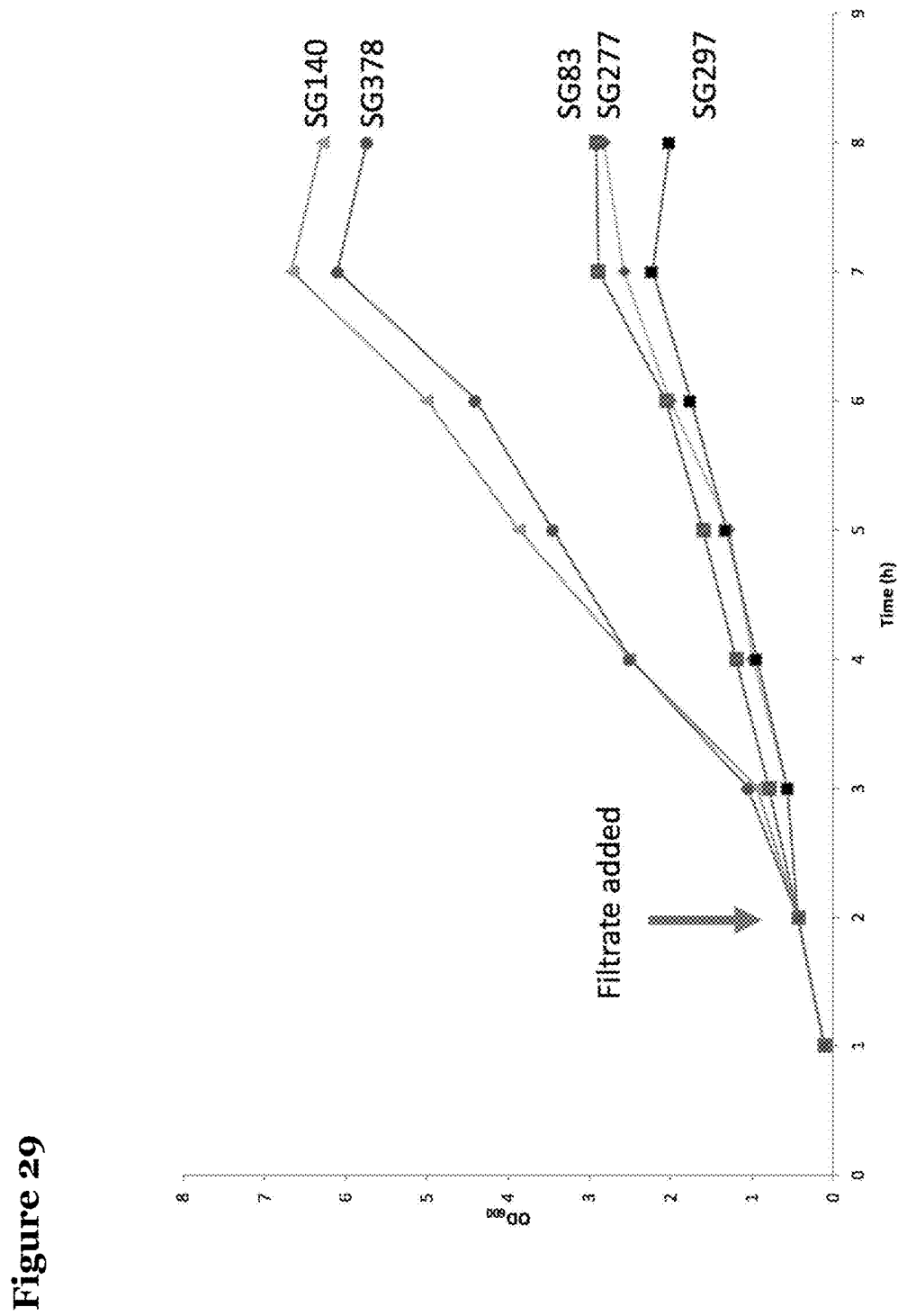

FIG. 29 shows the activity of the compounds against *S. aureus*. Sterile filtrates of a variety of *B. amyloliquefaciens* or *B. subtilis* strains were added to exponentially growing cultures of *S. aureus*. Cell growth was monitored by optical density readings.

Figure 30:
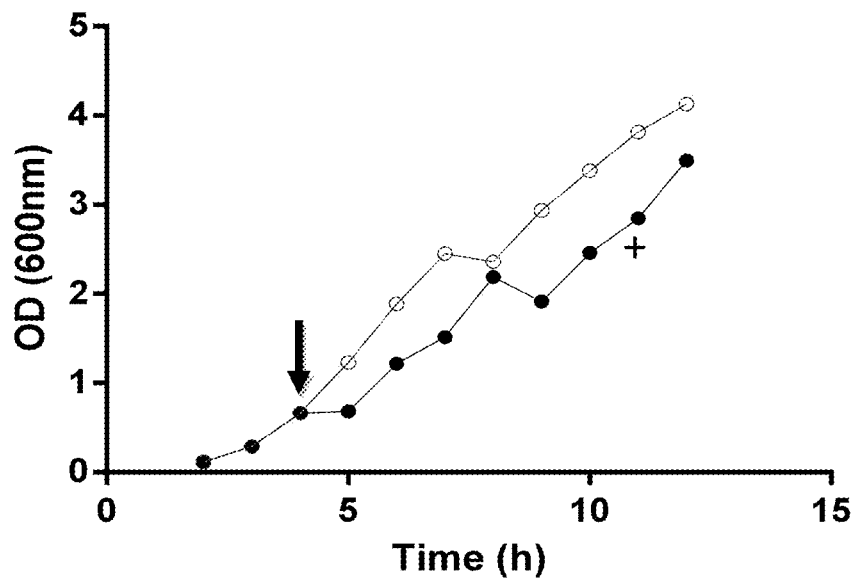

FIG. 30 shows activity of the compounds against *V. harveyi* SG527 OD600 readings. The arrow indicates time at which supernatants of SG277 were added. Open circle=no supernatant and filled circle=+SG277.

Figure 31:
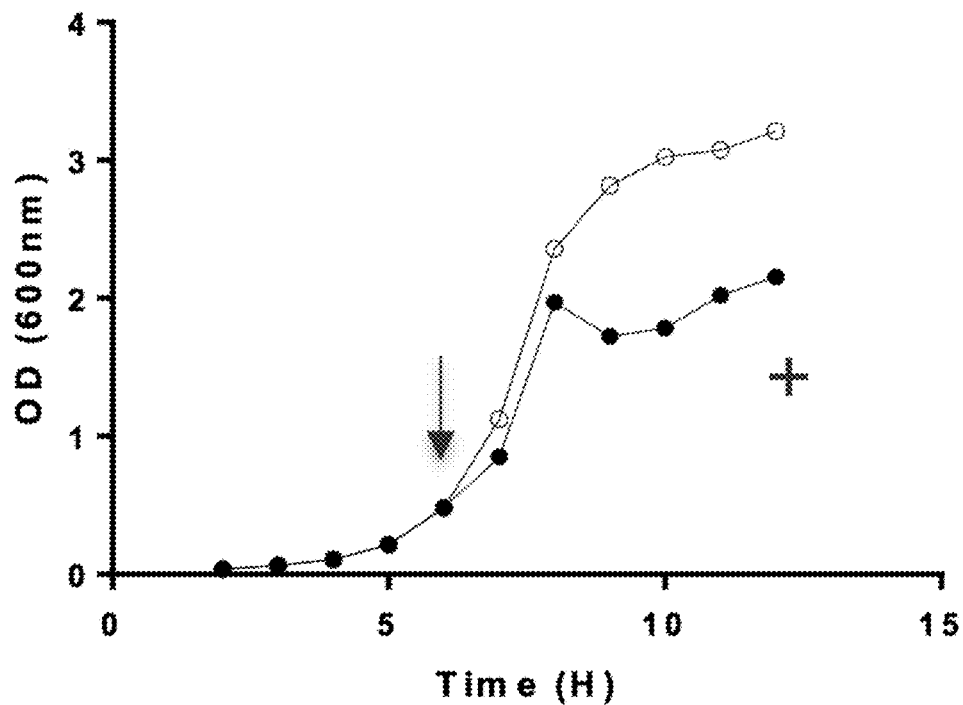

FIG. 31 shows activity of the compounds against *V. parahemolyticus* SG529 OD600 readings. Arrow indicates time at which supernatants of SG277 were added. Open circle=no supernatant and filled circle=+SG277.

Figure 32:
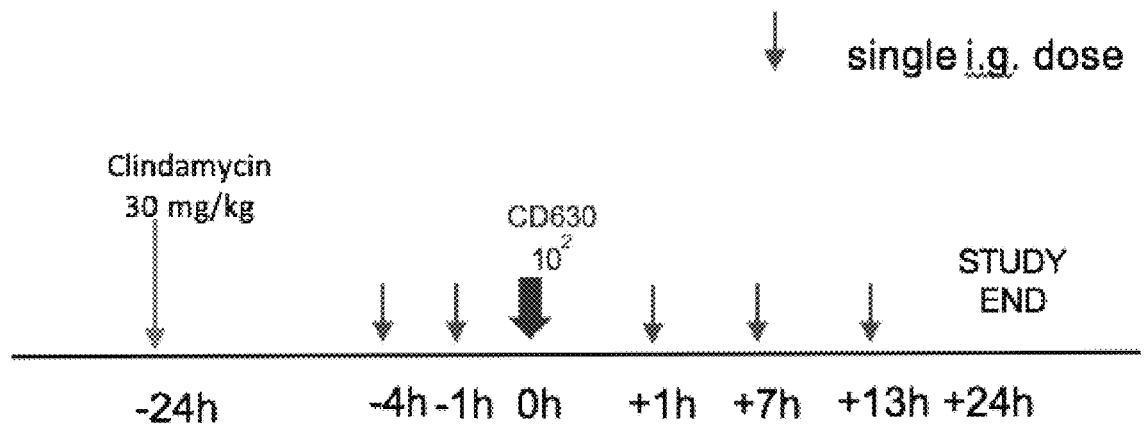

FIG. 32 shows the dosing regimen for studies in mice performed with AmyCidem in lyophilised form.

Figure 33:
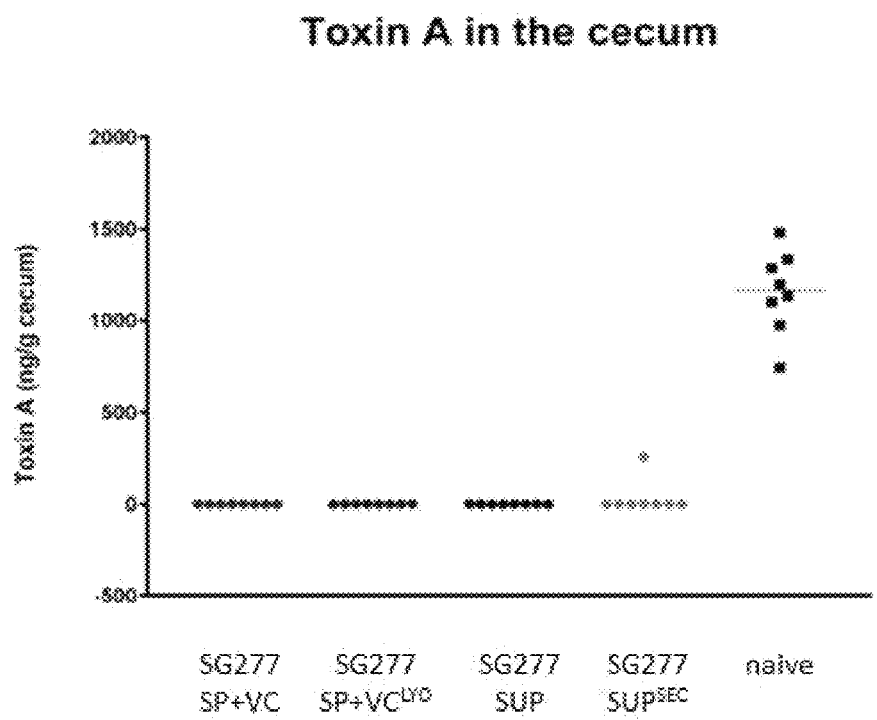

FIG. 33 shows the levels of *C. difficile* toxin A in the cecum in mice at 24 hours. Treatments were: sterile cell-free supernatant of SG277 grown overnight (SUP); SG277 spores and veg cells (SP+VC); lyophilised SG277 spores and veg cells (SP+VC); Crude size exclusion fraction (SUPSEC); PBS buffer (naïve).

Figure 34:
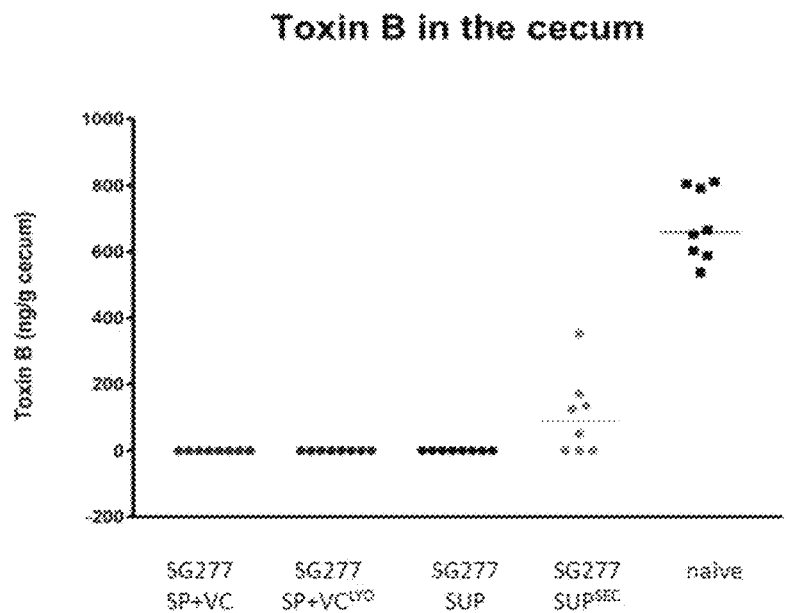

FIG. 34 shows the levels of *C. difficile* toxin B in the cecum in mice at 24 hours.

Figure 35:
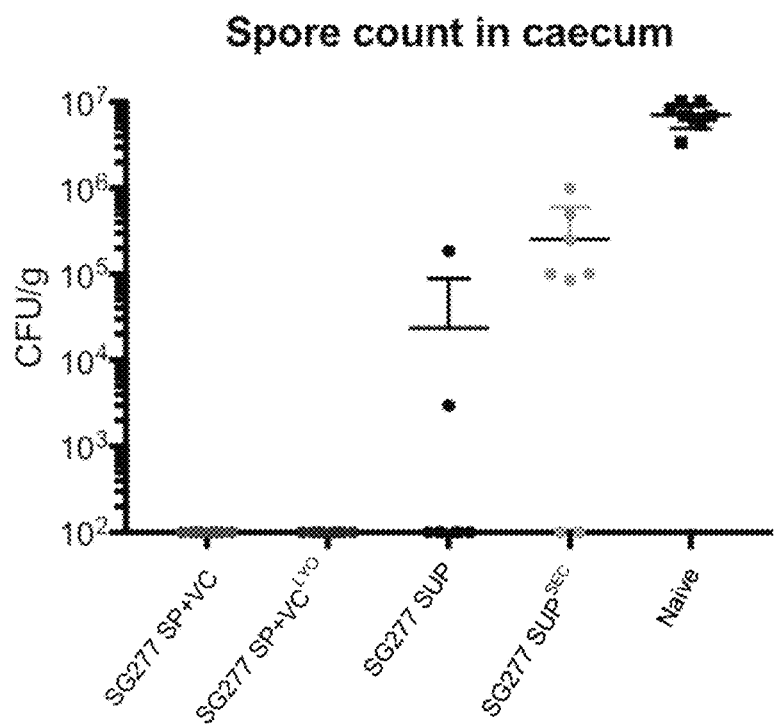

FIG. 35 shows *C. difficile* spore count in the cecum in mice at 24 hours in CFU/g.

Figure 36:
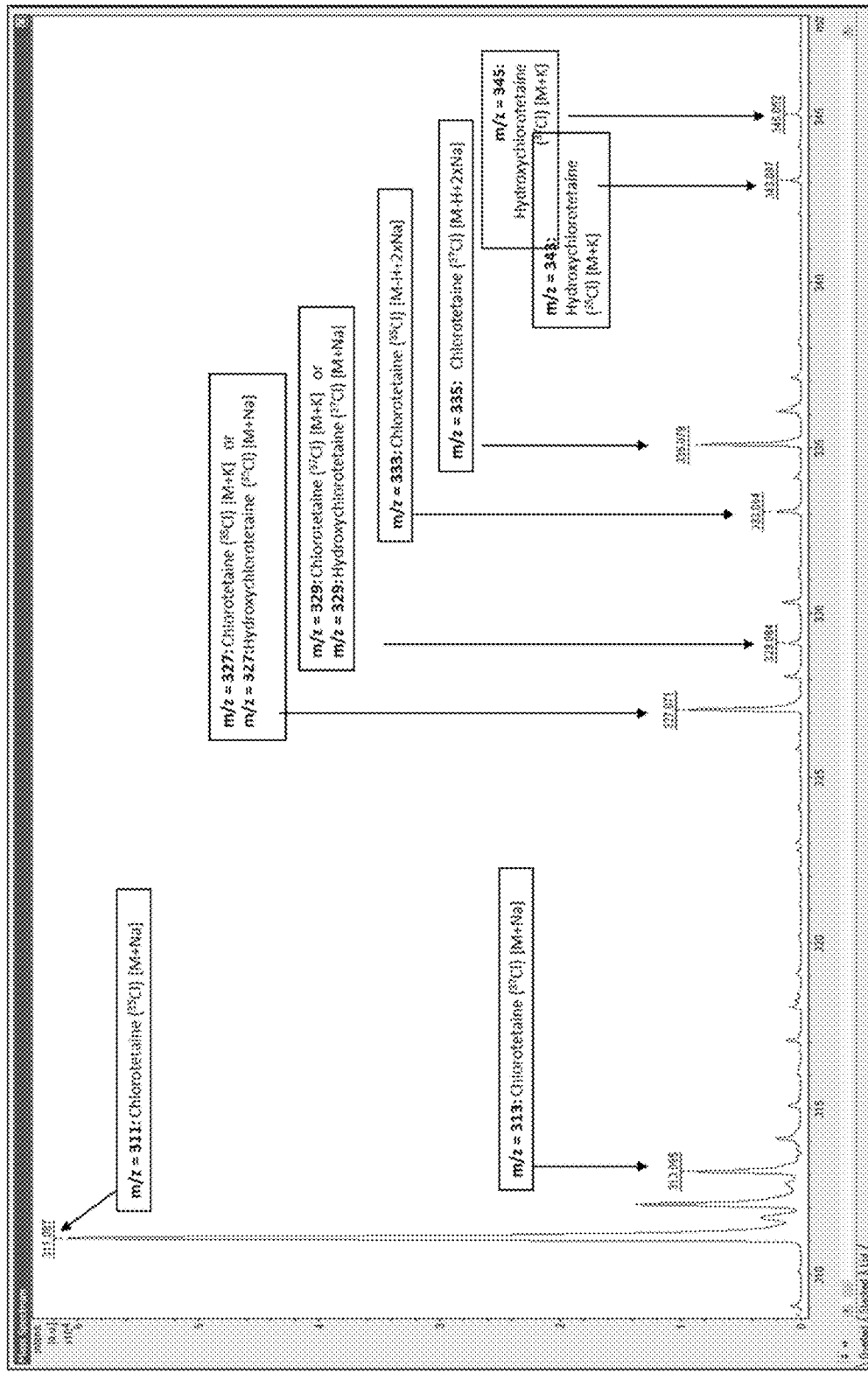

FIG. 36 shows the mass spec profile of 'SEC-HPLC fraction 3'. Identity of peaks together with m/z values are shown.

MATERIALS & METHODS

General Methods

*C. difficile* strains were stored as glycerol stocks and routinely propagated on BHIS agar or medium (Brain heart infusion medium supplemented with 0.1% (w/v) cysteine and 5 mg ml$^{-1}$ yeast extract (76)). All culturing of *C. difficile* was made in an anaerobic chamber (80% $N_2$, 10% $H_2$, 10% $CO_2$; Don Whitley, UK).

Strains

*Clostridium* strains *C. difficile* 630 (erythromycin resistant) was isolated from a patient with pseudomembranous colitis during an outbreak of *C. difficile* infection (CDI) (77). Other strains of *C. difficile* including the hypervirulent strain R20291 and the high toxin producing strain VPI 10463 were laboratory stocks.

*Bacillus* Strains

The following strains were deposited at the NCIMB, Ferguson Building, Craibstone Estate, Bucksburn, Aberdeen, AB219YA on 15 Feb. 2018.

Designation number: NCIMB 42971 Referred to herein as: *B. amyloliquefaciens* SG277

Designation number: NCIMB 42972—Referred to herein as: *B. amyloliquefaciens* SG297

Designation number: NCIMB 42973—Referred to herein as: *B. amyloliquefaciens* SG185

Designation number: NCIMB 42974—Referred to herein as: *B. subtilis* SG140

Growth of *C. difficile* and Preparation of Spores

Spores of *C. difficile* were prepared by growth on SMC agar plates using an anaerobic incubator (Don Whitley, UK) as described previously (36). After growth for seven days at 37° C. spores were harvested and the spore pellet further purified using centrifugation through a 20% to 50% Histodenz gradient (Sigma) as described elsewhere (85). Spore CFU was determined by heat treatment (60° C., 20 min.) and plating on BHISS agar plates (Brain heart infusion agar containing 0.1% (w/v) L-cysteine, 5 mg/ml yeast extract and the spore germinant sodium taurocholate (0.1% w/v).

Characterisation of Intestinal Spore Formers in Mice and Hamsters

C57BL/6 mice (6 weeks, female) housed in groups of 4/cage were dosed with clindamycin (30 mg/kg). Freshly voided faeces was collected 24 h before and after clindamycin treatment and then homogenised in PBS, heat-treated (68° C., 1 h) serially diluted and plated on DSM (Difco sporulation medium; (–86)) or BHI agar supplemented with sodium taurocholate (1 g/L) and L-cysteine (i g/L) a medium used for culture of the human gut microbiota (87). Plates were incubated aerobically or anaerobically at 37° C. for 2 days. 500 colonies were randomly picked and restreaked. The presence of spores in colonies was checked microscopically and each colony was grown for 12 h at 37° C. in liquid culture (2 ml) using aerobic or anaerobic conditions as required before sub-culturing (⅟₁₀₀) overnight in the same conditions. The cell free supernatant was then obtained using centrifugation and filtering through a 0.45 m syringe filter. Activity against CD630 was determined using a microdilution assay (see below). Biosurfactant activity was determined using an oil displacement assay (88). gyrA sequencing used protocols and primers previously described for *Bacillus* (40). Antibiotic minimal inhibitory concentrations (MICs) were made using a microdilution method as stipulated by CLIS (Clinical and Laboratory Standards Institute) (89).

In Vitro Analysis of Anti-*C. difficile* Activity a) Agar Diffusion Assay.

Aerobic *Bacillus* strains were grown in LB medium at 37° C. for 16-18 h while anaerobic spore formers were grown in BHI+cysteine+sodium taurocholate overnight in an anaerobic chamber. Samples were centrifuged (microfuge, 8,000 rpm, 10 min.) and supernatants filter-sterilised (0.45 μm syringe filter) and stored on ice till use. TGY agar plates were pre-reduced and after spreading with an overnight *C. difficile* culture (~100 μl) allowed to dry for 30 min. after which 4-6 wells were cut per plate. TGY medium is, per litre, tryptic soy broth (30 g), glucose (20 g), yeast extract (10 g), L-cysteine (1 g), Resazurin (1 mg) and agar (15 g). Plates were reduced for 4 h in an anaerobic chamber before use. 5 mm diameter wells were cut in the TGY agar plate using a potato borer. 50 μl of *Bacillus* supernatants were applied to labelled wells and the plates incubated at 37° C. for 48 h in an anaerobic chamber and zones of inhibition measured (diameter), typically 9-20 mm.

b) Microdilution Assay

Indicator Culture:

A single colony of the relevant *C. difficile* strain was inoculated into 10 ml of BHIS and incubated overnight at 37° C. in an anaerobic chamber. The overnight culture was then sub-cultured 1:100 into BHIS (typically 0.1 ml into 10 ml BHIS) and incubated at 37° C. for 6 h after which the culture is ready for use.

Plate Set Up:

180 μl of sterile BHIS was pipetted into the first row of a 96-well U-bottom microplate (Sigma CLS3799) and 100 μl into each subsequent row. 20 μl of the sample (sterile-filtered, 0.45 μm) to be tested is pipetted into the first row (1:10 dilution factor) and serially diluted in a 2-fold dilution series until the last row (1:1280 dilution factor) on the microplate. For one serial dilution a 'media only' control is also pipetted into a single well on the first column. 10 μl of the 6 h *C. difficile* 'indicator culture' is pipetted into each well and the plate is incubated overnight at 37° C. in an anaerobic chamber. After overnight growth the microplate contents were agitated on a rotary plate shaker at 200 rpm for 2 min. after which the $OD_{600}$ was read using a microplate plate reader. Positive inhibitory activity was defined as an $OD_{600}<50\%$ of the CD630 control.

c) Co-Culture Assays

*C. difficile* strains were grown in BHIS medium overnight at 37° C. under anaerobic conditions. The following day 5 ml BHIS was inoculated with 0.5 ml of overnight culture and incubated at 37° C. until the optical density reached ~0.2-0.3 $A_{600}$ nm. At this point 1 ml of a freshly prepared (sterile-filtered, 0.45 μm) supernatant was aseptically added to the growing CD cultures and growth resumed.

Preparation of Prophylactic Treatments:

SG277 (or SG297 or SG378) was grown overnight (18 h, 37° C.) in 25 ml BHIB and after centrifugation the pellet suspended in 2 ml of supernatant. For use of the supernatant an aliquot was filter sterilised (0.45 μm). For spores SG277 was grown on DSM (Difco sporulation medium; (85)) agar for 72 h at 37° C. Spore crops were harvested from the plate using a cell scraper, washed three-times in sterile water and then heat-treated to kill residual vegetative cells. Spores were suspended in water to give a concentration of $2.5 \times 10^{10}$ spores/ml.

Mouse Colonisation Experiments:

Animals (C57BL/6, female, aged 6-7 weeks) were dosed i.g. with clindamycin ((clindamycin-2-phosphate, Sigma; 30 mg/kg) and 24 h later challenged with $10^2$ spores of CD630. Animal groups were dosed (0.2 ml, i.g.) with prophylactic treatments before and after challenge with CD630 using the schedule shown in FIG. 1A. Caeca were removed 24 h post-infection for analysis of colonisation (CFU and toxins).

Hamsters:

Golden Syrian Hamsters (female) were 16-18 weeks old (Harlan UK Ltd.). For the hamster challenge, animal groups (n=6) were dosed (i.g.) with clindamycin (30 mg/kg body weight) and then challenged 3 days later with $10^2$ spores of CD630. Before and after CD630 challenge animals were dosed (i.g.; 2 ml/dose) with the treatments described above. The treatment regimen was six doses before CD630 challenge (−48 h, −36 h, −24 h, −12 h, −4 h and −1 h) and then three-times/day post-challenge for 12 days. Animals were monitored for symptoms of disease progression and culled upon reaching the clinical endpoint. The symptoms of CDI were scored as severe/clinical end point (wet tail >2 cm, high lethargy), mild (wet tail <2 cm) or healthy. Caeca were removed and analysed for CD630 CFU and toxins A and B.

Measurement of Correlates of Colonisation

The presence of bacterial CFU and toxins in the faeces and/or caecum provides a measurement of colonisation. For determination of CFU faeces was collected 2-days post-challenge, homogenized in 70% ethanol, incubated overnight, serially diluted in sterile water and plated on ChromID plates (BioMerieux). Plates were incubated anaerobically (37° C.) for 2 days before counting. Toxins A and B were recovered from faecal (collected 24 h post challenge) or caecum samples (from dead animals) at a one-fifth (w/v) dilution in extraction buffer (PBS containing 2% (v/v) fetal calf serum, penicillin-streptomycin (Sigma P4333; 10 ml/L) and Pierce protease inhibitor tablets (Thermo 88265). Samples were homogenised in extraction buffer using wooden sticks and incubated for 2 h at 4° C. The supernatant was harvested after centrifugation (14,000, 5 min.), filtered (0.2 μm) and was used immediately. Faeces was collected 24 h post challenge. Rabbit anti-toxin A and toxin B ('in house' reagents) was used to coat ELISA plates (1/6,000) and left overnight at RT. After this, plates were blocked for 1 h at 37° C. with 2% BSA. Faecal extraction samples were incubated for 2 h at RT. Replicate samples were used together with a negative control (pre-immune faecal extract). Serial dilutions of toxoid A and B were used as a reference. Detection antibodies were mouse anti-toxin A and anti-toxin B (in house reagents; 1/1000) incubated for 1 h at 30° C. HRP-conjugated anti-mouse IgG (Dako; 1/2000) incubated for 1 h at RT. Reactions were developed using TMB substrate and stopped by 2M $H_2SO_4$ and OD read at 450 nm.

Statistical Analysis

Statistical analysis was calculated and significance determined (p<0.05) using Welch's t-test for unequal variance. All statistical analysis was performed using Graphpad Prism software.

PEG Precipitation and CsCl Centrifugation

1 L of a culture in BHIB was grown from a single colony O/N at 37° C. and supernatant collected after centrifugation at 8,000×g for 10 min. The supernatant was then sterile-filtered through a 0.45 μm membrane. Saturated polyethylene glycol (PEG) solution (Sigma, 81260) was added to the sterile supernatant to a final concentration of 8% and incubated for 4 h at 4° C. After incubation, the solution was centrifuged (10,000×g for 30 min. at 4° C.) and the pellet suspended in 10 ml of SM buffer (per litre; NaCl 5.8 g, $MgSO_4 \cdot 7H_2O$ 2 g, 50 mL 1M Tris-HCl pH 7.5). 4 ml of the filtrate was then layered on top of a CsCl gradient consisting of: 4 ml of 1.3 $g/cm^3$ CsCl, 4 ml of 1.4 $g/cm^3$ CsCl and 4 ml of 1.5 $g/cm^3$ CsCl in that order. This gradient was centrifuged in an Optima XPN-90 Ultracentrifuge (Beckman Coulter) with a SW32 rotor (150,000×g, 18 h, 4° C.). Following centrifugation bands were carefully removed using a pipette.

Extraction and Purification of the Active Molecule/s

After cultivating the cells overnight in BHIB broth at 37° C. bacterial cells were removed from the supernatant by centrifugation at 8000×g for 10 min and the supernatant was sterile-filtered through a 0.45 μm membrane. The sterile supernatant (24 ml) was then precipitated with ammonium sulphate (AmSO4) for 4 h at 4° C. using saturated AmSO4 solution (6 ml) giving a final concentration of 20%. Following centrifugation at 8000×g for 15 min the supernatant was removed and the precipitate resuspended in 5 ml PBS. To remove excess AmSO4 the filtrate was dialysed overnight at 4° C. After dialysis, 1 ml of 0.5% (w/v) SDS in PBS was added to the resulting filtrate and 2.5 ml applied to a Superdex 200 column (L×I.D. 30 cm×10 mm) and fractionated by size-exclusion chromatography under denaturing conditions using PBS/0.1% SDS as the running buffer. Fractions were tested for activity against CD630 using a microdilution assay and positive fractions were dialysed overnight at 4° C. to remove remaining SDS. Fractions showing activity were loaded on a uBondapack Phenyl, 125 μm 30 cm×3.9 mm (Waters) and separated by RP-HPLC using Waters 600E system controller with a 600 pump and a ABI Kratos 757 absorbance detector. The mobile phase components were (A) 0.5% acetic acid in 60% (v/v) Methanol and (B) 0.5% (v/v) acetic acid in 95% (v/v) Methanol. The fractions were injected in buffer A and the products were eluted at a flow rate of 0.5 ml/min with a linear gradient of solvent B, developed from 0% to 100% (60 min). The elution pattern was monitored by determining absorbance at 220 nm, and resultant fractions were concentrated using a EZ-2 Genevac centrifugal evaporator and then either testing for activity against CD630 using a microdilution assay or identification using mass spectrometry. For MALDI-TOF analysis the RP-HPLC fractions were premixed with α-Cyano-4-hydroxycinnamic acid matrix solution (Agilent), which was acidified with TFA (0.01% (w/v) final concentration), and spotted on a 384 polished stainless steel MALDI plate (Bruker). MALDI-TOF analysis was conducted using a Bruker autoflex III smartbeam mass spectrometer. The instrument was calibrated to the mass accuracy of at least 30 ppm.

For AmSO4 precipitation, AmSO4 (113 g/L) was added to the sterile filtrate to give a 20% w/v solution and incubated O/N at 40 C. The solution was then centrifuged, and the pellet was suspended in PBS at a concentration of 30× (30 ml of initial culture=1 ml AmSO4 ppt). The AmSO4 ppt was dialysed in PBS O/N (at 40 C) to remove excess AmSO4. Activity of AmSO4 ppt=1/5120. In order to further purify the active species, the AmSO4 precipitate was separated using a Superdex 200 column (10,000 Da-600,000 Da) in PBS+ 0.1% SDS (w/v). This allowed a crude separation of high MW species. SDS was added to denature/linearize unwanted proteins resulting in a purer separation MIC Testing of Compounds Against Mycobacteria The minimal inhibitory concentrations (MICs) of the compounds were determined using resazurin microtitre assay method (REMA). The filter-sterilised supernatant of SG277 was precipitated with ammonium sulphate (20%) and subjected to SEC (size exclusion chromatography). SEC fractions 1-20 were examined for activity to *M. tuberculosis*.

Briefly, serial dilutions of each compound were made between with MB7H9/ADC (BD Biosciences) media in 96-well U-bottom plates. *Mycobacterium tuberculosis* H37Rv and multi-drug resistant *Mycobacterium tuberculosis* (Peru isolate) (MDR-TB) were grown to log phase ($OD_{600}$=1.0) and $10^4$ cells were added to all wells. The plates were thereafter incubated at 37° C. in 5% $CO_2$ for 10 days. The plates were internally controlled using standardised serial dilutions of first line TB drugs isoniazid (INH) and rifampicin (RIF) at a concentration range of 4, 2, 1, 0.5, 0.25, 0.125, 0.063 μg/ml, in addition to negative (only media) controls. The MICs were determined as the first dilution to show complete growth inhibition. This was determined visually by recording the colour change observed.

In Vitro Testing Activity Against *Staphylococcus aureus*

Sterile filtrates of extracellular material produced by *Bacillus* strains were made by growing overnight (18 h) cultures of each strain in BHIB (Brain heart infusion broth) at 37° C. (250 ml Bellco flasks). Cultures were centrifuged (9000×g, 20 min.) and the supernatant filter-sterilised (0.45 µm). Filtrates were kept on ice until use and used within 5 h.

*S. aureus* cultures are prepared fresh from single colonies by growth in 25 ml LB medium at 37° C. (in 250 ml flasks). When cultures have reached an approx. OD600 of 1.0 200 µl of each culture was plated on dry LB agar plates, (2-4 plates per culture). After the inoculum had dried a sterile potato borer (or similar) was used to excise 5 mm circular wells in plates (4-5 holes per plate). 100 µl of sterile extracellular filtrate was added to wells, plates were then incubated (plates up, not inverted) at 37° C. for 2 days and zones of inhibition read after 1 or 2 days (diameter of zone of inhibition, or radius). Each plate would carry a control (sterile PBS or water) and duplicates used for each test strain.

In Vivo Testing Activity Against *Staphylococcus aureus*

On the same day the *S. aureus* strain was used to inoculate LB medium. Cultures were grown at 37° C. until mid-log phase of growth (~0.2-0.8 OD600). The culture was then split and to one flask sterile extracellular filtrate (1/10 diln.) were added. Growth was maintained at 37° C. and OD600 readings taken hourly (FIG. 29).

Testing Activity Against *Vibrio harveyi* and *Vibrio parahemolyticus*

Strains

SG527 *V. harveyi* 16.6
SG528 *V. harveyi* 27.4
SG529 *V. parahemolyticus*
SG530 *V. parahemolyticus*

*V. harveyi* SG527 was grown in LB+2% NaCl overnight at 28° C. The following day 1/500 dilution was subcultured into fresh LB+2% NaCl and incubated at 28° C. in a shaking water bath at 200 rpm. The Optical Density (600 nm) and viable counts were measured every hour. Once the OD reached 0.6 the culture was split into two parts and the filter-sterile culture supernatant of SG277 was added to give a final concentration of 1/10 and OD measurements taken thereafter.

*V. parahemolyticus* SG529 was grown in LB+2% NaCl overnight at 28° C. The following day 1/500 dilution was subcultured into fresh LB+2% NaCl and incubated at 28° C. in a shaking water bath at 200 rpm. The Optical Density (600 nm) and viable counts were measured every hour. Once the OD reached 0.481 the culture was split into two parts and filter sterile culture supernatant of SG277 was added to the final concentration of 1/10 and OD measurements taken thereafter.

Testing the Stability of AmyCide™ in Lypohilised Form

SG277 was prepared (o/n growth at 37° C. in BHIB) and the bacteria centrifuged and one portion lyophilised. Portions of wet material and lyophilised material were stored at RT, 4° C. and frozen and aliquots taken for analysis of anti-*C. difficile* activity using a microplate assay.

Testing the Stability of AmyCidem in Lypholised Form

Groups of mice (n=8/gp) were dosed (oral, intra-gastric (i.g.), i.g., 0.2 ml/dose) with different forms of test material. The regimen used is shown below with the 1st oral administration of material 4 h before challenge with CD630 (*C. difficile* strain 630; 100 spores). Animals were housed individually in IVCs (independently ventilated cages). The basic animal model of CDI was the 'colonisation model' in which symptoms of CDI do not develop but colonisation is indicated by the presence of *C. difficile* toxins and bacterial cfu in the cecum or faeces [3-5].

Animal Groups

Gp.1. SG277 SP+VC

Cells of SG277 were grown for 16 h at 37° C. in 25 ml BHIB (brain heart infusion broth). The cells were harvested from 100 ml culture (4 flasks) and the pellet resuspended in 2 ml of PBS. 1 dose=0.2 ml and ~$5 \times 10^9$ CFU consisting of spores (~70-100%).

Gp.2. Freeze-Dried SG277 SP+VC (SG277 SP+VC$^{LYO}$)

Cells of SG277 were grown for 16 h at 37° C. in 25 ml BHIB. The cell pellet was then frozen and lyophilized o/n. On the day of use, material was resuspended in 2 ml of PBS. 1 dose=0.2 ml and ~$5 \times 10^9$ CFU consisting of spores (~70-100%).

Gp.3. SG277 SUP

SG277 was grown overnight at 37° C. in BHIB. After 18 h the cells removed by centrifugation and supernatant (SUP) sterilised by filtration through a 0.45 µm filter. Stored at −20° C. till use. 1 dose=0.2 ml.

Gp.4. SG277 SEC Fraction (SG277 SUPSEC)

The SG277 sterile supernatant was precipitated with 20% ammonium sulphate and purified by size-exclusion chromatography (SEC) and fractions carrying anti-CD630 activity pooled (determined using an in vitro microdilution assay). Sample aliquots were stored at −20° C. and thawed on the day of use. 1 dose=0.2 ml. Gp.5. Naive 1 dose=0.2 ml of PBS.

Results

Example 1: Intestinal Aerobic Spore-Forming Bacteria, Rather than Anaerobic Spore Formers, Inhibit *C. difficile*

10 days before the start of the experiment, C57BL/6 mice were kept in independently ventilated cages (IVCs) with autoclaved water, UV treated food and sterile bedding. Cages were changed every day. Faecal samples were taken from mice before and after treatment with clindamycin. Clindamycin, administered by intra-gastric (i.g.) gavage, was used at a concentration (30 mg/kg) sufficient to induce CDI but here the animals were not challenged with *C. difficile*. Homogenised faeces were heat-treated to kill vegetative cells and serial dilutions made on agar plates, which were incubated aerobically or anaerobically. Resultant colonies would arise from heat-resistant spores that had germinated and a total of 500 colonies from the aerobic or anaerobic plates were colony purified for further analysis.

First, the inventors determined the number of colonies that inhibited growth of *C. difficile* strain 630 (CD63 using an agar-diffusion assay that measured activity from a cell-free supernatant of the cultured bacterium, and the results are given in Table 1.

TABLE 1

Intestinal spore formers pre- and post-clindamycin treatment from mouse faeces

| | Pre-clindamycin | | | Post-clindamycin | | |
|---|---|---|---|---|---|---|
| Spores[a] | No. isolated | No. anti-CD activity[b] | % | No. isolated | No. anti-CD activity[b] | % |
| aerobic Spore formers | 500 | 40 | 8 | 500 | 4 | 0.8 |
| anaerobic Spore formers | 500 | 0 | 0 | 500 | 0 | 0 |

[a]spores isolated by aerobic or anaerobic incubation of heat-treated faeces.
[b]activity against CD630 using a well-diffusion assay of sterile cell free supernatants from colony cultures.

Surprisingly, the inventors found no anaerobic isolates either before or after clindamycin treatment able to inhibit CD63. On the other hand, 8% of the aerobic, spore-forming, isolates (n=40) carried anti-*C. difficile* activity in the extracellular material but, after clindamycin treatment, the percentage of isolates carrying anti-*C. difficile* activity had reduced to 0.8% (n=4). Interestingly, the inventors could not detect *Bacillus* species in mouse faecal samples using 16S metagenomic sequencing. This probably indicates that faecal samples may mostly contain only *Bacillus* spores but not vegetative cells in agreement with a recent murine study (39)

Next, the inventors characterized the aerobic isolates that carried anti-*C. difficile* activity, and the results are shown in Table 2.

TABLE 2

Phenotype of aerobic spore formers with activity against *C. difficile* isolated from mouse faeces[a]

| Bacillus species | Phenotype[b] | # Pre-Clindamycin | # Post-Clindamycin |
|---|---|---|---|
| B. amyloliquefaciens | Clin[R] BS[+] | 0 | 0 |
| | Clin[R] BS[−] | 0 | 0 |
| | Clin[S] BS[+] | 19 | 3 |
| | Clin[S] BS[−] | 0 | 0 |
| B. subtilis | Clin[R] BS[+] | 0 | 0 |
| | Clin[R] BS[−] | 0 | 0 |
| | Clin[S] BS[+] | 10 | 0 |
| | Clin[S] BS[−] | 0 | 0 |
| B. licheniformis | Clin[R] BS[+] | 0 | 0 |
| | Clin[R] BS[−] | 11 | 1 |
| | Clin[S] BS[+] | 0 | 0 |
| | Clin[S] BS[−] | 0 | 0 |

[a]spores isolated by aerobic or anaerobic incubation of heat-treated faeces
[b]Clin[R] = clindamycin resistant, Clin[S], clindamycin sensitive, BS[+], biosurfactant activity, BS[−], no biosurfactant activity. Resistance to clindamycin was determined using a microdilution assay with resistance defined as an MIC of >4 mg/L (83).

Using gyrA sequencing, which is more informative than 16S rRNA sequencing (40), the inventors demonstrated that only three *Bacillus* species were present, *B. amyloliquefaciens* (n=22), *B. subtilis* (n=10) and *B. licheniformis* (n=12). Using an assay for biosurfactant activity the inventors demonstrated that the *B. amyloliquefaciens* (n=22) and *B. subtilis* (n=10) isolates all carried biosurfactant activity in their cell-free supernatants, were mucoid and sensitive to clindamycin, see Table 2. However, the *B. licheniformis* isolates (n=12) were all resistant to clindamycin and did not carry biosurfactant activity.

The inventors also conducted a similar study using hamsters (Golden Syrian), as shown in Table 3, and observed a similar phenomenon with 26% of aerobic spore formers carrying activity against *C. difficile* and this being reduced to 1% post-clindamycin treatment.

TABLE 3

Intestinal spore formers pre- and post-clindamycin treatment from hamster faeces

| | Pre-clindamycin | | | Post-clindamycin | | |
|---|---|---|---|---|---|---|
| Spores[a] | No. isolated | No. anti-CD activity[b] | % | No. isolated | No. anti-CD activity[b] | % |
| aerobic Spore formers | 100 | 26 | 26 | 100 | 11 | 11 |
| anaerobic Spore formers | 100 | 0 | 0 | 0 | 0 | 0 |

[a]spores isolated by aerobic or anaerobic incubation of heat-treated faeces.
[b]activity against CD630 using a well-diffusion assay of sterile cell free supernatants from colony cultures.

Figure 1:
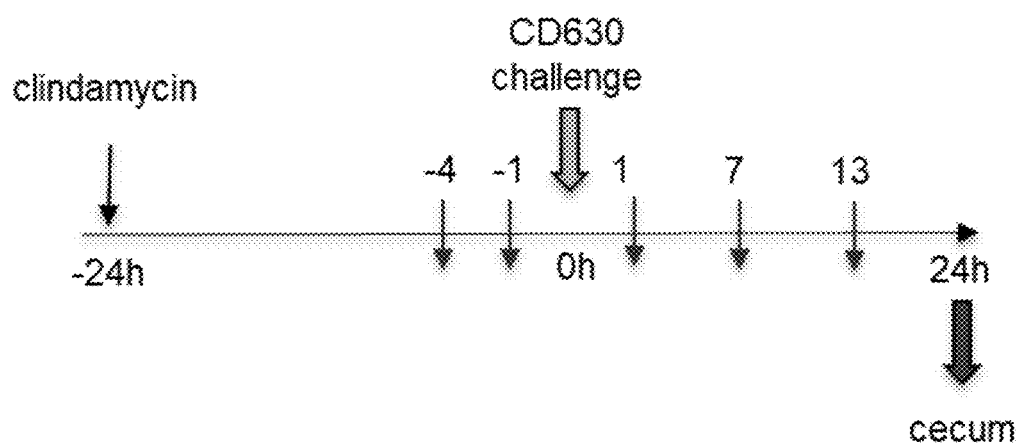
Figure 1:
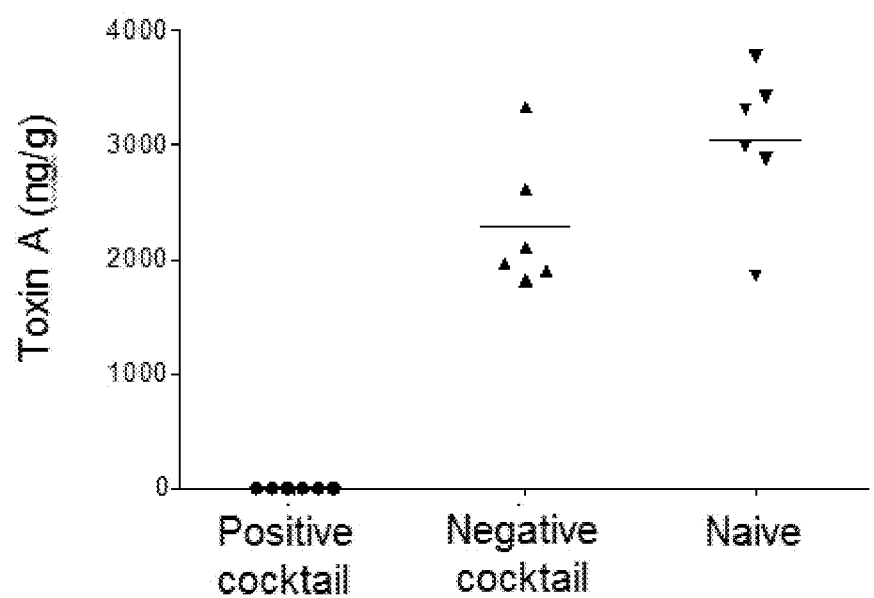
Figure 1:
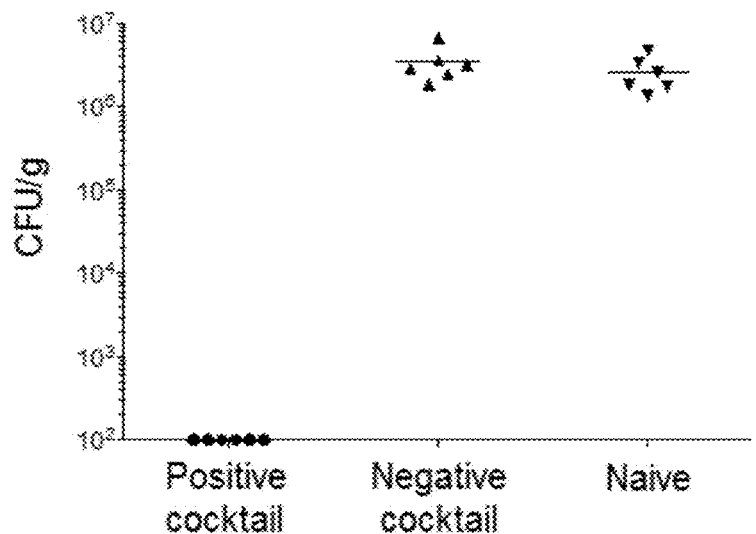

Example 2: *Bacillus* Spore-Formers Isolated from the Murine GI-Tract with In Vitro Activity Against *C. difficile* Inhibit CDI In Vivo To determine whether in vitro activity to *C. difficile* could translate to inhibition in vivo, the inventors dosed (intragastric, i.g.) two groups of mice (n=4) with suspensions of bacteria isolated from the pre-clindamycin faecal samples shown in Table 1. Group 1 were dosed with a mixture of three *Bacillus* species (*B. amyloliquefaciens, B. subtilis* and *B. licheniformis*) that showed activity against *C. difficile* while Group 2 were dosed with three *Bacillus* isolates (one isolate each of *B. amyloliquefaciens, B. subtilis* and *B. licheniformis*) that showed no in vitro activity against *C. difficile*. For each group the oral dose comprised a total of $3 \times 10^9$ bacteria consisting of $1 \times 10^9$ bacteria from each isolate tested. A third group consisted of naïve animals dosed only with PBS. As shown in FIG. 1A, mice were dosed first with clindamycin (i.g.; 30 mg/kg) and then given five doses of the bacterial suspensions or PBS. After the second dose, mice were challenged with $10^2$ spores of *C. difficile* strain 630. One day later, all animals were sacrificed and caecum samples taken.

All animals in Group 1 showed no evidence of CDI as shown from the absence of toxin A or *C. difficile* CFU in caecum samples, see FIGS. 1B and 1C, respectively. By contrast, animals dosed with Bacilli showing no in vitro activity against *C. difficile* exhibited clear signs of *C. difficile* colonisation, i.e., high levels of toxin A and *C. difficile* CFU equivalent to naïve mice, see FIGS. 1B and 1C, respectively.

Example 3: The Intestinal Cohort of Aerobic Spore Formers Represents an Allochthonous Population The inventors housed groups of mice in either conventional cages (CCs) or independently ventilated cages (IVCs) using three animals per cage. IVCs carry HEPA-filtration and prevent exposure of animals to airborne bacteria. Animals received sterile food and water together with regular changes of sterile bedding. Every ten days faeces was examined for the presence of aerobic bacteria including total and heat-resistant (representing bacterial spores) CFU following aerobic incubation.

As shown in FIG. 2A, over time, the number of aerobic bacteria identified in faecal samples remained constant at about $10^5$-$10^6$ CFU/g. The level of spores ($10^3$-$10^4$/g) in faeces closely matched the predicted concentration in human faeces (24). Remarkably, for animals housed in IVCs, spore counts showed a marked temporal reduction and after 40 days no spores could be detected (n.b., $10^2$ CFU is at the limit of detection), see FIG. 2B. This decline in aerobic spore counts was not observed in mice housed in conventional cages implying that the aerobic population of spore formers was allochthonous and had been acquired from the environment.

Figure 3:
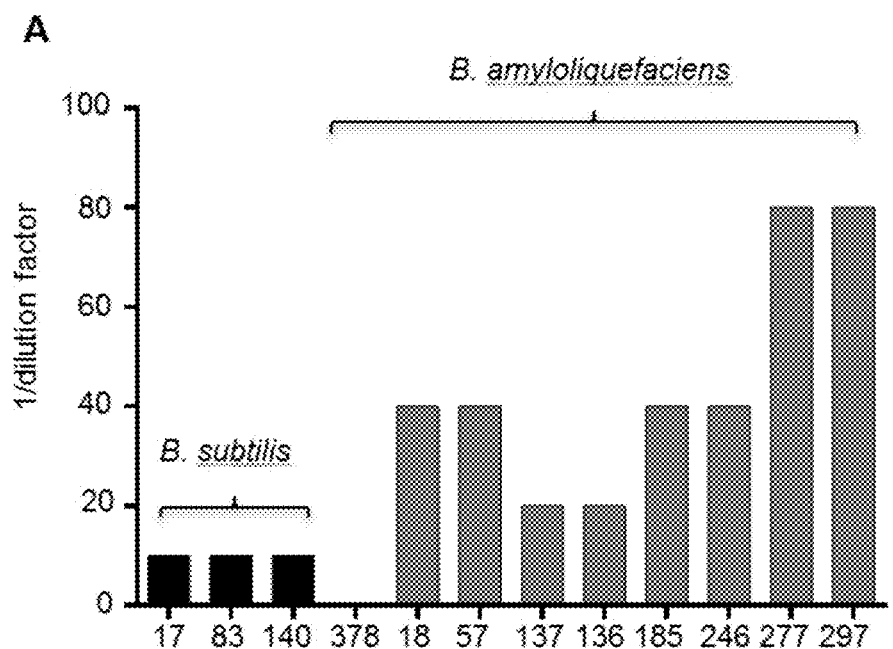
Figure 3:
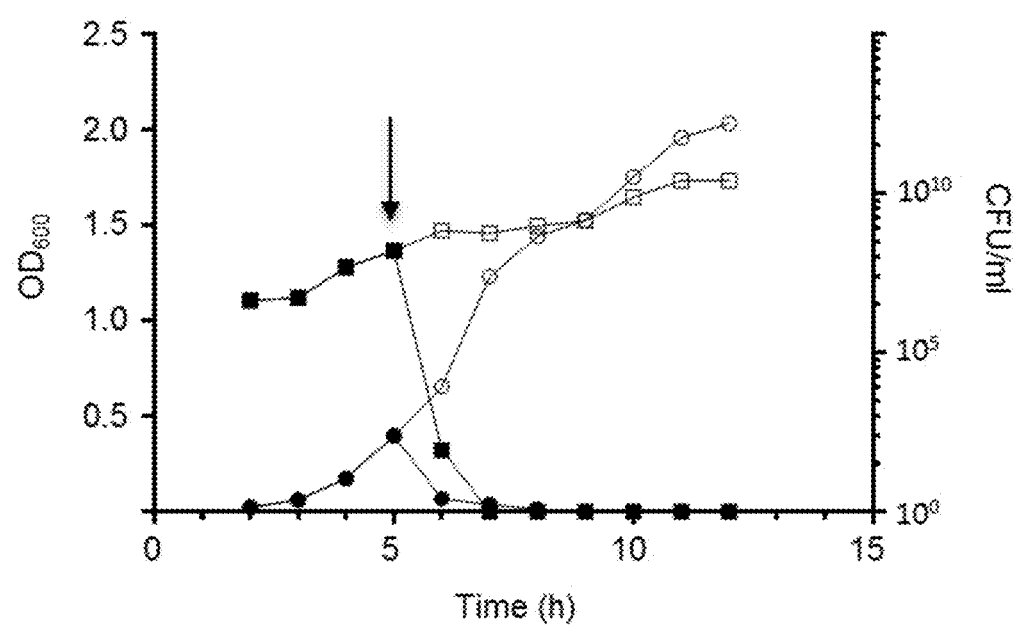

Example 4: Human Isolates of *B. amyloliquefaciens* and *B. subtilis* that have Anti-*C. difficile* Activity The inventors have previously characterised *Bacillus* species isolated from human faeces (19). From their collection of human isolates, they screened for strains that carried extracellular activity against *C. difficile* (CD630) using an agar-diffusion assay. They were able to identify a number of *B. subtilis* and *B. amyloliquefaciens* strains that carried potent activity and, using a more robust microdilution assay, quantified the level of extracellular inhibitory activity, see FIG. 3A. All strains carried biosurfactant activity and were clindamycin sensitive. Colonies of these isolates were noticeably mucoid and particularly so with *B. amyloliquefaciens*. All strains produced robust and extensive biofilms, a characteristic of some Bacilli but notably undomesticated strains (19, 41).

*B. amyloliquefaciens* strains SG277 and SG297 that demonstrated the highest levels of inhibitory activity were studied further. Using a co-culture assay the inventors added sterile supernatants of SG277 or SG297 to logarithmic cultures of different *C. difficile* strains which revealed a clear bactericidal effect resulting in rapid and complete lysis of the *C. difficile* cultures, see FIG. 3B which shows SG277-mediated lysis of CD630.

*C. difficile* cultures were grown in BHIS for 10 h at 37° C. 180p of the *C. difficile* culture was added to a microplate well followed by 20 µl of a sterile SG277 filtrate. Plates were incubated anaerobically 18 h at 37° C. after which the $OD_{600}$ was read. A SG277 sterile filtrate was also incubated overnight as a control and showed no growth. As shown in Table 4, the inventors showed that the SG277 filtrate had activity against a large number of different *C. difficile* ribotypes.

TABLE 4

Activity against different *C. difficile* ribotypes[a]

| C. difficile strain | Ribotype | $OD_{600}$ Untreated | $OD_{600}$ +SG277 | % inhibition |
|---|---|---|---|---|
| CD630 | RT012 | 0.756 | 0.059 | 92 |
| SH1 | RT078 | 0.845 | 0.086 | 90 |
| SH101 | RT115 | 0.772 | 0.081 | 89.5 |
| SH102 | RT176 | 0.981 | 0.072 | 93 |
| R20291 | RT027 | 0.857 | 0.091 | 89 |
| CD196 | RT027 | 0.798 | 0.056 | 93 |
| SH104 | RT023 | 0.534 | 0.056 | 89.5 |
| VPI 10463 | RT087 | 0.687 | 0.054 | 92 |
| CD10 | non-tox | 0.824 | 0.102 | 88 |
| SH242 | RT111 | 0.672 | 0.089 | 87 |
| SH200 | RT056 | 0.914 | 0.076 | 92 |
| SH203 | RT038 | 0.882 | 0.064 | 93 |
| SH218 | RT001 | 0.732 | 0.081 | 89 |
| SH210 | RT002 | 0.655 | 0.055 | 92 |
| SH213 | RT014 | 0.758 | 0.064 | 92 |
| SH215 | RT54 | 1.025 | 0.056 | 95 |
| SH220 | RT336 | 0.783 | 0.049 | 94 |
| SH222 | RT401 | 0.952 | 0.082 | 91 |

TABLE 4-continued

Activity against different *C. difficile* ribotypes[a]

| C. difficile strain | Ribotype | $OD_{600}$ Untreated | $OD_{600}$ +SG277 | % inhibition |
|---|---|---|---|---|
| SH231 | RT56 | 0.791 | 0.073 | 91 |
| SH236 | RT005 | 0.883 | 0.091 | 90 |
| SH239 | RT103 | 0.966 | 0.086 | 91 |
| SH103 | RT075 | 0.761 | 0.106 | 86 |
| SH3 | RT017 | 0.692 | 0.055 | 92 |
| SH1 | RT005 | 0.883 | 0.091 | 90 |

The extracellular activity of SG277 and SG297 supernatants was characterised using a microdilution assay to measure inhibitory activity against CD strain 630. Bacillus supernatants were filter-sterilised (0.45 µm) exposed to various treatment conditions. The highest dilution factor that showed inhibitory activity for the treated sample is shown in Table 5. All assays were conducted on the same day and with the same filtrate.

The various treatment conditions were:

Heat—filtrates (0.5 ml) were incubated in an oven at the selected temperature for 30 min. and allowed to cool to RT before assay.

Autoclaving—filtrates were autoclaved at 121° C. and 20 psi for 20 min.

Simulated gastric fluid (SGF)—three solutions at pH, 2, 3 and 4 were made using HCl to adjust pH. Supernatants (0.5 ml) were incubated with an equal volume of SGF (0.2% w/v NaCl, 3.5 mg/ml pepsin) and incubated for 1 h at 37° C. before assay.

Enzymes—supernatants (0.5 ml) were incubated with the following enzymes (all from Sigma) at 1 µg/ml final concentration for 1 h at 37° C. before assay, lysozyme (L7651), lipase (L3126), amylase (A3176). For the proteases, pronase (P5147), trypsin (T8003) and proteinase K (Thermo Scientific E00491) the final concentration of enzyme was 1 mg/ml.

Solvents—filtrate (0.5 ml) was vortexed for 1 min. with 0.5 ml of solvent.

0.1M NaOH or 0.1% SDS—filtrates (0.5 ml) were combined with 0.5 ml solutions of 0.2M NaOH or 0.2% (w/v) SDS, to give samples comprising 0.1M NaOH or 0.1% (w/v) SDS and incubated overnight at 37° C.

0.1%-1.0% glutaraldehyde—filtrates (0.5 ml) were combined with 0.5 ml solutions of solutions (v/v) of 0.2%, 0.5%, 1.0% or 2.0% glutaraldehyde neutralised with glycine at a molar ration of 1:10 to give samples comprising of 0.1%, 0.25%, 0.5% or 1.0% (v/v) glutaraldehyde and incubated for 2 h at 37° C.

TABLE 5

Characterization of Extracellular Activity

| Treatment | | SG277 filtrate | SG297 filtrate |
|---|---|---|---|
| No treatment | | 1/80 | 1/80 |
| Heat | 60° C. | 1/80 | 1/80 |
| | 70° C. | 1/80 | 1/80 |
| | 80° C. | 1/80 | 1/80 |
| | 90° C. | 1/40 | 1/80 |
| | 100° C. | 1/40 | 1/40 |

TABLE 5-continued

Characterization of Extracellular Activity

| Treatment | | SG277 filtrate | SG297 filtrate |
|---|---|---|---|
| Autoclaving | | 0 | 0 |
| SGF | pH2 | 1/40 | 1/40 |
| | pH3 | 1/40 | 1/40 |
| | pH4 | 1/40 | 1/40 |
| Enzymes | Lysozyme | 1/80 | 1/160 |
| | Lipase | 1/80 | 1/80 |
| | Amylase | 1/80 | 1/160 |
| | Pronase | 1/80 | 1/80 |
| | Trypsin | 1/80 | 1/80 |
| | Proteinase K | 1/80 | 1/160 |
| Solvents | toluene | 1/80 | 1/80 |
| | chloroform | 1/80 | 1/80 |
| | acetone | 1/40 | 1/80 |
| 0.1 M NaOH | | 1/40 | 1/80 |
| 0.1% SDS | | 1/40 | 1/80 |
| 0.1% glutaraldehyde | | 1/40 | 1/40 |
| 0.25% glutaraldehyde | | 1/40 | 1/40 |
| 0.5% glutaraldehyde | | 1/40 | 1/40 |
| 1% glutaraldehyde | | 1/40 | 1/40 |

As shown in Table 5, the cell free activity of SG277 and SG297 supernatants was shown to be resistant to a number of treatments including organic solvents, proteases, simulated gastric fluid (SGF) and notably heat with partial resistance to 100° C.

Figure 4A:
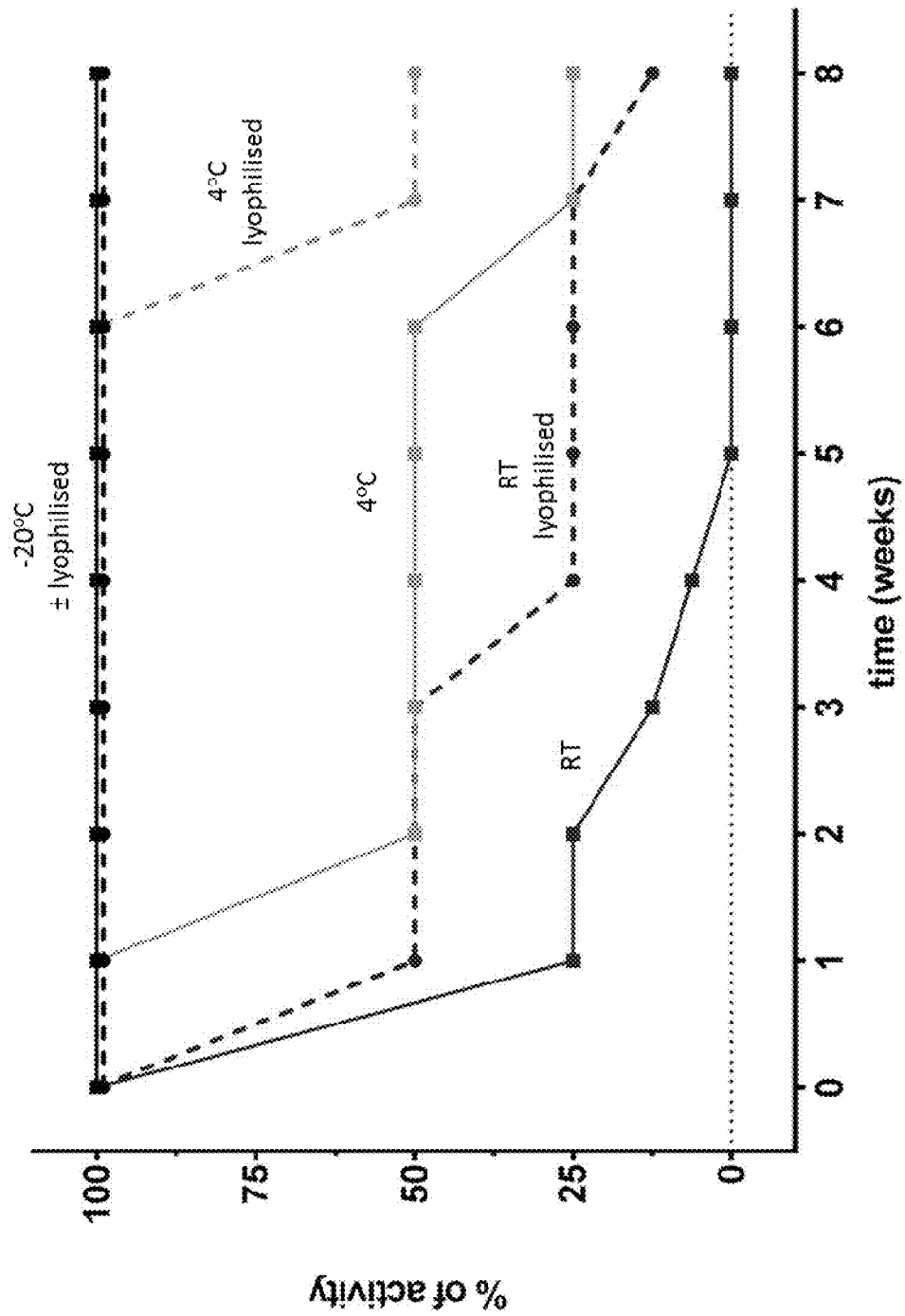
Figure 4:
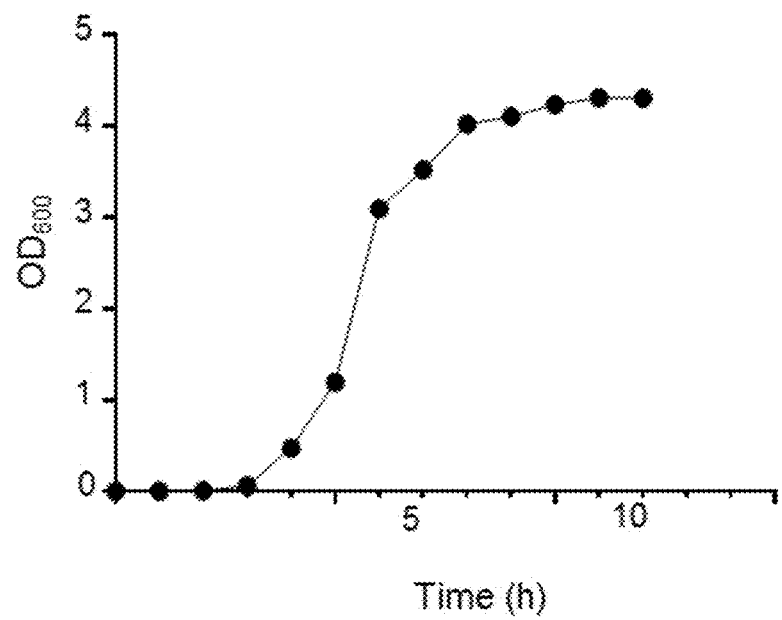
Figure 4:
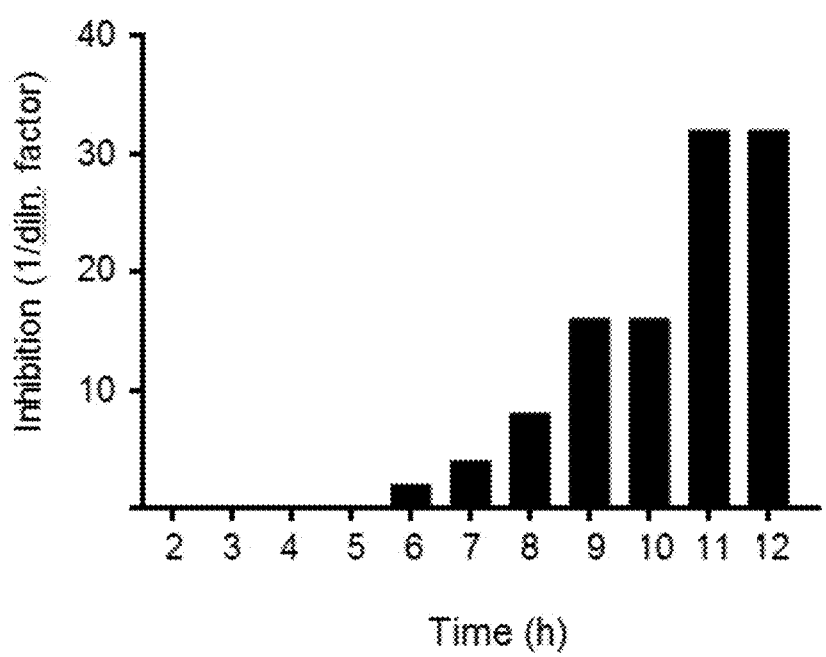

Furthermore, the stability of the SG277 sterile supernatant was measured over 50 days and, as shown in FIG. 4A, 40% stability was retained after 45 days storage at 4° C. As shown in FIGS. 4B and 4C, in growing cultures, activity against *C. difficile* developed during stationary phase, suggesting that it was a secondary metabolite, and thus an antibiotic.

SG277 cells when repeatedly washed, then mixed (1:1) with CD630 and applied to a semi-soft agar and, when incubated anaerobically overnight, revealed clear lysis of the bacterial lawn, see FIG. 5B. Conversely, FIG. 5A shows a control plate where no SG277 cells were applied to CD630 and a lawn of profuse CD630 growth was apparent. SG277 and indeed all *B. amyloliquefaciens* and *B. subtilis* isolates described here were facultative aerobes demonstrating that activity most probably arose from the cell envelope. Finally, and surprisingly, the inventors killed SG277 cells by heat treatment (80° C., 30 min.) and confirmed that cells could still lyse *C. difficile*. This shows that activity against *C. difficile* while present in the cell free supernatant was also present on the cell surface. The inventors, therefore, believe that the bacteria can be used in a killed form (e.g. by heating, gamma irradiation, autoclaving etc). The results are shown in Table 6 below.

TABLE 6

Results of CD630 applied to agar with additional treatments

| CD630 Treatment | Plate Lysis |
|---|---|
| Untreated | − |
| +SG277 supernatant | + |
| +SG277 supernatant (80° C.) | + |
| +SG277 washed cells | + |
| +SG277 washed cells (80° C.) | + |

Figure 5:
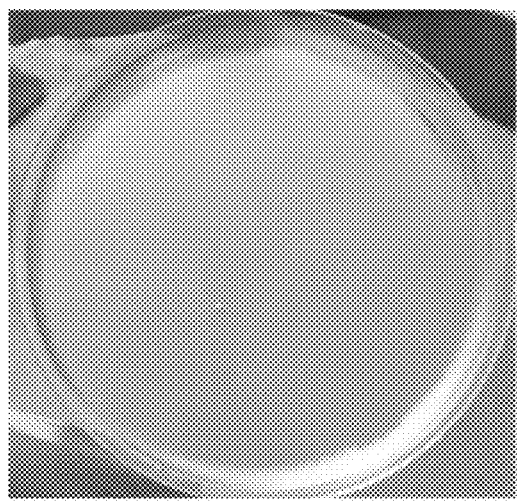
Figure 5:
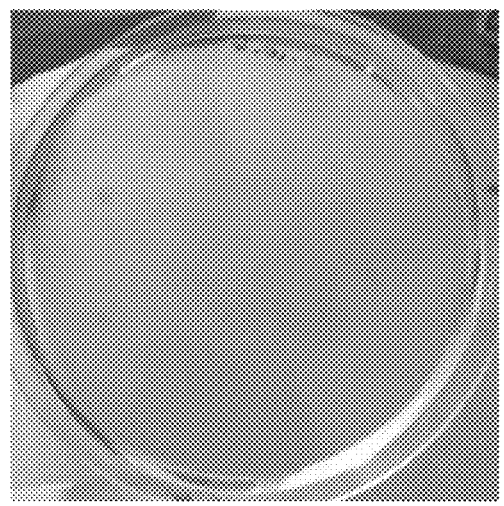

+, lysis of CD630 lawn,
−, no lysis of CD630 lawn, i.e., profuse growth (ref to FIG. 5)

The activity of SG277 and SG297 sterile filtrates were assessed for their spectrum of activity against a range of Gram-positive and Gram-negative bacteria, as shown in Table 7. Activity was determined using an agar-diffusion method. SG247 is a strain of *B. amyloliquefaciens* shown not to have activity against *C. difficile* and was used as a control.

TABLE 7

Antimicrobial Spectrum of *B. amyloliquefaciens* extracellular activity

| Species | Strains | SG247 | SG277 | SG297 |
|---|---|---|---|---|
| Gram-positives | | | | |
| Bacillus anthracis Sterne | DL1090[b] | − | + | + |
| Bacillus pumilus | SF216 | − | + | + |
| Bacillus subtilis | PY79 | − | +/− | + |
| Bacillus clausii | SF150 | − | + | + |
| Bacillus cereus | GN105 | − | + | + |
| Bacillus megaterium | QMB1551 | − | +++ | +++ |
| Bacillus firmus | SF203 | − | +++ | +++ |
| Bacillus aquimaris | SF222 | − | ++ | ++ |
| Listeria monocytogenes | ATCC 7644 | − | ++ | ++ |
| Staphylococcus aureus | ATCC 6538 | − | +/− | + |
| Staphylococcus epidermidis | ATCC 12228 | − | +++ | +++ |
| Enterococcus fecalis | ATCC 29212 | − | ++ | ++ |
| Lactobacillus rhamnosus | GG | − | ++ | +++ |
| Lactobacillus fermentum | DRL38 | − | ++ | +++ |
| Lactobacillus mucosae | SF1146 | − | − | ++ |
| Mycobacterium smegmatis | mc2 155 | − | +/− | + |
| Gram-negatives | | | | |
| Pseudomonas aeruginosa | NCTC 12903 | − | ++ | ++ |
| Vibrio harveyi | SG528 | − | +(1/32)[b] | +(1/32)[b] |
| Vibrio parahemolyticus | SG530[c] | − | +(1/8)[b] | +(1/8)[b] |

[a], Activity was determined using an agar-diffusion method. + = 1-3 mm; ++ = 4-5 mm; +++ > 5 mm
[b]activity against these strains was bacteriostatic and inhibition was demonstrated using a microdilution assay and the highest dilution factor required to inhibit growth is shown in brackets.

Activity is represented by "+"=1-3 mm; "++"=4-5 mm; and "+++">5 mm. Activity of *Pseudomonas aeruginosa*, *V. harveyi* and *V. parahemolyticus* was bacteriostatic and inhibition was demonstrated using a microdilution assay and the highest dilution factor required to inhibit growth is shown in brackets.

Activity was found against Gram-positives, including a number of important pathogens, *Bacillus anthracis*, *Listeria monocytogenes* and *Staphylococcus aureus*. With a number of exceptions the inventors did not observe much activity against Gram-negatives. Those exceptions all exhibited bacteriostatic rather than bacteriocidal inhibition. It is of course possible that both SG277 and SG297 produce other antimicrobials that can inhibit growth but it is worthwhile noting that the strains that showed inhibition included a number of important pathogens (*V. harveyi*, *V. parahemolyticus* and *P. aeruginosa*).

In conclusion, the inventors show that isolates of *B. subtilis* and *B. amyloliquefaciens* have the potential to produce a potent biosurfactant that is associated with the cell surface. The inventors refer to this biosurfactant as "Amy-Cidem".

Example 5: Inhibition of CDI In Vivo

The inventors used mouse and hamsters to determine whether the biosurfactant, AmyCide™, could prevent CDI using SG277 as an exemplar. The inventors considered a number of different administrations. First, use of the sterile, cell-free supernatant (SUP), second, a suspension of spores (SPORES), and finally a suspension of an SG277 culture either (i) washed and suspended in PBS (277-PBS), or (ii) suspended in the supernatant (277-SUP). For the latter approach, the inventors used overnight cultures of SG277 that were found to contain a mixture of vegetative cells and spores. Controls were provided by an overnight culture of SG378 suspended in their sterile cell-free supernatant (378) and by using a PBS buffer (naïve).

Figure 6A:
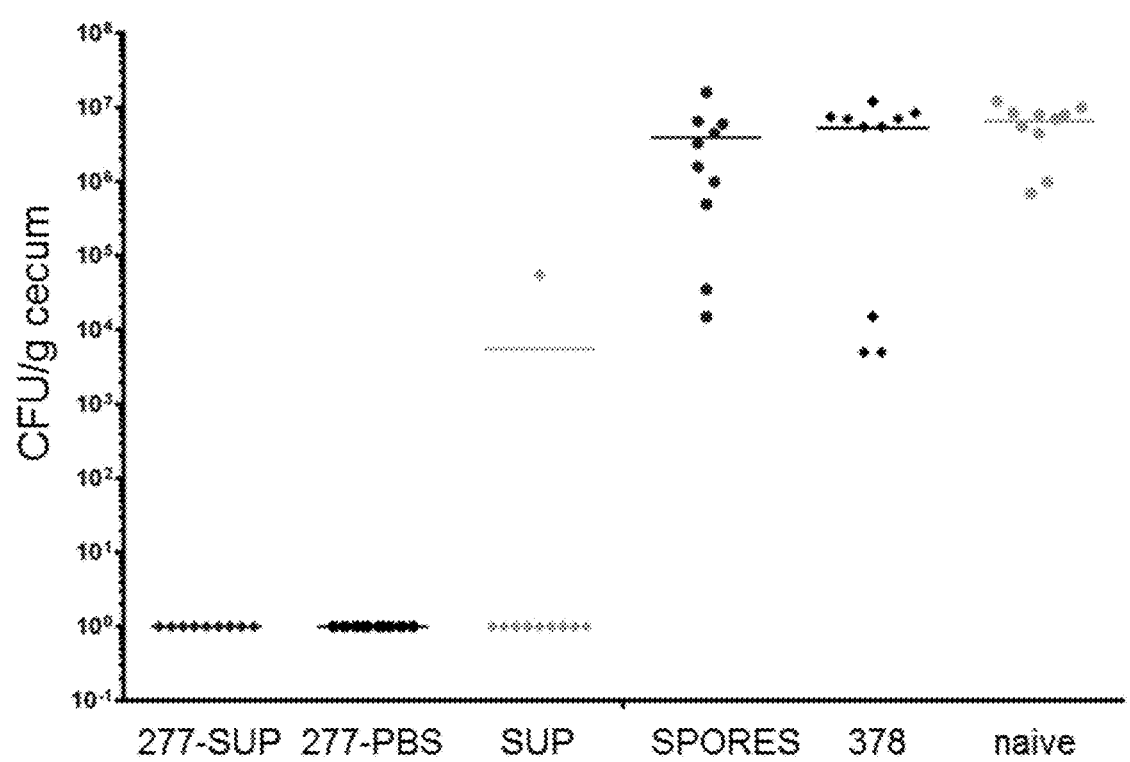
Figure 6B:
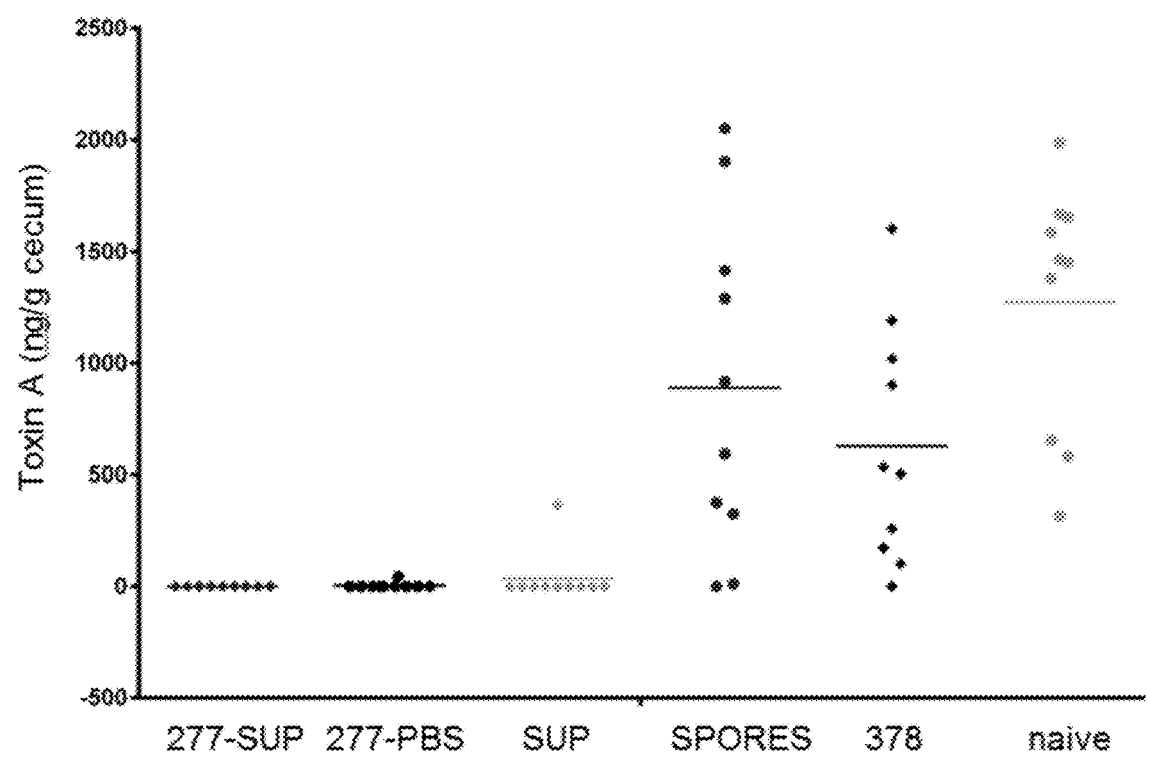
Figure 6C:
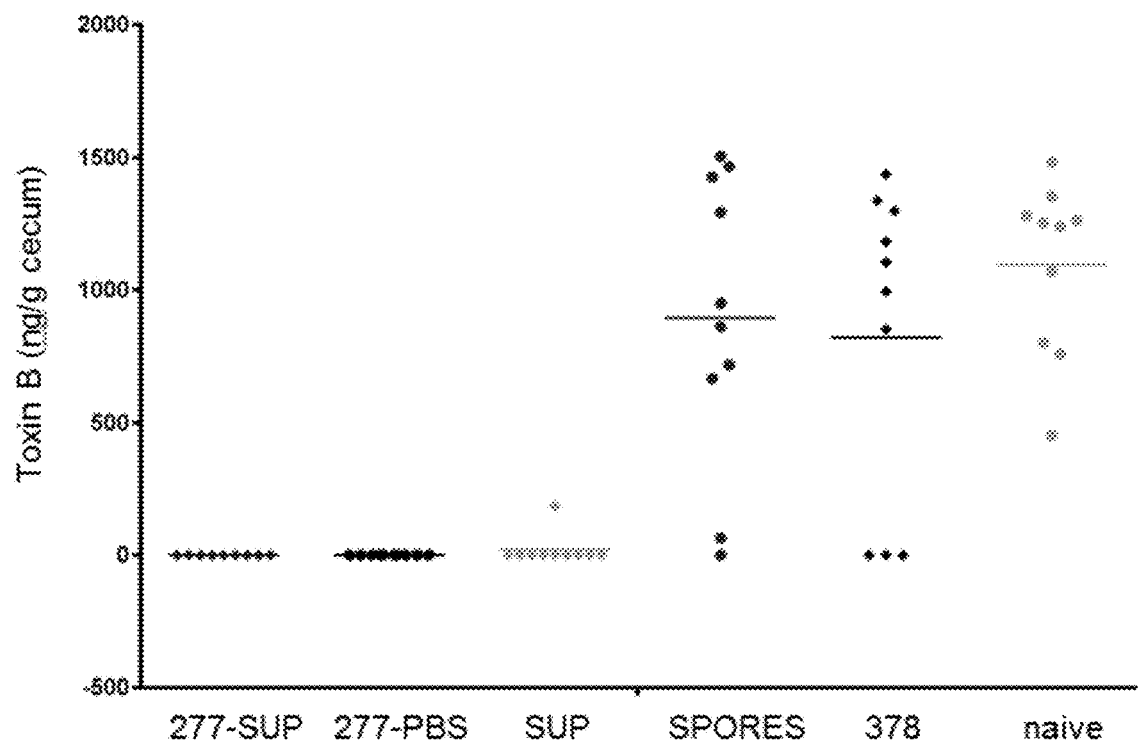

For evaluation in mice, the inventors used a model of CDI where two attributes are used to define colonisation, the presence of toxins A and B, and *C. difficile* CFU in the caecum (42). Animals were dosed with the four different SG277 preparations using the regimen shown in FIG. 1A. As well as a naïve group, the inventors also included a group dosed with *B. amyloliquefaciens* SG378 cells (suspended in their supernatant) that did not show any in vitro inhibition to *C. difficile* and served as a negative control. The results are shown in FIG. 6, which show that five doses of 277-SUP or 277-PBS prevented colonisation of CD630 as shown by the absence of bacterial CFU and toxins A and B in the caecum, see FIGS. 6A, 6B and 6C, respectively. Use of the cell free supernatant derived from SG277 (SUP) achieved almost complete arrest of colonisation with one mouse having low levels of *C. difficile* CFU and toxins in the caecum. Surprisingly, SPORES showed no effect on *C. difficile* colonisation and were similar to the SG378 and naïve groups. In total, the inventors have conducted eight murine experiments evaluating the ability of SG277 to prevent CDI and have also conducted studies using SG297 with identical conclusions (not shown).

Figure 7A:
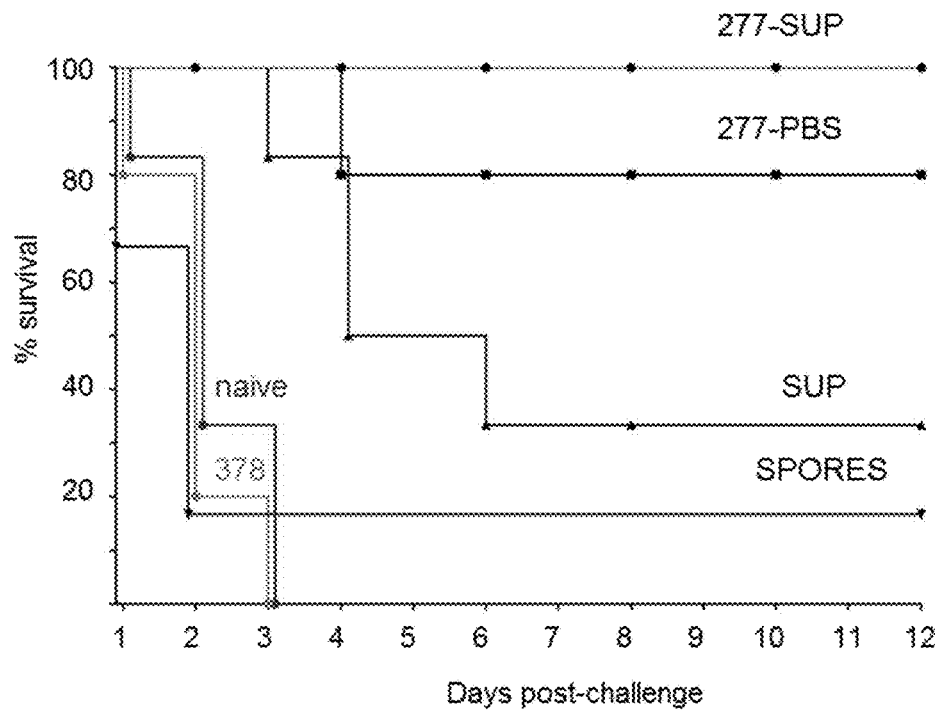

Hamsters are considered a 'gold-standard' for evaluation of CDI (43). The inventors used them to evaluate the ability of the same SG277 treatments described above for mice to prevent CDI. As explained in the Method section, the inventors' dosing strategy involved multiple doses of each treatment using groups of six hamsters per treatment. Animals showing symptoms of CDI were sacrificed, and the survival curves of the groups is shown in FIG. 7A. It will be noted that 277-SUP provided 100% protection to a lethal challenge with CD630. Furthermore, 277-PBS protected 5 out of the 6 hamsters, SUP protected 2 out of the 6 hamsters and SPORES protected 1 out of the 6 hamsters. Naïve animals and animals dosed with SG378 cells showed no protection.

Figure 7B:
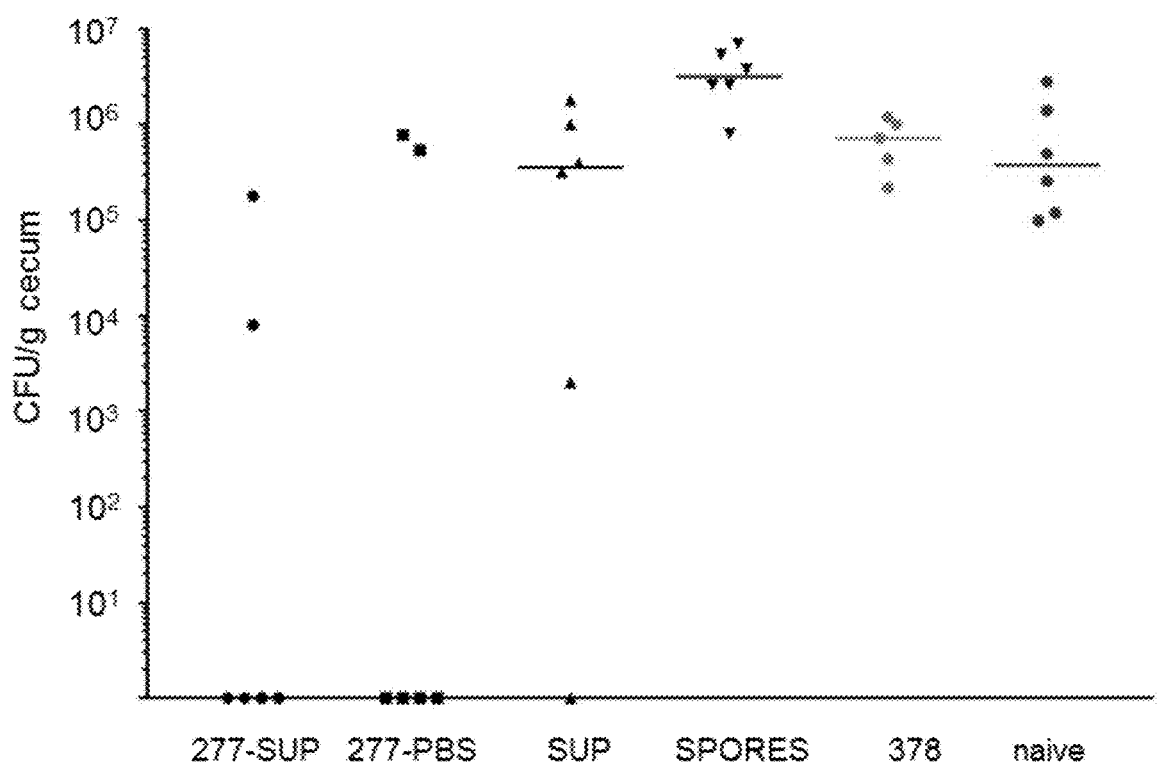
Figure 7C:
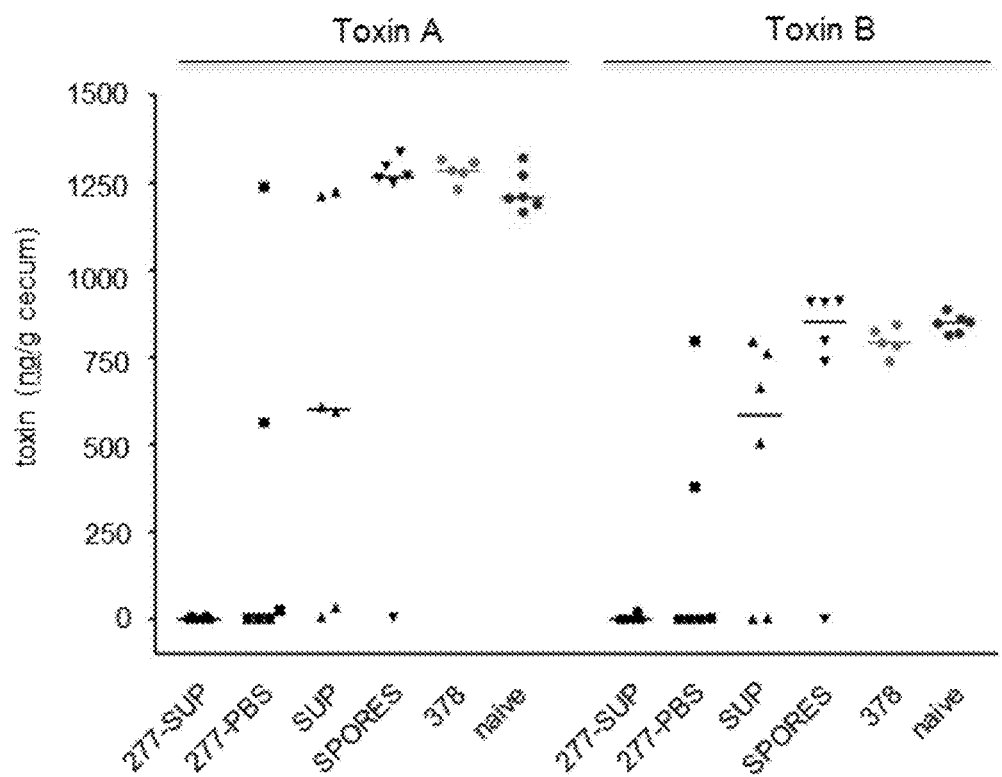

FIGS. 7B and 7C show levels of CD630 CFU and toxins in caecum samples, respectively.

The inventors have conducted three other hamster studies with similar results and, combined with the mouse data, this has clearly demonstrated that a suspension of 277-SUP or 277-PBS prevents *C. difficile* colonisation.

Two further points can be made. First, SPORES (i.e., a suspension of SG277 spores only) have limited efficacy, for which the inventors must assume that insufficient numbers of spores can germinate in the GI-tract to secrete the biosurfactant, AmyCide™. Second, despite the in vitro data, the cell-free supernatant was not as effective as when combined with cells. As shown above, the inventors predict that AmyCidem remains partially attached to the cell envelope and possibly is more efficacious when associated with the cell wall, and so this contribution to efficacy is likely important. In addition, the inventors predict that cells transiently proliferate in the GI-tract, further boosting the levels of AmyCidem. In data not shown, the inventors have found that SG277 administered to mice as a single dose persists (as determined by faecal shedding) for up to 10 days post-dosing.

Example 6: Identification of the Active Compounds

Using centrifugal concentrators of different molecular weight (mwt.) cut-offs the inventors determined the approximate molecular weight of AmyCide™ contained within the filter-sterilised (0.45 μm) supernatant from SG277, as shown in Table 8.

TABLE 8

Activity against CD630 measuring for filter-sterilised supernatant from SG277 with different molecular weight cut-offs using a microdilution assay

| Cut-off (kDa) | Activity titre | % |
|---|---|---|
| Untreated | 1/80 | 100 |
| <10 | 0 | 0 |
| 10-30 | 0 | 0 |
| 30-100 | 1/40 | 50 |
| >100 | 1/40 | 50 |

Approximately 50% of total activity was present in the 30-100 kDa fraction with approximately another 50% being present in the >100 kDa fraction, suggesting that AmyCide™ might exist as a complex, be physically labile and could dissociate while retaining some activity.

Using 20% ammonium sulphate (AmSO$_4$), the inventors found that the precipitate carried activity against *C. difficile* as well as biosurfactant activity. Surprisingly, SDS-PAGE analysis of the functionally active AmyCidem preparation yielded no Coomassie stained protein bands in the mwt. range 5-200 kDa but a single, white-coloured feature (labelled GB), resembling a band, with an estimated mwt. of the order of 1 kDa.

Figure 8A:
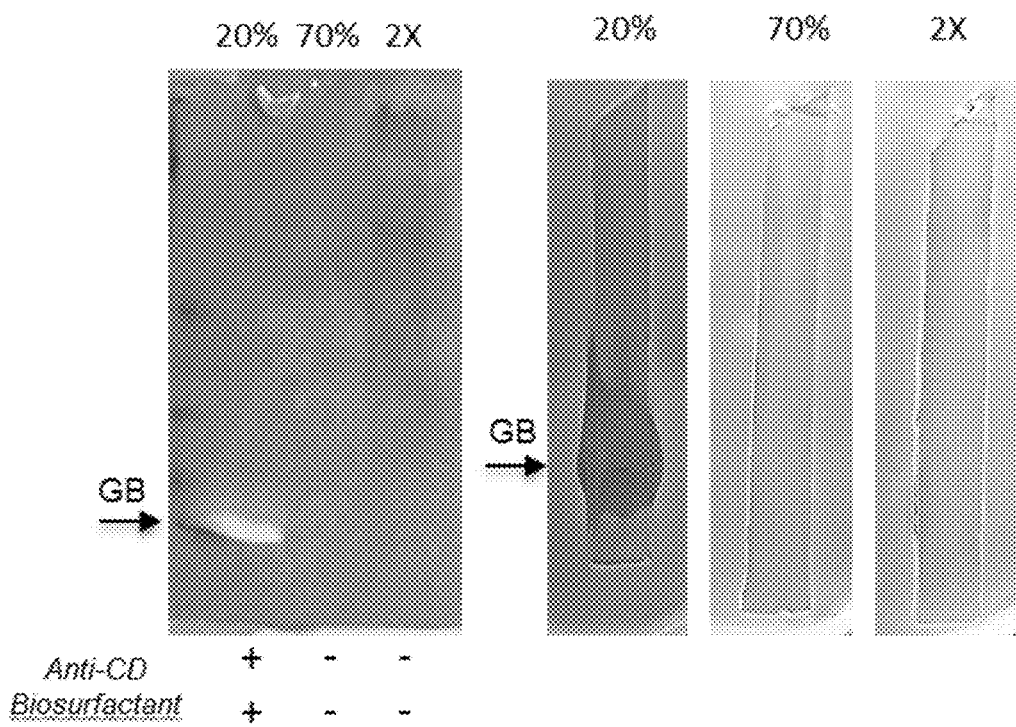
Figure 8B:
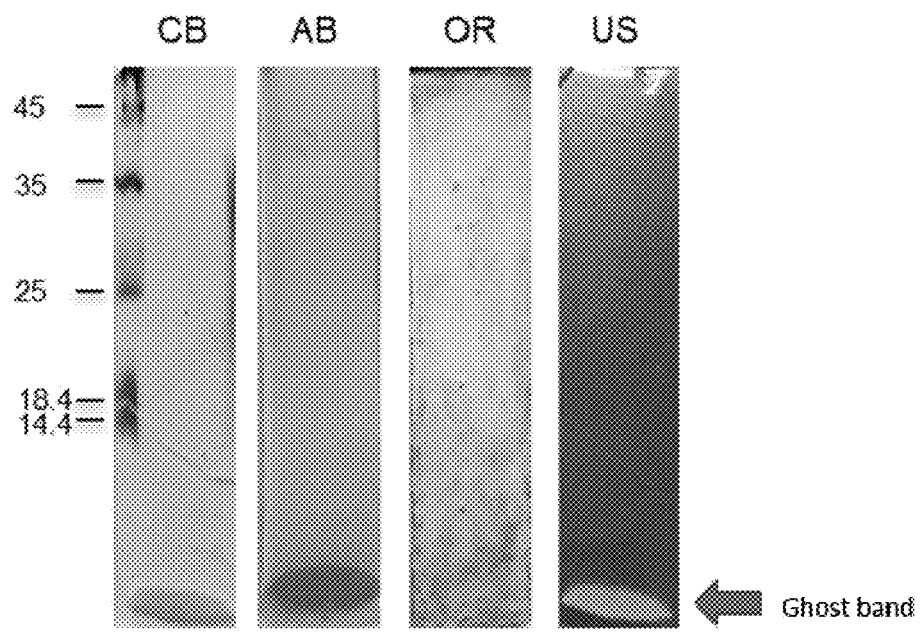

Proteins were only apparent following a combined 20%-70% precipitation. When SDS was eluted from the gel functional activity against live CD630 bacteria could be observed corresponding to the same band (labelled GB), see FIG. 8A. This band stained weakly with 'Oil Red O'(lipids) but was clearly stained with Alcian blue, see FIG. 8B. The apparent low mwt. by SDS-PAGE did not agree with the AmSO$_4$ precipitation since 20% AmSO4 should only precipitate high mwt. or hydrophobic molecules. As shown below the mwt. does correspond to that of the active moieties but the inventors suspect that the white band might also represent aberrant migration related to the structure of the complex.

Figure 8C:
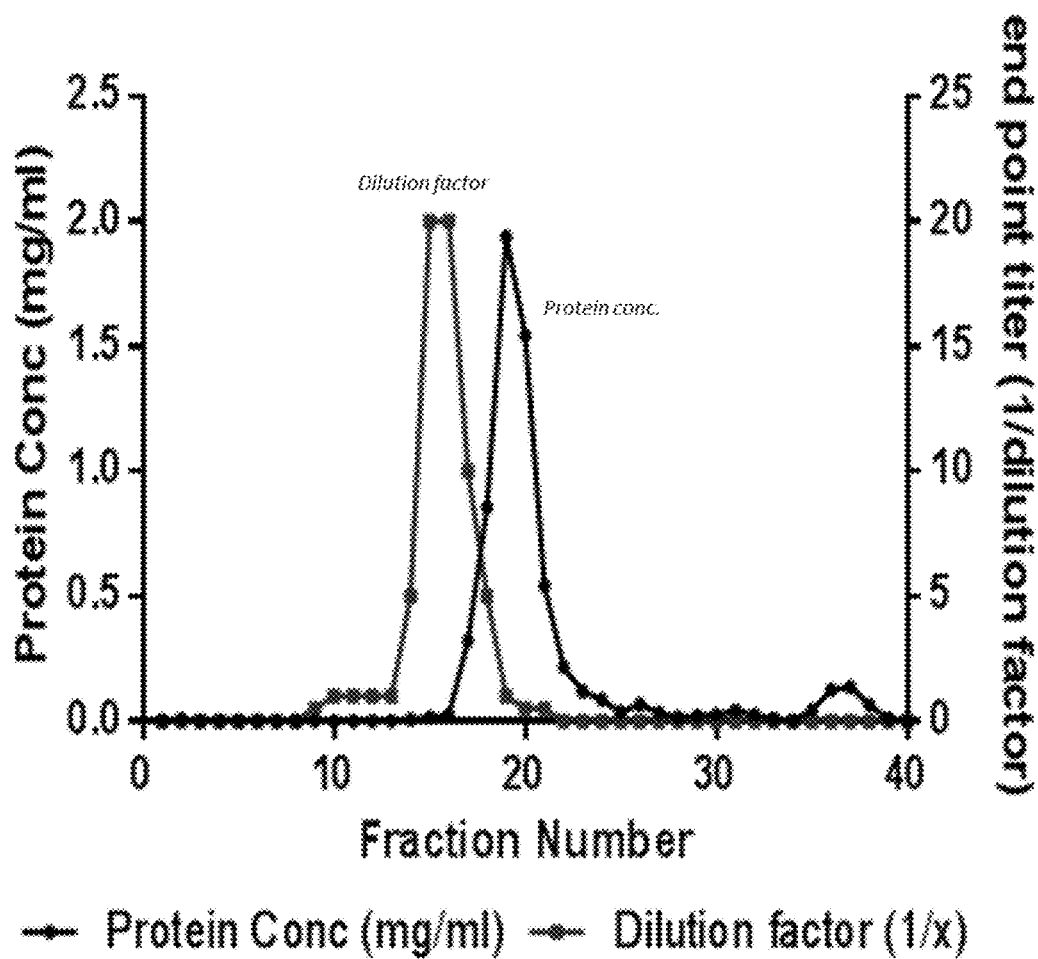
Figure 8D:
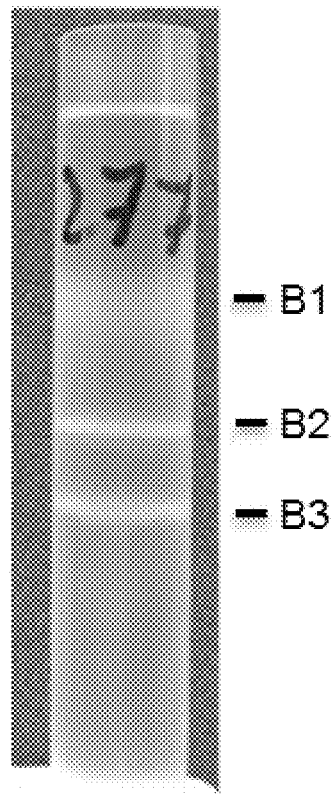

Gel filtration of the 20% AmSO$_4$ precipitate also confirmed that the active, 'AmyCide™', component did not correspond to the protein fractions, see FIG. 8C. Finally, the inventors found that AmyCide™ could be precipitated using PEG (polyethylene glycol) and following centrifugation through CsCl gradients three distinct bands were present of which only band B2 carried functional activity against *C. difficile*, see FIG. 8D.

AmSO4 precipitation was also performed on the sterile filtrate. This method enabled precipitation of the large molecular weight species responsible for the functional activity (as evidenced in MWCO experiments), and to reduce the amount of protein which would be co-purified alongside them. The active species were further purified by crude separation of high MW species. FIG. 27 demonstrates SDS removal of protein from the eluted fractions containing the active species. Fractions were tested for activity against CD630 (shown as a dilution factor) using a microplate assay and active fractions were combined and washed to remove excess SDS. FIG. 24 shows a similar analysis using internal markers (BSA and lysozyme). This analysis shows that activity is unlikely to be protein.

Electron microscopy revealed distinct aggregates present in the active fractions following both CsCl gradient centrifugation and size exclusion chromatography, see FIGS.

9A and 9B. Interestingly, this analysis revealed clusters of spherical-like granules of ~20-30 nm in diameter. Since the Alcian blue staining implied a polysaccharide component, this could correspond to the mucilage associated with the outer cell wall that would be rich in exopolysaccharides and agrees with the ability of these strains to form mucoid colonies and robust biofilms.

The inventors also confirmed the presence of gamma-polyglutamic acid (γ-PGA) in the $AmSO_4$ precipitate as well as the presence of γ-PGA biosynthetic genes on the SG277 and SG297 genomes. Taken together AmyCide™ must constitute a high mwt. and primarily, non-proteinaceous complex, carrying a combination of exopolysaccharides and γ-PGA derived from the cell surface mucilage.

To characterise AmyCidem further, the inventors used size-exclusion chromatography (SEC) using the microdilution assay to identify active fractions that were then analysed further by RP-HPLC. Fifteen distinct fractions were obtained by RP-HPLC, see FIG. 10A, and using MALDI-TOFF, these were identified as different isoforms of the lipopeptides, iturin A, fengycin, surfactin and mycosubtilin, see Table 9.

TABLE 9

Activity of RP-HPLC fractions of AmyCide™ against CD630 determined using a microdilution assay

| Fraction[a] | Activity[b] | M wt.[c] | Identity[c] |
|---|---|---|---|
| 1 | 1/5 | 1065.5 $[M + Na]^+$ | $C_{14}$ Iturin A[d] |
| | | 1081.5 $[M + K]^+$ | $C_{14}$ Iturin A[d] |
| | | 1043.5 $[M + H]^+$ | $C_{14}$ Iturin A[d] |
| 2 | — | 1065.5 $[M + Na]^+$ | $C_{14}$ Iturin A[e] |
| 3 | 1/5 | 1079.5 $[M + Na]^+$ | $C_{15}$ Iturin A |
| | | 1095.5 $[M + K]^+$ | $C_{15}$ Iturin A |
| | | 1057.5 $[M + H]^+$ | $C_{15}$ Iturin A |
| 4 | — | 1093.5 $[M + Na]^+$ | $C_{16}$ Iturin A |
| | | 1109.5 $[M + K]^+$ | $C_{16}$ Iturin A |
| | | 1071.5 $[M + H]^+$ | $C_{16}$ Iturin A |
| 5 | — | 1093.5 $[M + Na]^+$ | $C_{16}$ Iturin A |
| | | 1109.5 $[M + K]^+$ | $C_{16}$ Iturin A |
| 6 | — | 1107.5 $[M + Na]^+$ | Mycosubtilin |
| | | 1123.5 $[M + N]^+$ | Mycosubtilin |
| 7 | — | 1471.8 $[M + Na]^+$ | $C_{15}$ Fengycin A and/or $C_{13}$ Fengycin B[f] |
| | | 1449.8 $[M + H]^+$ | $C_{15}$ Fengycin A and/or $C_{13}$ Fengycin B[f] |
| | | 1487.8 $[M + K]^+$ | $C_{15}$ Fengycin A and/or $C_{13}$ Fengycin B[f] |
| 8 | — | 1463.8 $[M + H]^+$ | $C_{16}$ Fengycin and/or $C_{14}$ Fengycin B |
| | | 1503.8 $[M + H]^+$ | $C_{16}$ Fengycin A[g] and/or $C_{14}$ Fengycin B[g] |
| 9 | 1/20 | 1477.7 $[M + H]^+$ | $C_{17}$ Fengycin and/or $C_{15}$ Fengycin B |
| | | 1517.8 $[M + H]^+$ | $C_{17}$ Fengycin and/or $C_{15}$ Fengycin B[h] |
| | | 1463.8 $[M + H]^+$ | $C_{16}$ Fengycin A and/or $C_{14}$ Fengycin B |
| 10 | 1/40 | 1016.6 $[M + Na]^+$ | $C_{12}$ Surfactin |
| | | 1032.6 $[M + K]^+$ | $C_{12}$ Surfactin |
| | | 1054.6 $[M + Na]^+$ | $C_{12}$ Surfactin[i] |
| | | 1070.6 $[M + K]^+$ | $C_{12}$ Surfactin[i] |
| | | 1491.8 $[M + H]^+$ | $C_{18}$ Fengycin A and/or $C_{16}$ Fengycin B |
| | | 1477.8 $[M + H]^+$ | $C_{17}$ Fengycin A and/or $C_{15}$ Fengycin B |
| | | 1499.8 $[M + Na]^+$ | $C_{17}$ Fengycin A and/or $C_{15}$ Fengycin B |
| | | 1515.8 $[M + K]^+$ | $C_{17}$ Fengycin A and/or $C_{15}$ Fengycin B |
| 11 | 1/80 | 1046.6 $[M + K]^+$ | $C_{13}$ Surfactin |
| | | 1030.6 $[M + Na]^+$ | $C_{13}$ Surfactin |
| | | 1068.6 $[M + Na]^+$ | $C_{13}$ Surfactin[j] |
| | | 1084.6 $[M + K]^+$ | $C_{13}$ Surfactin[j] |
| | | 1491.8 $[M + H]^+$ | $C_{18}$ Fengycin A and/or $C_{16}$ Fengycin B |
| | | 1513.8 $[M + Na]^+$ | $C_{18}$ Fengycin A and/or $C_{16}$ Fengycin B |
| | | 1529.8 $[M + K]^+$ | $C_{18}$ Fengycin A and/or $C_{16}$ Fengycin B |
| 12 | 1/80 | 1060.6 $[M + K]^+$ | $C_{14}$ Surfactin |
| | | 1044.6 $[M + Na]^+$ | $C_{14}$ Surfactin |
| | | 1082.6 $[M + Na]^+$ | $C_{14}$ Surfactin[k] |
| | | 1098.6 $[M + K]^+$ | $C_{14}$ Surfactin[k] |
| 13 | 1/80 | 1058.6 $[M + Na]^+$ | $C_{15}$ Surfactin |
| | | 1074.6 $[M + K]^+$ | $C_{15}$ Surfactin |
| | | 1096.5 $[M + Na]^+$ | $C_{15}$ Surfactin[l] |
| | | 1112.5 $[M + K]^+$ | $C_{15}$ Surfactin[l] |
| | | 1080.6 $[M + H]^+$ | $C_{15}$ Surfactin[l] |
| 14 | 1/40 | 1072.6 $[M + Na]^+$ | $C_{16}$ Surfactin |
| | | 1088.6 $[M + K]^+$ | $C_{16}$ Surfactin |
| | | 1058.6 $[M + Na]^+$ | $C_{15}$ Surfactin[m] |
| | | 1074.6 $[M + K]^+$ | $C_{15}$ Surfactin[m] |
| | | 1110.6 $[M + Na]^+$ | $C_{16}$ Surfactin[n] |
| | | 1126.6 $[M + K]^+$ | $C_{16}$ Surfactin[n] |
| 15 | — | 1086.6 $[M + Na]^+$ | $C_{17}$ Surfactin |
| | | 1102.6 $[M + K]^+$ | $C_{17}$ Surfactin |
| | | 1072.6 $[M + Na]^+$ | $C_{16}$ Surfactin[o] |
| | | 1058.6 $[M + Na]^+$ | $C_{15}$ Surfactin[o] |
| | | 1124.6 $[M + Na]^+$ | $C_{17}$ Surfactin[p] |

Figure 10A:
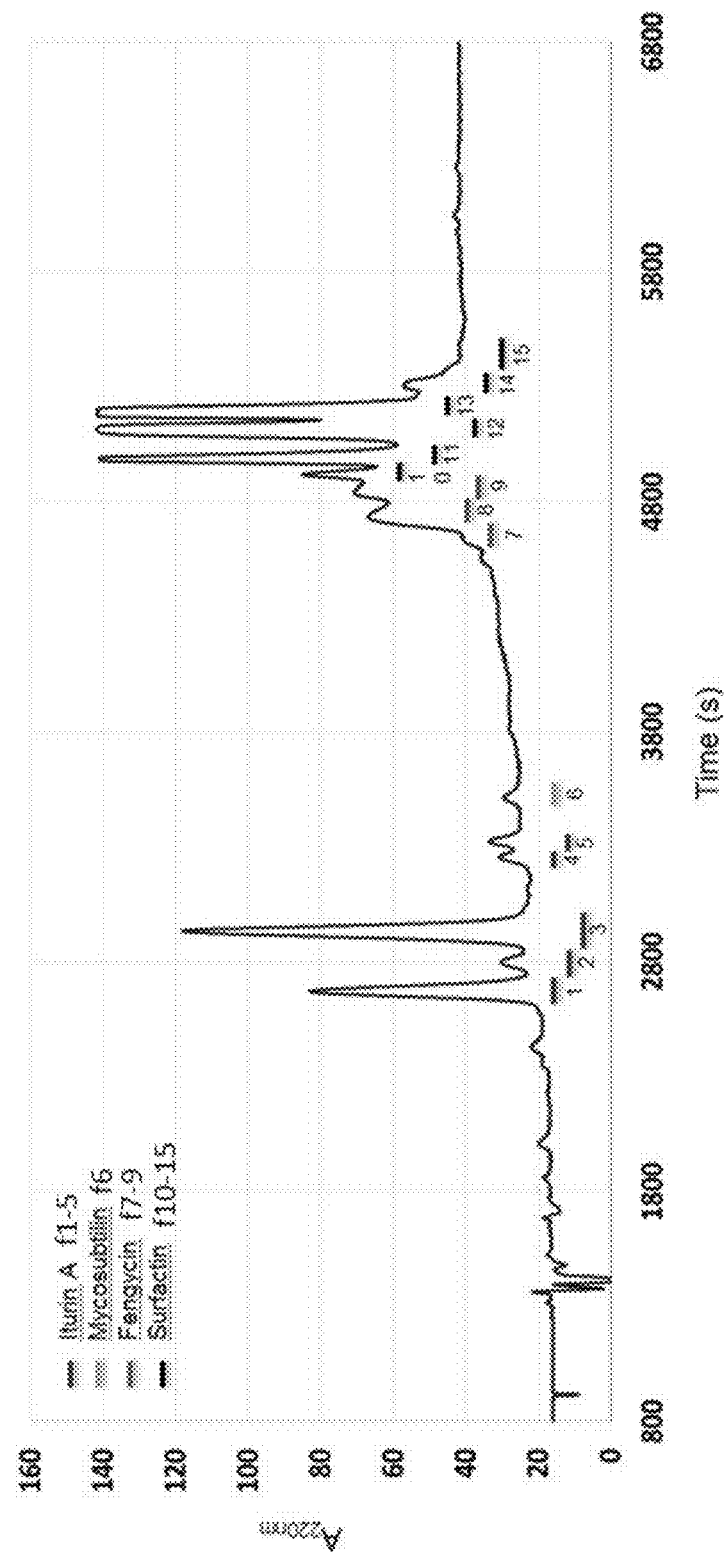
Figure 10B:
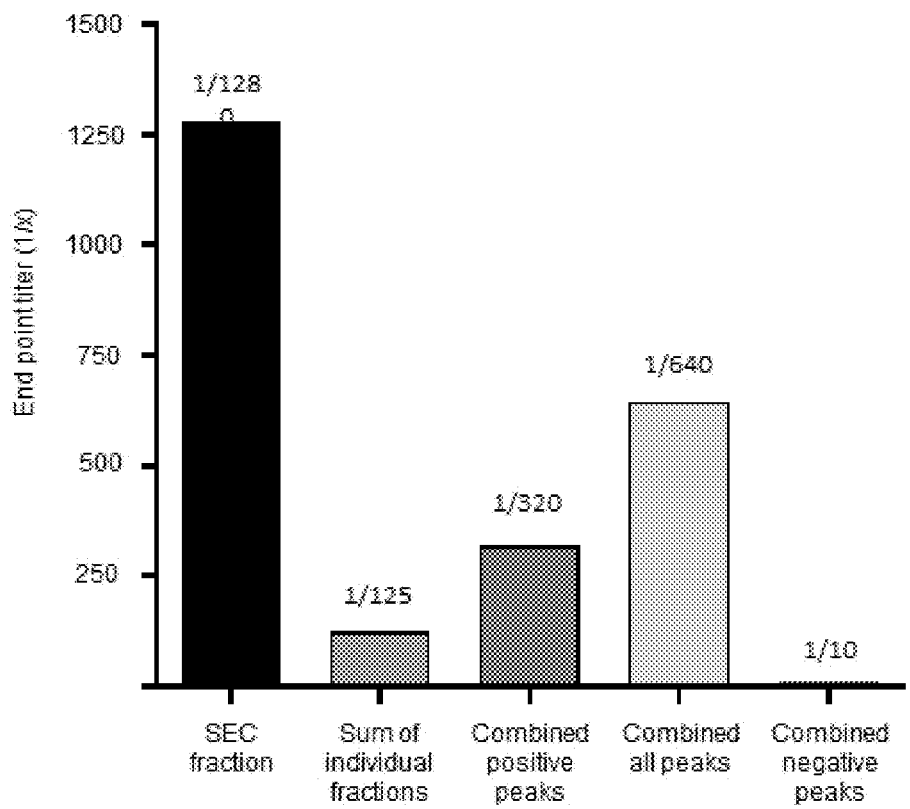

[a]RP-HPLC fraction from FIG. 10A.
[b]activity of fraction against CD630 determined using a microdilution assay.
[c]Monoisotopic mass, identity determined using MALDI-TOF.
[d]trace levels of $C_{13}$ Iturin A
[e]potential evidence of Mojavensin A
[f]trace levels of $C_{13}$ Kurstakin
[g]acetylated
[h]minor components, acetylated $C_{17}$ Fengycin and/or $C_{15}$ Fengycin B
[i]$C_{12}$ & $C_{13}$ surfactins with amino acid modifications
[j]say $C_{13}$ & $C_{14}$ surfactins with amino acid modifications
[k]say C14 & $C_{15}$ surfactins with amino acid modifications
[l]minor components, $C_{15}$ & $C_{16}$ surfactins with amino acid modifications, $C_{17}$ Fengycin B and $C_{16}$ Fengycin B
[m]minor components
[n]ay $C_{16}$ & $C_{17}$ surfactins with amino acid modifications
[o]minor components
[p]$C_{17}$ & $C_{18}$ surfactins with amino acid modifications The identity of the iturins, fengycins and surfactins was also confirmed using NMR (not shown). In addition, the inventors also observed evidence of two additional lipopeptides, mojavensin A (44) and kurstakin (45). As shown in FIGS. 10A and 10B and Table 9, using the microdilution assay they found that eight fractions (all iturin A and surfactin isoforms) carried anti-CD630 activity albeit with reduced activity.

The SG277 sterile filtrate was $AmSO_4$ precipitated and subjected to size exclusion chromatography and the active fraction (5 mg) lyophilised and then suspended in either water, PBS or 50% methanol and incubated for 1 h at RT. The inventors demonstrated that methanol could dissociate the complex, shifting activity to the low mwt. compounds of <5 kDa, see Table 11, in agreement with the known mwts. of iturin A, surfactin, fengycin and mycosubtilin (46, 47). However, using commercial sources of iturin A and surfactin, the inventors were unable to demonstrate any activity against CD360 whether alone or combined.

TABLE 11

Activity of different molecular weight cut-offs using different solvents

| Solvent | Concentrator m wt. cut-off | | | | |
|---|---|---|---|---|---|
| | <5 kDa. | <10 kDa. | <30 kDa. | <50 kDa. | <100 kDa. |
| water | − | − | − | + | + |
| PBS | − | − | − | + | + |
| 50% methanol | + | + | + | + | + |

Interestingly, the inventors found that if the 7 positive RP-HPLC fractions were combined the activity against *C. difficile* was increased almost 3-times compared to the cumulative activity of the individual fractions. If RP-HPLC fractions 1-15 were reconstituted, the anti-*C. difficile* activity was at least four-times greater than the cumulative activity of individual RP-HPLC fractions, see FIG. 10B. Together this suggested a strong synergistic effect of the individual moieties and also a contribution of fractions that alone carried no activity (i.e., the negative fractions exhibiting no activity).

Accordingly, the inventors have shown that AmyCidem produced by *B. amyloliquefaciens* and *B. subtilis* is a water-soluble complex that associates with the cell envelope and comprises different isoforms of iturin A, surfactin, mycosubtilin, fengycin A and B. The inventors have shown that when combined, the apparent mwt. of the active fraction is higher than that of the individual monomers indicating that micelles are formed, a characteristic of many biosurfactants (49). Advantageously, these micelles have been shown to aggregate into nanostructures, are more stable and resistant to degradation, have enhanced solubility and carry a higher antimicrobial activity than the monomeric form (50-52). Without wishing to be bound to any particular theory, the inventors suspect that AmyCide™ is mostly likely a mixture of different factors, including lipopeptides that in some *B. amyloliquefaciens* strains are produced in sufficient concentrations to form micelles.

It is possible that mixed micelles are being formed. Micelles might be considered a 'laboratory-based' phenomenon, but the SEM images of aggregates of spherical-like granules obtained following SEC resemble synthetically produced micelles (53). The inventors believe that Amy-Cide™ micelles might, in some way, be stabilised or entrapped in the copious exopolysaccharides that encase the vegetative cell mucilage. The 'active' strains examined here produced profuse biofilms and produced mucoid colonies, both attributes requiring the production of large amounts of extracellular polysaccharide (54).

Surfactant molecules form micelles at concentrations higher than the critical micelle concentration (CMC) (49). If surfactants were produced at sufficiently high concentrations by the inventor's *B. amyloliquefaciens* strains then this might explain how activity was associated with the high mwt fractions. Ultrafiltration has been used to purify and concentrate biosurfactants where at concentrations greater than the CMC surfactants can be purified (58).

Figure 12:
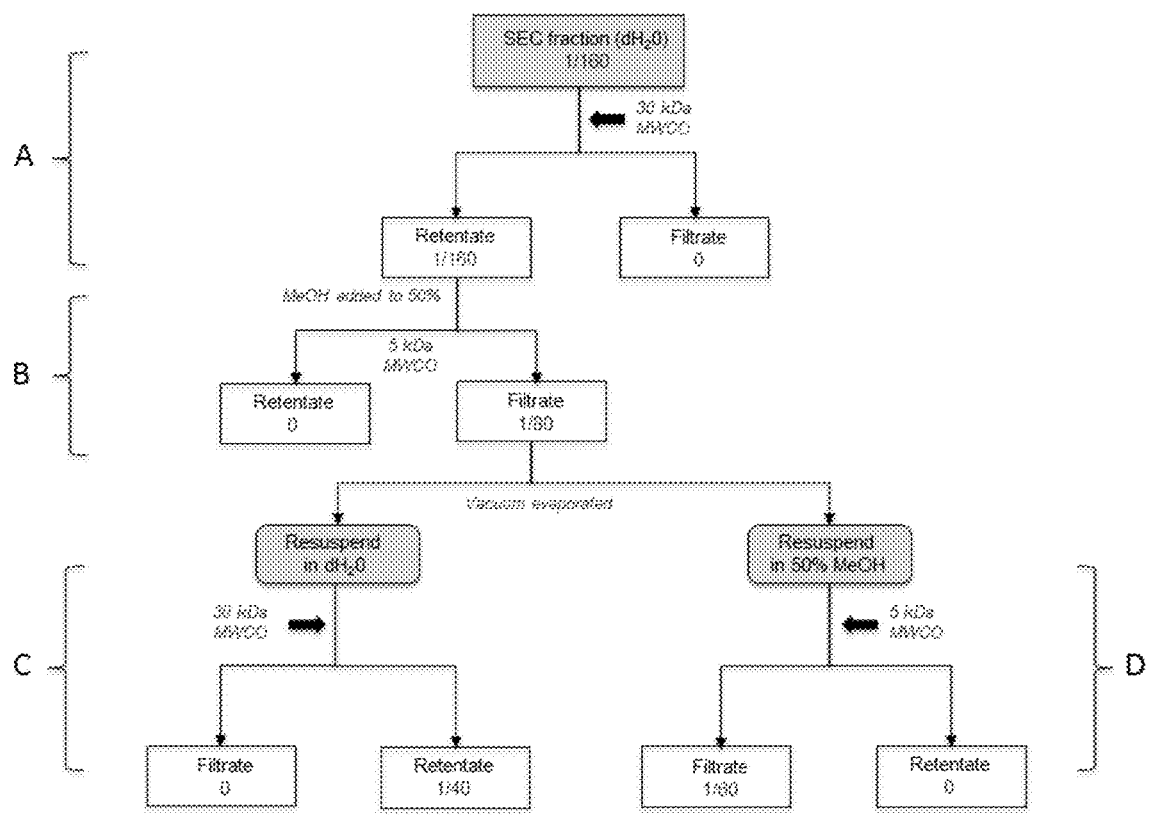
FIG. 12 shows how a SEC fraction from an AmSO4 precipitated cell-free supernatant of SG277 was treated, and the activity of the resultant samples.

As shown in FIG. 12A, starting with a SEC fraction from an $AmSO_4$ precipitated cell-free supernatant of SG277, the inventors centrifuged (8,000×g, 15 min) the sample through a 30 kDa molecular weight cut-off (MWCO) filter to ensure activity measured was for the micelles with a mwt. greater than 5 kDa. As shown in FIG. 12B, the retentate containing the high MW micelles was collected and MeOH added to a final concentration of 50% (v/v) and incubated for 1 h at RT. The resulting mixture was centrifuged under the same conditions as described above using a 5 kDa MWCO filter and the filtrate containing the low MW biosurfactant molecules collected, aliquoted in equal volumes into 2 separate Eppendorfs and vacuum evaporated. The remaining pellets were resuspended in either $dH_2O$ (FIG. 12C) or 50% MeOH (v/v) (FIG. 12D) and both centrifuged under the same conditions as described above using 5 kDa or 30 kDa MWCO filters. Retentates and filtrates were collected. All fractions were normalized by volume and tested for activity against CD630 using a microdilution assay.

Accordingly, the inventors have shown that methanol (50%) was able to disrupt this activity enabling activity to correlate with a mwt. of less than 5 kDa. If the filtrate was then dissolved in water, then the mwt of activity reverted to >5 KDa (and >30 kDa). This suggests that the apparent high mwt of anti-*C. difficile* activity corresponds to the formation of surfactant micelles. Surfactants are produced at sufficiently high levels by these bacteria enabling them to form micelles either comprised of individual surfactants or mixed populations.

Figure 13A:
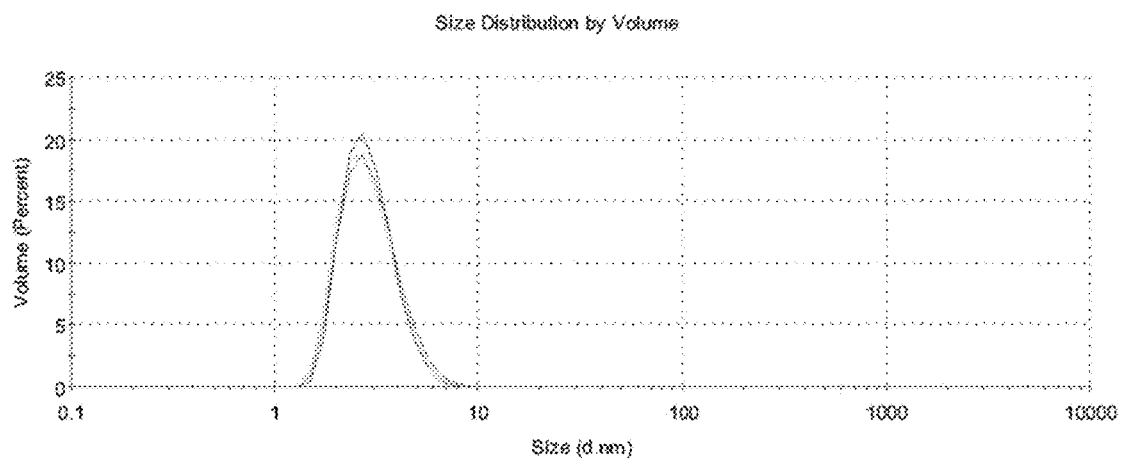
FIG. 13A shows the size distribution by volume (by DIS analysis) for a SEC fraction from an AmSO4 precipitated cell-free supernatant of SG277.
Figure 13B:
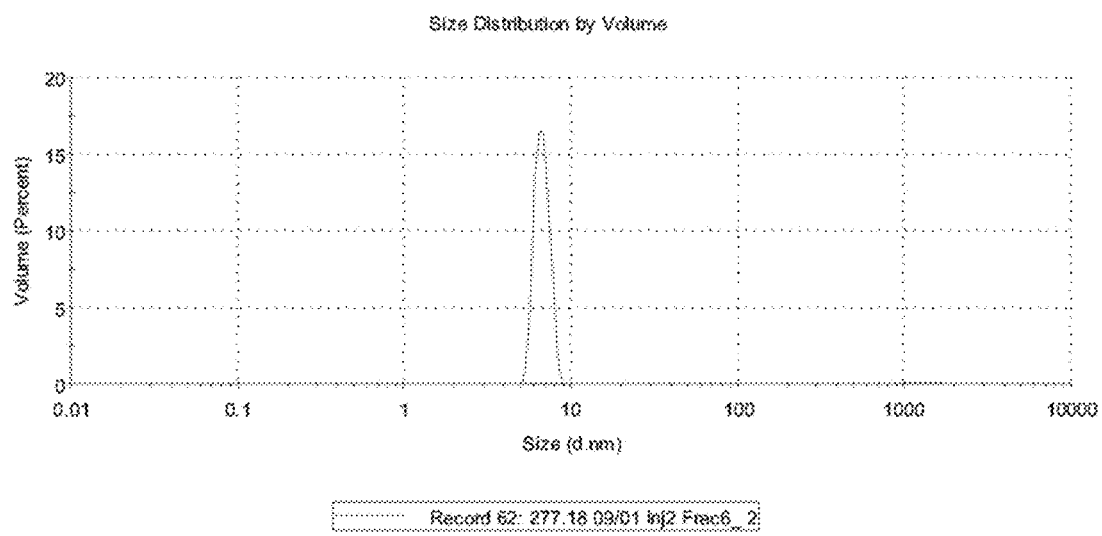
FIG. 13B shows the size distribution by volume (by DLS analysis) for fraction 3 of FIG. 10A ($C_{15}$ iturin A)
Figure 13C:
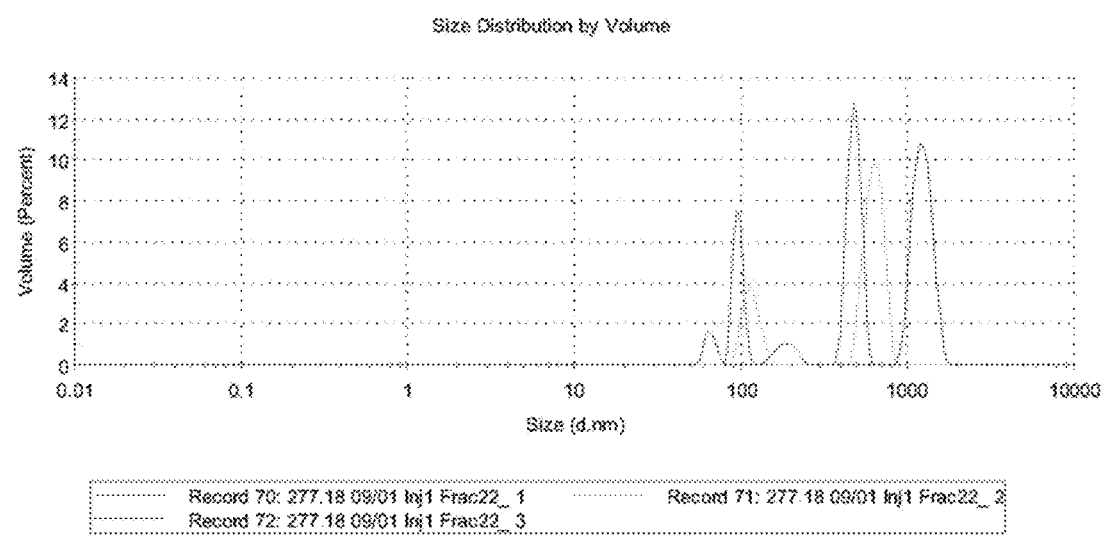
FIG. 13C shows the size distribution by volume (by DLS analysis) for fraction 13 of FIG. 10A ($C_{15}$ surfactin)

Using dynamic light scattering (DIS), the inventors examined the SEC fraction of an SG277 $AmSO_4$ precipitate in $dH_2O$ revealing one large population, most likely micelles, with an average size of 3 nm (*1 nm; see FIG. 13A) together with a trace of aggregates. Examining the RP-HPLC fractions suspended in $dH_2O$ only fraction 3 ($C_{15}$ iturin A) carried micelles with a diameter of 7 nm (see FIG. 13B). For fraction 13, corresponding to $C_{15}$ surfactin, only aggregates of 70-100 nm were observed (see FIG. 13C). This data shows that $C_{15}$ iturin A is soluble in water and capable of forming micelles. The micelles present in the SEC fraction are smaller but would equate to a globular protein of about 65 kDa and are consistent with the failure of the active SEC fraction to pass through a kDa MWCO filter. It is not clear why the SEC fraction carried particles of −3 nm whereas $C_{15}$ iturin A exhibited 7 nm particles however other studies (59) have documented differences in size and without wishing to be bound to any particular theory, most probably micelle size is related to the relative concentration of lipopeptides as well as the formation of mixed micelles (that may contain $C_{15}$ iturin A).

$C_{15}$ iturin A is an example of a lipopeptide able to form micelles and is water-soluble. The inventors suspect that $C_{15}$ iturin A may enable other lipopeptides to be solubilised in water and potentially form mixed micelles enabling them to target the bacterial cell. To test this, the inventors mixed water solubilised $C_{15}$ iturin A with a commercial surfactin (Sigma S3523; derived from *B. subtilis* and a mixture of $C_{13}$-$C_{15}$ surfactins). The commercial surfactin was not soluble in water and showed no activity against *C. difficile* while $C_{15}$ iturin A had a functional activity of ¹⁄₄₀ using the microplate assay. Confirming their hypothesis, the combined $C_{15}$ iturin A+$C_{15}$ surfactin exhibited a higher activity against *C. difficile* (¹⁄₁₆₀). This then reveals a possible mechanism for activity against *C. difficile* hypothesised by the inventors. The presence of $C_{15}$ iturin A enables the solubilisation of Cis surfactin in water and probably all or many of the other lipopeptides present in or on the cell wall of SG277 and other *Bacillus* species. The important requirements for activity are the concentration of lipopeptides that are produced (since micelles can only be formed at levels above a critical threshold). The micelles formed are most likely to be mixed micelles (i.e., carrying different lipopeptide species but all carrying $C_{15}$ iturin A)(at least for *B. amyloliquefaciens*).

The 3 nm size of water-soluble micelles in the SEC fraction is believed to be important because it may also explain how the micelles are able to make contact with the cell envelope of *C. difficile*. As biosurfactants, the molecule must interact with the phospholipid bilayer of *C. difficile* (or other sensitive bacteria).

Figure 14:
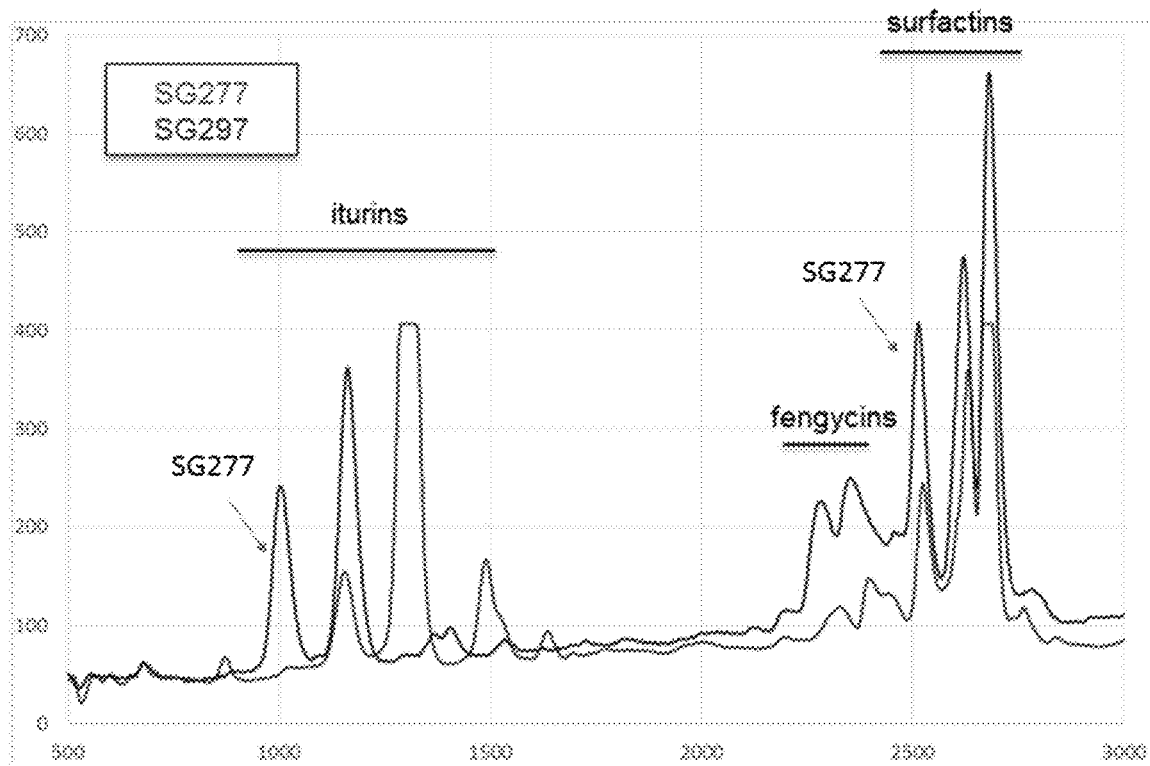
FIG. 14 is a comparison of the RP-HPLC profiles of *B. amyloliquefaciens* SG277 vs SG297.

Comparison of RP-HPLC fractions from *B. amyloliquefaciens* SG277 and SG297 (see FIG. 14) showed somewhat different profiles with SG297 exhibiting new iturin species (1300-1600 on scan)

Figure 15:
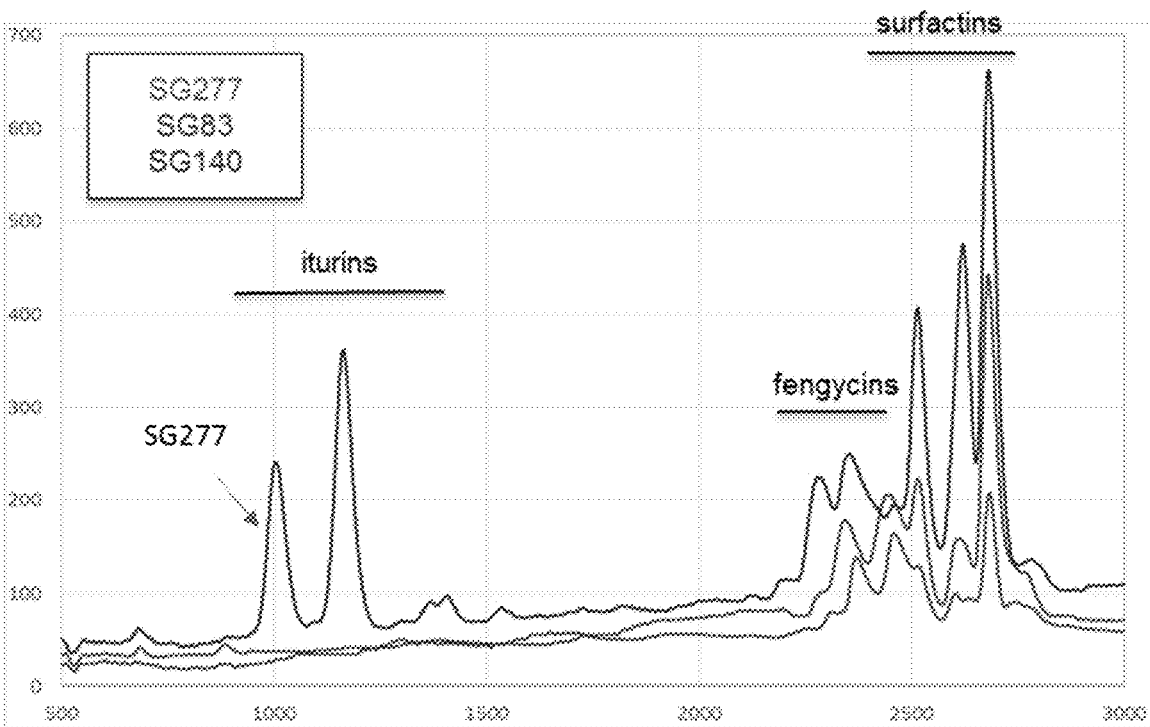
FIG. 15 is a comparison of the RP-HPLC profiles of *B. amyloliquefaciens* SG277 vs. *B. subtilis* SG83 and SG140.

Comparison of SG277 and two *B. subtilis* positive strains (SG83 and SG140) showed that the *B. subtilis* strains did not produce iturins (FIG. 15) suggesting that i) the reduced (compared to SG277 and SG297) activity of these *B. subtilis* strains might be explained by the absence of iturin A, and ii) lipopeptides other than iturin A contribute to the solubilisation suggesting that a complex stoichiometric relationship of lipopeptides contributes to activity.

Figure 16:
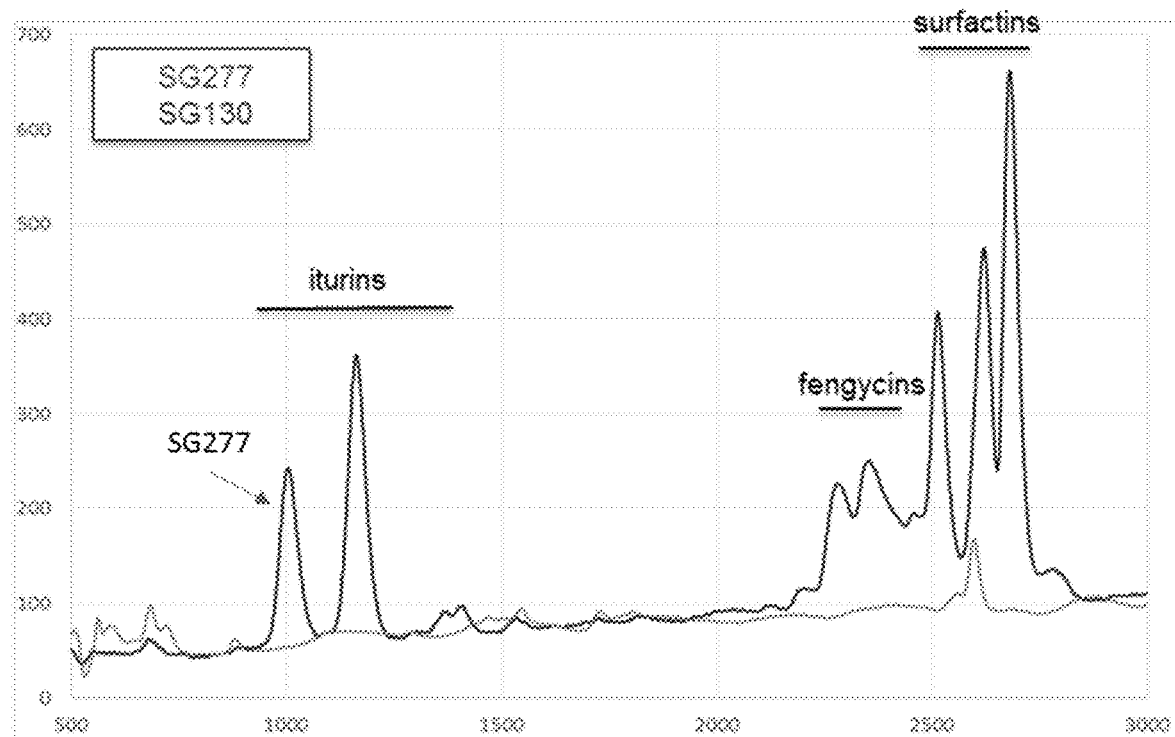
FIG. 16 is a comparison of the RP-HPLC profiles of *B. amyloliquefaciens* SG277 vs. *B. licheniformis* SG130.

Lastly, a 'positive' *B. licheniformis* strain (SG130) was shown to produce no biosurfactants (see FIG. 16) agreeing with the inventors' original observations (see Example 1).

Figure 11:
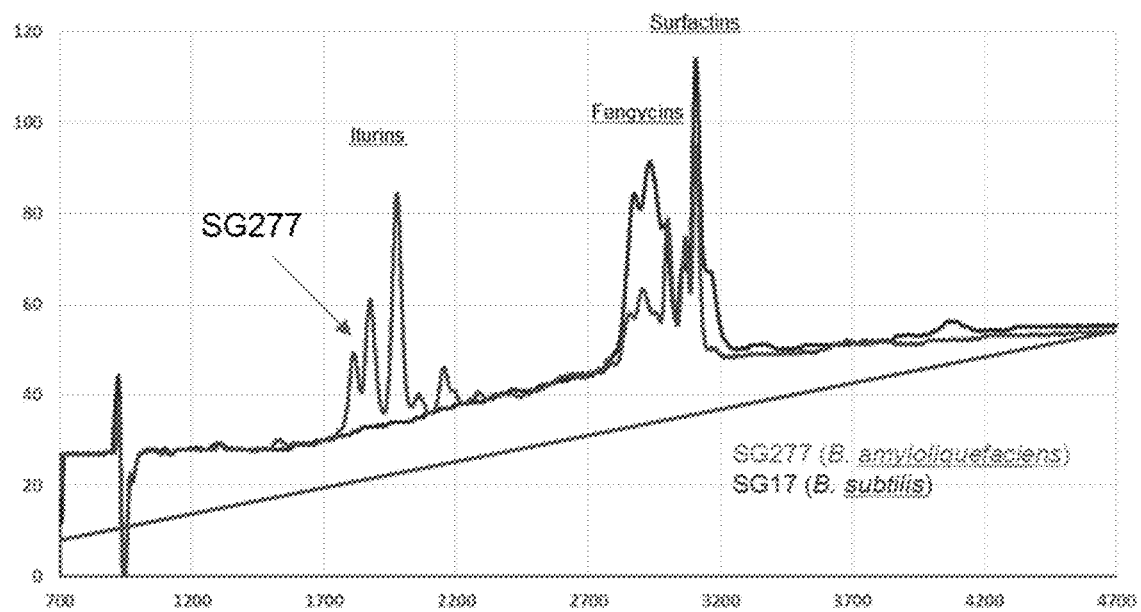
FIG. 11 is an RP-HPLC comparison of the biosurfactant AmyCide™ in *B. subtilis* SG17 vs. *B. amyloliquefaciens* SG277.

Returning to the original mouse experiments reported in Example 1, the inventors verified that first, surfactins and iturins were detectable in mouse faeces as well as in intestinal homogenates (jejunum, ileum, caecum), and second, that the three mouse-*Bacillus subtilis* strains (SG17, SG83 and SG140) produced surfactins. FIG. 11 shows the RP-HPLC fraction of *B. subtilis* SG17. Interestingly, SG17 (like SG83 and SG140) did not appear to carry iturins but was rich in fengycins and surfactins. Since the activity of this strain against *C. difficile* was less than the *B. amyloliquefaciens* strains, see FIG. 3A, the inventors speculate that activity correlates with the abundance of lipopeptides in AmyCide™ and for stronger activity iturin combined with fengycins and surfactins produces a greater effect. In addition, and as mentioned later, *B. subtilis* strains appear to be less proficient at production of certain antibiotics, most notably s Chlorotetaine, that are more abundant (or more stable) in *B. amyloliquefaciens*. This also suggests that the ability of mouse-derived *Bacillus* strains to control CDI was most probably due to the AmyCidem biosurfactant in combination with antibiotics.

Example 7: Bacteriolytic Vs Bacteriostatic Activity

Figure 17:
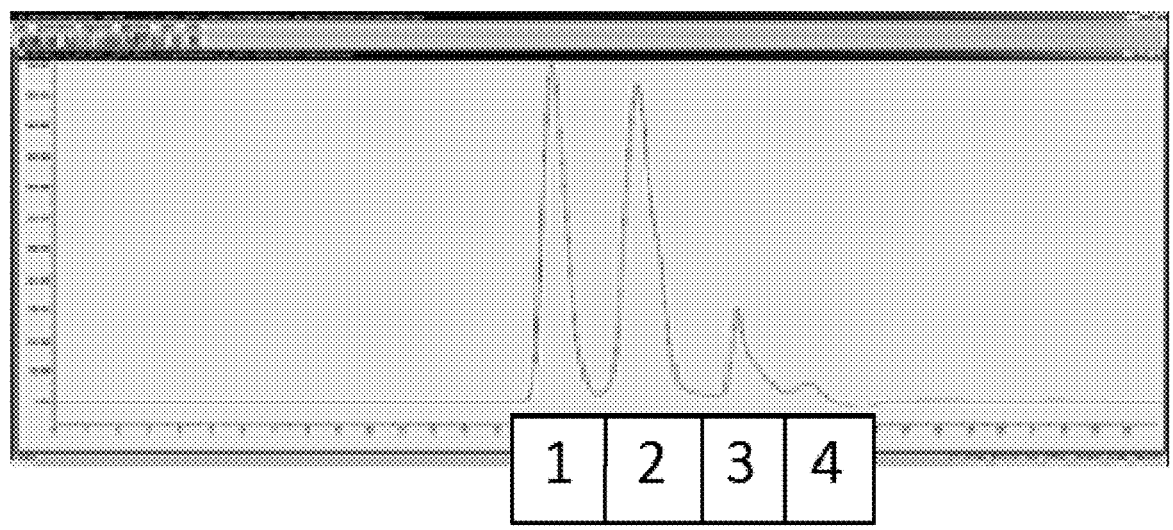
FIG. 17 shows SEC-HPLC fractions 1-4 of crude SEC material.

To further examine the constituent species of the crude SEC active fraction, separation was performed using a SEC-HPLC column (FIG. 17). This column separates molecules between the range of 200-3,000 Da. Acetonitrile was used as the isocratic buffer providing the same denaturing conditions as discussed above. Four Fractions were collected, tested for activity against CD630 and analysed by MS.

Fractions 1-3 were analysed for their ability to inhibit growth of cultures of CD630 by addition of test material at the log phase of cell growth ($OD_{600}$~0.3). Test materials were diluted in $dH_2O$ to normalise so that each sample to be tested carried the same activity/volume. 120 ml of diluted test material was added to 1 ml of CD630 culture and 0.2 ml removed hourly for OD600 readings. For this study the test materials were as shown in Table 12.

TABLE 12

Test materials

| Test material | Description | Original activity $(1/n)^a$ | Dilution required[b] |
|---|---|---|---|
| 1 | sterile extracellular filtrate | 160 | 10 |
| 2 | $AmSO_4$ ppt | 5120 | 320 |
| 3 | SEC crude fraction[c] | 2560 | 160 |
| 4 | fraction 1[d] | 320 | 20 |
| 5 | fraction 2[d] | 0 | 20 |
| 6 | fraction 3[d] | 320 | 20 |
| 7 | fraction 1 + 3 | 320 | 20 |

[a]original activity determined using a microplate assay
[b]the test material is dissolved in dH2o to normalise activity to 16. The dilution factor is indicated.
[c]the active fraction determined by SEC of the AmSO4 ppt
[d]active fractions following SEC-HPLC analysis of the crude SEC active fraction Optical density ($OD_{600}$) was measured before and after addition of test material. A decline in $OD_{600}$ indicates bacteriolytic activity while stalling of the increase in $OD_{600}$ indicates either bacteriostatic or bacteriocidal growth. On the other hand a decline in CFU/ml indicates both bacteriolytic and/or bacteriocidal activity. (FIGS. 22A and 22B and Table 13).

TABLE 13

Summary of anti-CD activity

| | Bacteriolytic[1] | Bacteriocidal[2] | Bacteriostatic[3] |
|---|---|---|---|
| Extracellular Filtrate[4] | + | + | − |
| AMSO4 | + | + | − |
| SEC[5] | ± | + | − |
| fraction 1 | + | + | − |
| fraction 2 | − | − | − |
| fraction 3 | − | + | − |
| fraction 4 | not tested | not tested | not tested |

[1]decline in OD600 of the CD630 culture
[2]cessation of cell growth (CD630 cfu/ml)
[3]inhibition of cell growth (CD630 cfu/ml)
[4]sterile extracellular filtrate
[5]SEC fraction prior to HPLC analysis. This produced partial lysis.

The basic identity of each fraction is shown in Table 14 below.

TABLE 14

SEC-HPLC Fractions

| Fraction | Composition | anti-CD activity | other[1] |
|---|---|---|---|
| 1 | surfactin | + (1/320) | cloudy solution |
| 2 | Iturins & fengycin | − | clear solution |
| 3 | Chlorotetaine | + (1/320) | clear solution |
| 4 | n/a (tail from 3) | | |

[1]clear solution can indicate good solubility

Fraction 3 was bacteriocidal while fraction 1 (surfactins) was bacteriolytic. The SEC crude fraction showed partial bacteriolytic activity. Without wishing to be bound to any particular theory, the inventors believe this is because of the SDS used in the preparation of the SEC fraction from the AmSO4 precipitate may have disrupted micelles and thus activity. Taken together, this suggests that functionality of AmyCide™ complex is dependent on molecular composition and variations in the concentration of individual components influences activity. Interestingly, the inventors have observed that fraction 3 is significantly reduced and sometimes absent in B. *subtilis* strains possibly explaining their lowered activity to C. *difficile*.

Figure 2:
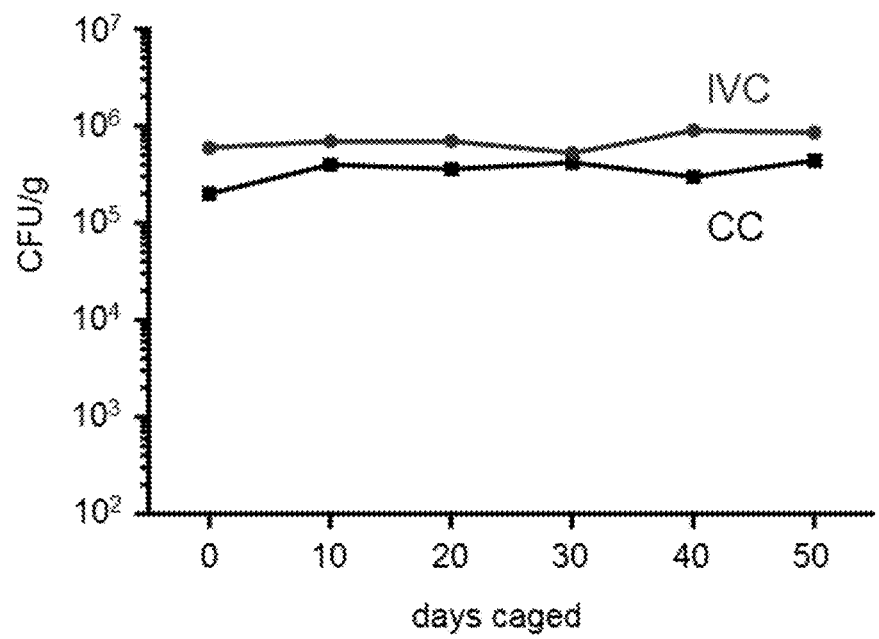
Figure 2:
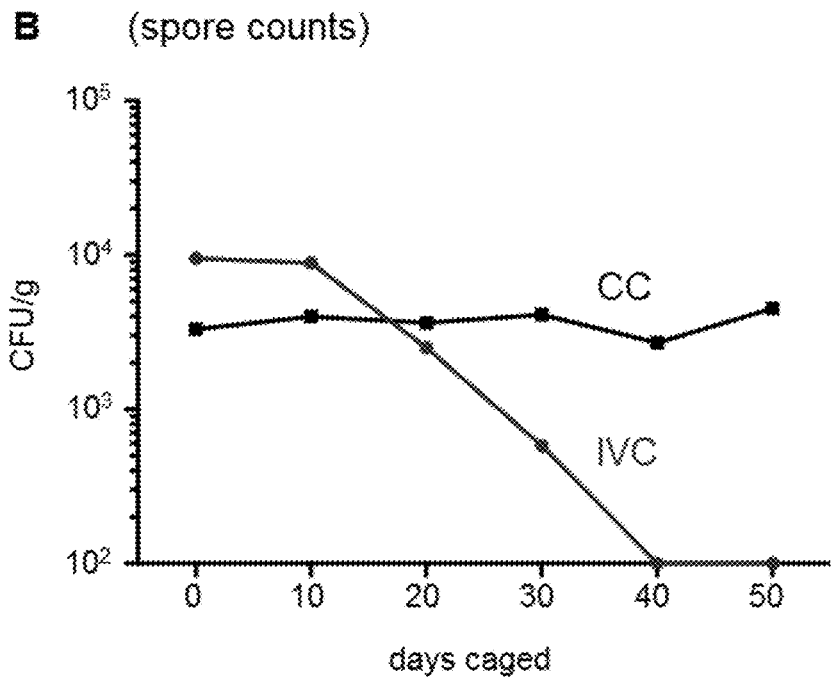

Further analysis was performed on factions 1-3, whereby individual fractions from SEC-HPLC analysis were now run on an RP-HPLC column (FIG. 18A-C). In parallel the inventors also ran the SG277 SEC active fraction (same as FIG. 10 above) for comparison. As can be seen fraction 1 corresponded to surfactins, fraction 2 to iturins and fengycins and fraction 3 gave no absorption indicating no peptide component.

SEC-HPLC fraction 3 was applied to an RP-HPLC column and 36 fractions analysed for anti-CD630 activity. In parallel the SG277 total crude SEC fraction was run on RP-HPLC and 36 fractions examined (FIG. 19).

Fractions 1-5 of SEC-HPLC fraction 3 showed clear activity to CD630 and the MS analysis of these fractions is shown in Table 15.

For SG277 run by RP-HPLC in parallel Fraction 4 and fractions 30-32 of the SG277 crude SEC showed activity. Fractions 30-32 are Surfactins while the identity of fraction 4 using mass spec is shown in Table 16 below. Note that low activity was sometimes found with Iturin fractions but not found in the analysis shown here. The species clearly identifiable in fraction 4 was the antibiotic Chlorotetaine. This was the only compound is important for understanding how how AmyCidem kills *C. difficile*.

Fractions 1-9 of SEC-HPLC fraction 3 do not absorb at 220 nm and therefore the active fractions (1-9) are unlikely to be proteinaceous or lipopeptides. Surfactin however, is also a component in inhibiting CD suggesting a complex.

TABLE 15

Mass-Spc ID of Fractions 1-5 of the RP-HPLC fractionation of SG277 SEC

| ID | m/z | other |
|---|---|---|
| Chlorotetaine | 311 | Chlorotetaine ($^{35}$Cl) [M + Na] |
| | 313 | Chlorotetaine ($^{37}$Cl) [M + Na] |
| | 327 | Chlorotetaine ($^{35}$Cl) [M + K] or Hydroxychlorotetaine ($^{35}$Cl) [M + Na] |
| | 329 | Chlorotetaine ($^{37}$Cl) [M + K] or Hydroxychlorotetaine ($^{37}$Cl) [M + Na] |
| | 333 | Chlorotetaine ($^{35}$Cl) [M − H + 2 × Na] |
| | 335 | Chlorotetaine ($^{37}$Cl) [M − H + 2 × Na] |
| | 343 | Hydroxychlorotetaine ($^{35}$Cl) [M + K] |
| | 345 | Hydroxychlorotetaine ($^{37}$Cl) [M + K] |

TABLE 16

Mass-Spec ID of Fraction 4 of the SEC-HPLC Fraction 3 by RP-HPLC (as shown in FIG. 36)

| measurement | | monoisotopic experimental m/z | Interpretation | monoisotopic theoretical m/z | ERROR D[a] | ERROR PPM |
|---|---|---|---|---|---|---|
| 311.094 | [M + Na] | 288.104 | Chlorotetaine ($^{35}$Cl) | 288.088 | 0.016 | 57 |
| 313.092 | [M + Na] | 290.102 | Chlorotetaine ($^{37}$Cl) | 290.085 | 0.017 | 60 |
| 327.079 | [M + K] | 288.116 | Chlorotetaine ($^{35}$Cl) | 288.088 | 0.028 | 96 |
| 327.079 | [M + Na] | 304.090 | Hydroxychlorotetaine ($^{35}$Cl) | 304.083 | 0.007 | 22 |
| 329.083 | [M + K] | 290.120 | Chlorotetaine ($^{37}$Cl) | 290.085 | 0.035 | 119 |
| 329.083 | [M + Na] | 306.094 | Hydroxychlorotetaine ($^{37}$Cl) | 306.080 | 0.014 | 44 |
| 333.072 | [M − H + 2 × Na] | 288.101 | Chlorotetaine ($^{35}$Cl) | 288.088 | 0.013 | 43 |
| 335.084 | [M − H + 2 × Na] | 290.112 | Chlorotetaine ($^{37}$Cl) | 290.085 | 0.027 | 93 |
| 343.067 | [M + K] | 304.103 | Hydroxychlorotetaine ($^{35}$Cl) | 304.083 | 0.020 | 66 |
| 345.067 | [M + K] | 306.103 | Hydroxychlorotetaine ($^{37}$Cl) | 306.080 | 0.023 | 76 |

[a]absolute error

Cryo-EM analysis was performed on the SEC fraction and showed small disc-like objects tightly packed and <10 nm in size. Also, occasional large size discs were apparent with a diameter of ~60 nm. These objects resembled micelles of <10 nm and ~160 nm in size (FIG. 2). Individual RP-HPLC fractions corresponding to Iturin A (1-3) fengycin (7-9) and surfactin (10-14) did not show micelles but instead rod-like filaments/fibres.

DIS Analysis (Dynamic Light Scattering) showed that the SEC fraction exhibited 3 nm particles agreeing with cyro-EM analysis (FIG. 21) and C14 surfactin (fraction 13 from RP-HPLC) showed large particles that using cryo-EM analysis correspond to fibres (not shown).

The inventors also assessed the synergistic effect of the identified factors using DLS (FIG. 23). This analysis revealed particle size in fractions of iturins, fengycins and surfactins. Combination of iturins, fengycins and surfactins changes particle size and indicate cooperativity and the building of a larger complex.

In a similar study it has been shown that lipopeptides of B. subtilis undergo a change in micelle size when combined (Jauregi, Coutte et al. 2013). For example, combining surfactin (5-105 nm) with mycosubtilin (8-18 nm) creates mixed micelles of 8 nm. This is similar to what the inventors observed.

The inventors also assessed activity against CD630 using a microdilution assay (Table 17).

TABLE 17

Activity against CD630 measured using a microdilution assay.

| Cut-off (kDa)$^a$ | Activity titre |
|---|---|
| Untreated | 1/80 |
| <10 | 0 |
| 10-30 | 0 |
| 30-100 | 1/40 |
| >100 | 1/40 |

Molecular weight cut off shows the size of molecules (table above) to be above 3 kDa and yet all lipopeptides demonstrated a range of sizes that are universally small in size (400-1.5 kDa). When separated on a SEC column the elution of the molecule would suggest a size of >20 kDa, comparing to protein standards (FIG. 24).

Without wishing to be bound to any particular theory, these two observations would imply that these components are monomers in solution but interacting with each other leading to a single complex which elutes in the same fraction during SEC separation. Interestingly if methanol is added to the SEC solution all interactions between components break down and molecular weight reduces to below 5 kDa—the size of lipopeptides as monomers. Addition of methanol to a solution increases the hydrophobicity of the solution resulting in the dissolution of the micelle as the intermolecular force between the more hydrophobic solvent and hydrophobic tail of the surfactant molecules increases. Cheng et al., 2013 provide an example of a similar blend of lipopeptides and glycolipids in B. subtilis. (Cheng, Tang et al. 2013). Note that discrepancy in size is also observed when considering CsCl2 ultracentrifugation which implies large molecular weight in comparison to the band of activity seen in SDS page gels which runs alongside the dye front. The SDS-page seems to separate the complex into individual, smaller components.

An assessment of the combination of different factors was performed. Fractions 1-3 from SEC-HPLC (FIG. 17) were examined for activity to CD630 either alone or in combination as shown in FIG. 25. All samples/fractions were normalised before combination.

fraction 1=surfactins
fraction 2=iturins and fengycins
fraction 3=Chlorotetaine

Addition of fractions 1+2+3 showed activity greater (1/640) than either 1, 2 or 3 alone or 1+2.1+3 or 2+3. The original SEC fraction was 1/1280 in this case (TOTAL).

Fractions from RP-HPLC fractionation (see FIG. 26) were combined together as shown in the Figure.

Commercial (SIGMA) samples of iturin (I), fengycin (F) and surfactin (S) were used in this analysis and none showed activity to CD630 alone or combined.

Fractions 1-3=iturin A
Fractions 7-9=fengycins
Fractions 10-14=surfactins

For RP-HPLC fractions iturins and fengycins showed low activity and less than surfactins (fr 10-14). The sum of individual peaks was 1/320 and when iturins (fr 1-3) were combined with fengycins (fr 7-9) and surfactins (fr 10-14) the activity increased to 1/640 but still less than the entire SEC fraction (1/1280).

Taken together this data for SEC-HPLC and RP-HPLC fractions shows a synergistic effect when individual active fractions are combined that is greater than the mathematical sum.

Example 8: Activity Against *Mycobacterium tuberculosis*

AmSO4 material from SG277 was subjected to SEC chromotography and 20 fractions analysed for activity to *M. tuberculosis*. The minimal inhibitory concentrations (MICs) of SEC fractions described above were determined for inhibition of drug-sensitive and drug-resistant *M. tuberculosis* growth and compared with the antibiotics. High inhibitory activity was observed for fractions 1, 2, 3 15 and 16 for both mycobacterial cultures (Table 18 and FIG. 28). Fractions 15 and 16 also showed activity to *C. difficile* strain 630 using an in vitro microdilution assay.

TABLE 18

MIC of compounds determined for drug sensitive *M. tuberculosis* H37Rv and multi-drug resistant *M. tuberculosis* (Peru isolate) by the REMA method.

| | MIC (μg/ml) | |
|---|---|---|
| Crude SEC Fractions | *M. tuberculosis* H37Rv | MDR-TB Peru isolate |
| 1 | 1/64 | 1/64 |
| 2 | 1/64 | 1/32 |
| 3 | 1/64 | 1/32 |
| 4 | 1/8 | 1/4 |
| 5 | >1/2 | >1/2 |
| 11 | >1/2 | >1/2 |
| 12 | >1/2 | >1/2 |
| 13 | >1/2 | >1/2 |
| 14 | 1/8 | 1/8 |
| 15 | 1/64 | 1/32 |
| 16 | 1/64 | 1/64 |
| 17 | 1/32 | 1/8 |
| 18 | 1/4 | 1/4 |
| 19 | >1/2 | >1/2 |
| 20 | >1/2 | >1/2 |
| Isoniazid | 0.25 | >4.0 |
| Rifampicin | 0.5 | >4.0 |

Rifamycin is considered a standard for treating Tuberculosis. The data here shows that RP-HPLC fractions carried activity to *M. tuberculosis*, notably, fractions 1-3 and 15 and 16.

Example 9: Activity Against *Staphylococcus aureus*

In Vitro Activity

An in vitro assay was used to assess activity against *S. aureus* (DL1065). *B. amyloliquefaciens* strains were all strains that showed extracellular activity against *C. difficile* and carried an AmyCide™ complex. SG378 was a *B. amyloliquefaciens* strain that showed no anti-CD activity. The results are shown in Table 19.

TABLE 19

In vitro activity of *B. amyloliquefaciens* strains to *S. aureus*

| *B. amyloliquefaciens* strain | Zone of inhibition (diameter, mm) | Activity |
|---|---|---|
| SG57 | 16 | + |
| SG137 | 26 | ++ |
| SG277 | 15 | + |
| SG297 | 18 | + |
| SG185 | 22 | ++ |
| SG378 | 0 | − |

In Vivo Activity

The inventors also performed an in vivo assay as described under the methods section above, to assess activity against *S. aureus*.

Sterile filtrates of a variety of *B. amyloliquefaciens* strains were added to exponentially growing cultures of *S. aureus*. Cell growth was monitored by optical density readings (FIG. 29). Using SEC (size exclusion fractions) bacterisotatic inhibition of *S. aureus* was also observed.

Extracellular activity to *S. aureus* was clearly present in three *B. amyloliquefaciens* strains, SG185, SG277 and SG297.

Example 10: Activity Against *V. harueyi* and *V. parahemolyticus*

The culture supernatant from SG277 and SG297 was added to cultures of *V. harveyi* and *V. parahemolyticus* at a final concentration of 1/10.

Both SG277 and SG297 supernatants exhibited activity against both *Vibrio* strains (*V. harveyi* and *V. parahemolyticus*) (FIGS. 30 and 31).

Example 11: Testing the Stability and Activity of AmyCide™ in Lyphophilised Form The stability of lyphophilised SG277 was tested at varying temperatures and compared with fresh SG2776. FIG. 4 highlights that SG277 is stable in lyphophilised form.

Lyophilised bacteria (a mixture of spores and vegetative cells) does not impair the efficacy of bacteria to prevent CDI. 100% protection is achieved (FIG. 32 to 35). This shows the active material survives lyophilisation and also is encouraging for its use as a final product.

Administration of supernatant material shows 66% protection while SEC purified material 33% protection. Even for animals still colonised with CD the levels of CD CFU is reduced. This suggests that the failure to obtain 100% protection most likely results from dosage and/or formulation. That is, using higher doses should confer 100% protection.

DISCUSSION

Targeted restoration of the gut microbiota has proven efficacious for the treatment of CDI but the mechanism of action has remained elusive, and includes rebalancing the gut microbiota, competitive exclusion and the contribution of predatory bacteriophages (10-12). The inventors show that these methods appear to have overlooked the contribution of aerobic spore-formers for control of CDI. There are several reasons for this. First, methods have employed sequence or metagenomic-based methods to identify candidates for bacteriotherapy. Second, previous methods all focus on anaerobic bacteria, and assume that minority bacterial populations are unlikely to play a predominant role in the control of intestinal infections.

By contrast, the inventors' approach has focused on traditional microbiological methods for identification of bacteria with functional activity coupled with a focus on aerobic spore-forming bacteria rather than anaerobic bacteria. Using CDI as a model gastrointestinal pathogen, the cohort of aerobic spore-formers from the inventor's work is mostly *Bacillus* species and, of course, these would ordinarily be mostly undetectable using standard metagenomic- or sequence-based approaches. These bacteria constitute an allochthonous population that implies the inventors' exposure to aerobic spore formers plays an important role in controlling CDI.

Rates of CDI are highest in industrialised countries, most notably the USA followed by the UK (62, 63) and it could be argued then that the increase in processed food and decreased exposure to environmental bacteria might be an important factor in why rates are so high in these countries. The hygiene hypothesis attempts to link changes in lifestyle in industrialised countries that have produced a decrease in infectious disease with a concurrent rise in allergic and autoimmune disease (64-67). The inventors speculate that, broadly, the same phenomenon may be a contributing factor underlying the high rates of CDI observed in the USA and UK (68, 69). Decreased exposure to environmental microbes through for example, diet and increased antibiotic usage, might be expected to lower our exposure to Bacilli and may, in part, account for the increased rates of CDI. As noted by others, the root cause is likely to be multifactorial (70) but the inventors believe that the contribution of exposure to environmental microbes has, hitherto, been unnoticed. Although the lack of thorough or proper diagnosis may partly explain the low incidence rates of CDI in developing countries it is intriguing that these are the same countries that have a record of abuse and overuse of antibiotics (71). It is also interesting that CDI is now beginning to emerge in many developing countries in parallel with improved living standards, hygiene and nutrition (72,73). The inventors suspect then that our exposure to environmental bacteria plays an important role in controlling CDI and also in other gastrointestinal diseases.

The ability of *Bacillus* species, including *B. amyloliquefaciens* and *B. subtilis*, to produce antimicrobials is well known and the, non-ribosomally produced, cyclic lipopeptides (iturins and surfactins and fengycins) are considered particularly powerful biosurfactants (47, 74-78). A number of these are used commercially as anti-fungal agents for the control of plant disease (79-81). The inventors show here that the functional biosurfacant or 'antibiotic', referred to herein as "AmyCidem", produced by *B. amyloliquefaciens* and *B. subtilis* is a large complex that associates with the cell envelope and comprises lipopeptide biosurfactants together with Chlorotetaine. The combination of biosurfactants is synergistic and at high concentrations creates micelles, most probably mixed micelles. The primary composition of these AmyCide™ micelles is surfactin but other lipopeptides (iturin A, surfactin, mycosubtilin and fengycin A and B) or glycolipids could substitute at high concentrations to produce similar micelles. These micelles appear to form complexes that also have the unique ability to combine or concentrate antimicrobials produced by *Bacillus* species, notably Chlorotetaine. Although Chlorotetaine is clearly bacteriocidal to *C. difficile* while the lipopeptides are by themselves bacteriolytic, without wishing to be bound to any particular theory, the inventors assume that the complex of lipopeptides and Chlorotetaine facilitates greater activity, possibly by enhancing the stability of one or both components (lipopeptides and/or Chlorotetaine) or increasing avidity, that is, the rate of killing. For example, but without wishing to be bound to any particular theory, the inventors believe that in the presence of biosurfactant micelles or as a complex the antibiotic, namely Chlorotetaine, has improved stability or a higher density, and thus more targeted activity. Chlorotetaine is a non-ribosomally synthesized dipeptide antibiotic similar to Bascilysin, an antibiotic commonly produced by *B. subtilis* (Phister et al, "Identification of bacilysin, chlorotetaine, and iturin a produced by *Bacillus* sp. strain CS93 isolated from pozol, a Mexican fermented maize dough", Appl Environ Microbiol 70(1): 631-634. The *B. amyloliquefaciens* strains described here all produce Bacilysin and it is likely that they use the same or a modified biosynthetic pathway. Bacilysin is a dipeptide composed of L-alanine and L-anticapsin and is known as a 'Trojan Horse antibiotic'. Susceptible cells use dipeptide permeases to import Bacilysin after which peptidases release the anticapsin inside the cell. Anticapsin, as an analogue of glutamine, can inhibit glucosamine synthase. The irreversible inhibition of glucosamine synthase results in the lysis of bacterial or fungal cells. Chlorotetaine is a dipeptide carrying an unusual chlorine-containing amino acid (3'-chloro-4'-oxo-2'-cyclo-hexenyl) alaninc fused to L-alaninc but most probably has a similar mode of action as Bacilysin.

AmyCide™ is particularly unusual because it comprises a mixture of lipopeptides and antibiotic that form a complex and are associated with the cell wall. The inventors suspect that aggregation occurs by virtue of the copious exopolysaccharides that encase the vegetative cell in mucilage. This polysaccharide component also contains γ-PGA which is typically present in the mucilage of *B. amyloliquefaciens* (82).

Mucoid colonies and exopolysaccharide production are characteristic of many *Bacillus* strains (54) and probably assist biofilm formation. The inventors speculate that an additional role is in the entrapment of biosurfactants. The aggregation of biosurfactants must also improve the performance of these antibiotics since as shown here, as individual moieties, their activity is greatly reduced. The inventors observe that activity of these biosurfactants is greatly increased when combined. An intriguing question is how AmyCide™ lyses *C. difficile* since *C. difficile* carries a protective proteinaeceous S-layer that encases the cell (60). The S-layer coating may not provide a complete covering to the cell wall or, alternatively, the arrays of self-assembled S-layer proteins may be broken down or denatured by AmyCide™. Pores formed by ordered arrays of S-layer proteins are ~30 Å in diameter (61) so it is possible that AmyCidem could permeate this barrier.

CONCLUSIONS

Figure 9A:
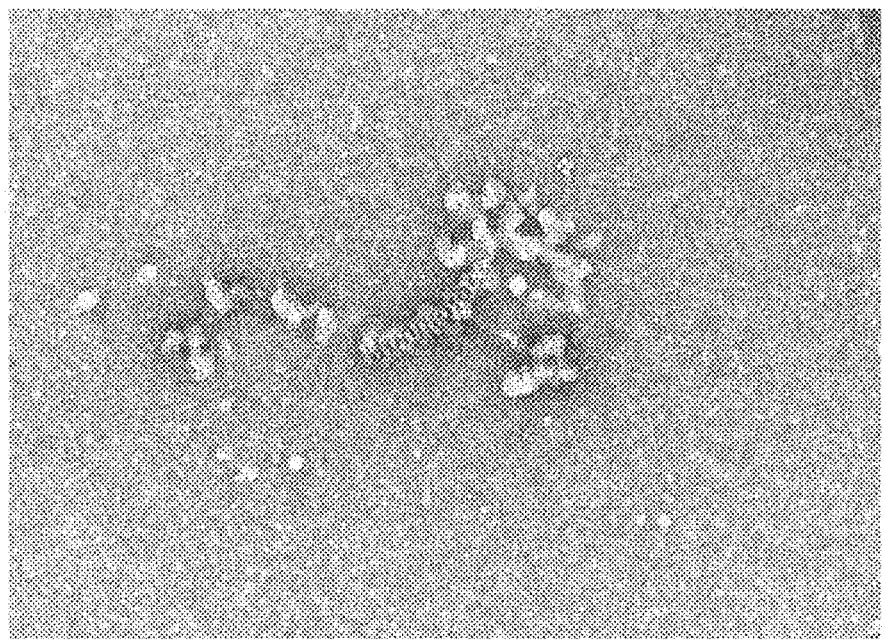
Figure 9B:
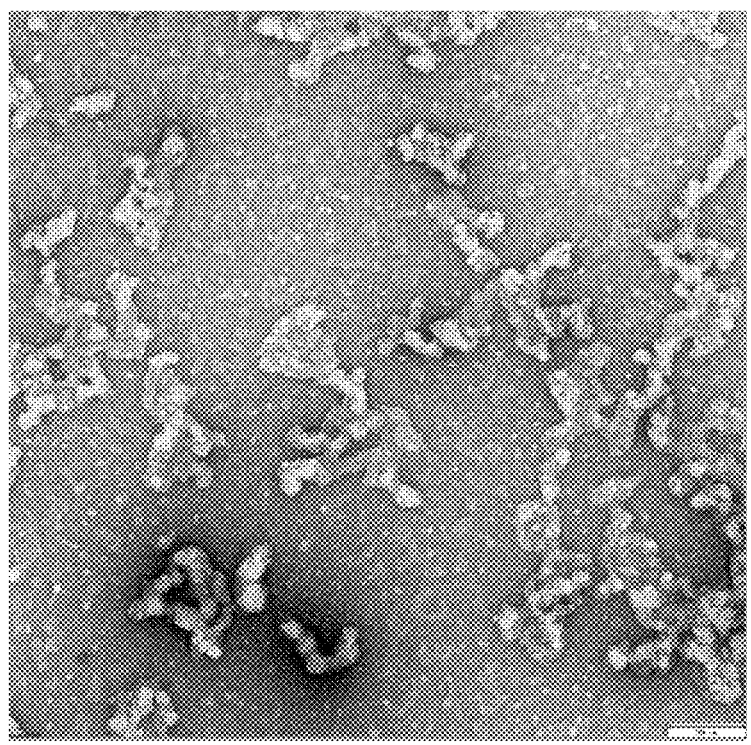

In conclusion, the inventors have shown that that *B. amyloliquefaciens* and *B. subtilis* strains carry surprising activity against *C. difficile*, which can be attributed to biosurfactants and Chlorotetataine and their ability to i) form micelles, ii) act synergistically and iii) concentrate or stabilise other antibiotics. These biosurfactants include different isoforms of surfactins, iturins, fengycins and potentially others (see FIGS. 10, 14 and 15 and Table 9). The inventors have shown that the precise isoforms may not matter since they differ somewhat between strains (see FIG. 14), whereas their stoichiometry and concentration may matter, and the more biosurfactants used or produced does appear to correlate with antibacterial activity (see FIG. 10B). The inventors were surprised to observe that higher concentrations of biosurfactants, whether homogenous or heterogenous mixtures, lead to the formation of micelles and possibly correspond to granular-like compounds present in the extracellular material (see FIG. 9). The biosurfactants are water and methanol soluble. For SG297 and SG277, which carry the most potent activity, surfactins, iturins, and fengycins have the greatest activity when coupled with Chlorotetaine. *B. licheniformis* strains that have anti-CD activity must produce some other molecule or mechanism but activity is probably not due to biosurfactants.

A role of extracellular polysaccharide in stabilising the complex must be considered since the highest levels of activity always correspond to the SEC fractions and individual components have the lower activities. C15 iturin A is a water-soluble lipopeptide that can form micelles (~7 nm diameter) and plays a role in solubilising other lipopeptides with the formation of mixed micelles (~3 nm diameter). The profile of SG297 is different, but the inventors assume the same concept applies.

The inventors assume that different strains produce different activities dependent upon the concentration of lipopeptides and micelles thus produced. To explain the *B. subtilis* strains that have lower activity, but no C15 iturin A, the inventors propose that there are other lipopeptides that play a role in solubilising lipopeptides, but C15 iturin is effective.

REFERENCES

1. Depeatel D D, Aronoff D M. 2013. Epidemiology of *Clostridium diffcile* infection. J Pharm Pract 26:464-475.
2. Gerding D N. 2004. Clindamycin, cephalosporins, fluoroquinolones, and *Clostridium diffcile*-associated diarrhea: this is an antimicrobial resistance problem. Clin Infect Dis 38:646-648.
3. Gough E, Shaikh H, Manges A R. 2011. Systematic review of intestinal microbiota transplantation (fecal bacteriotherapy) for recurrent *Clostridium difficile* infection. Cin Infect Dis 53:994-1002.
4. Khoruts A, Sadowsky M J. 2016. Understanding the mechanisms of faecal microbiota transplantation. Nat Rev Gastroenterol Hepatol 13:508-516.
5. Drekonja D, Reich J, Gezahegn S, Greer N, Shaukat A, MacDonald R, Rutka I, Wilt T J. 2015. Fecal Microbiota Transplantation for *Clostridium* dfficile Infection: A Systematic Review. Ann Intern Med 162:630-638.
6. Costello S P, Conlon M A, Vuaran M S, Roberts-Thomson I C, Andrews J M. 2015. Faecal micrbiota transplant for recurrent *Clostridium difficile* infection using long-term frozen stool is effective: clinical efficacy and bacterial viability data. Aliment PharmacolTher 42:1011-1018.
7. Ott S J, Waetzig G H, Rehman A, Moltzau-Anderson J, Bharti R, Grasis J A, Cassidy L, Tholey A, Fickenscher H, Seegert D, Rosenstiel P, Schreiber S. 2017. Efficacy of Sterile Fecal Filtrate Transfer for Treating Patients With *Clostridium* diicik Infection. Gastroenterology 152:799-811 e797.
8. Smits L P, Bouter K E, de Vos W M, Borody T J, Nieuwdorp M. 2013. Therapeutic potential of fecal microbiota transplantation. Gastroenterology 145:946-953.
9. Petrof E O, Khoruts A. 2014. From stool transplants to next-generation microbiota therapeutics. Gastroenterology 146:1573-1582.
10. Lawley T D, Clare S, Walker A W, Stares M D, Connor T R, Raisen C, Goulding D, Rad R, Schreiber F, Brandt C, Deakin L J, Pickard D J, Duncan S H, Flint H J, Clark T G, Parkhill J, Dougan G. 2012. Targeted restoration of the intestinal microbiota with a simple, defined bacteriotherapy resolves relapsing *Clostridium difficile* disease in mice. PLoS Pathog 8:e1002995.
11. Tvede M, Tinggaard M, Helms M. 2015. Rectal bacteriotherapy for recurrent *Clostridium difficile*-associated diarrhoea: results from a case series of 55 patients in Denmark 2000-2012. Clin Microbiol Infect 21:48-53.
12. Orenstein R, Dubberke E, Hardi R, Ray A, Mullane K, Pardi D S, Ramesh M S, Investigators P C. 2016. Safety and Durability of RBX2660 (Microbiota Suspension) for Recurrent *Clostridium diffcile* Infection: Results of the PUNCH C D Study. Clin Infect Dis 62:596-602.
13. Nielsen H B, Almelda M, Juncker A S, Rasmussen S, I3 J, Sunagawa S, Pliehta D R, Gautier L, Pedersen A G, L Chatelier E, Pelletier E, Bonde I, Nielsen T, Manichanh C, Arumugam M, Batto J M, Quintanilha Doe Santos M B, Blom N, Borruel N, Burgdorf K S, Boumezbeur F, Casellas F, Dore J, Dworzynsld P, Guarner F, Hansen T, Hildebrand F, Kans R S Kennedy S, Kristiansen K, Kultima J R, Leonard P, Levenez F, Lund O, Moumen B, L Paslier D, Pons N, Pedersen O, Prifti E, Qin J, Raes J, Sorensen S, Tap J, Tims S, Ussery D W, Yamada T, Meta H T C, Renault P, Sicheritz-Ponten T, Bork P, et al. 2014. Identification and assembly of genomes and genetic elements in complex metagenomic samples without using reference genomes. Nat Biotechnol 32:822-828.
14. Qin J, Li R, Raes J, Arumugam M, Burgdorf K S, Manichanh C, Nielsen T, Pons N, Lvenez F, Yamada T, Mende D R, I. J, Xu J, Li S, Li D, Cao J, Wang B, LIang H, Theng H, Xie Y, Tap J, Lepage P, Bertalan M, Batto J M, Hansen T, Le Paslier D, Inneberg A, Nielsen H B, Pelletier E, Renault P, Sicheritz-Ponten T, Turner K, Zhu H, Yu C, Li S, Jian M, Thou Y, L Y, Zhang X, Li S, QIn N, Yang H, Wang J, Brunak S, Dore J, Guarner F, Kristiansen K, Pedersen O, Parkhill J, Weissenbach J, et al. 2010. A human gut microbial gene catalogue established by metagenomic sequencing. Nature 464:59-65.
15. Browne H P, Forster S C, Anonye B O, Kumar N, Nevile B A, Stares M D, Goulding D, Lawley T D. 2016. Culturing of 'unculturable' human microbiota reveals novel taxa and extensive sporulation. Nature 533:543-546.
16. Lagier J C, Armougom F, Million M, Hugon P, Pagnier I, Robert C, Bittar F, Fournous G, Gimenez G, Maraninchi M, Trape J F, Koonin E V, La Scola B, Raoult D. 2012. Microbial culturomics: paradigm shift in the human gut microbiome study. Clin Microbiol Infect 18:1185-1193.
17. Lagier J C, Hugon P, Khelaifia S, Fournier P E, La Scola B, Raoult D. 2015. The rebirth of culture in microbiology through the example of culturomics to study human gut microbiota. Clin Microbiol Rev 28:237-264.
18. Fakhry S, Sorrentni I, Ricca E, De Felice M, Baccigalupi L. 2008. Characterization of spore forming Bacilli isolated from the human gastrointestinal tract. J Appl Microbiol 105:2178-2186.
19. Hong H A, Khaneia R, Tam N M. Cazzato A, Tan S, Urdaci M, Brisson A, Gasbarrini A, Barnes I, Cutting S M. 2009. *Bacillus subtilis* isolated from the human gastrointestinal tract. Res Microbiol 160:134-143.
20. Alou M T, Fournier P E, Raoult D. 2016. "Bacius mediterrneensis," a new bacterial species isolated from human gut microbiota. New Microbes New Infect 12:86-87.
21. Hong H A, To E, Fakhry S, Baccigalupi L, Ricca E, Cutting S M. 2009. Defining the natural habitat of Bacilius spore-formers. Res Microbiol 160:375-379.
22. Nicholson W L. 2002. Roles of *Bacillus* endospores in the environment. Cellular and Molecular We Sciences 59:410-416.
23. Casula G, Cutting S M. 2002. Bacilus probiotics: spore germination in the gastrointestinal tract. App Env Microbiol 68:2344-2352.
24. Tam N K, Uyen N Q, Hong H A, Duc le H, Hoa T F, Serra C R, Henriques A O, Cutting S M. 2006. The intestinal life cycle of *Bacillus subtilis* and close relatives. J Bacteriol 188:2692-2700.
25. Cartman S T, La Ragione R M, Woodward M J. 2008. Bacius *subtilis* spores germinate in the chicken gastrointestinal tract. Applied and environmental microbiology 74:5254-5258.
26. Ghelardi E, Celandroni F, Salvetti S, Gueye S A, Lupetti A, Senesi S. 2015. Survival and persistence of *Bacillus clausii* in the human gastrointestinal tract following oral administration as spore-based probiotic formulation. J Appl Microbiol 119:552-559.
27. Nakano M M, Zuber P. 1998. Anaerobic growth of a "strict aerobe" (Bacilus subtils). Annual Review of Microbiology 52:165-190.
28. Marteyn B, Scorza F B, Sansonetti P J, Tang C. 2011. Breathing life into pathogens: the influence of oxygen on bacterial virulence and host responses in the gastrointestinal tract. Cell Microbiol 13:171-176.
29. Hong H A, Duc le H, Cutting S M. 2005. The use of bacterial spore formers as probiotics. FEMS Microbiol Rev 29:813-835.
30. Iflnskaya O N, Ulyanova V V, Yarullina D R, Gataulln I G. 2017. Secretome of Intestinal Bacilli: A Natural Guard against Pathologies. Front Microbiol 8:1666.
31. Zhao X, Kuipers O P. 2016. Identification and classification of known and putative antimicrobial compounds produced by a wide variety of *Bacillales* species. BMC Genomics 17.882.
32. Abrionel H, Franz C M, Ben Omar N, Galvez A. 2011. Diversity and applications of *Bacillus* bacteriocins. FEMS Microbiol Rev 35:201-232.
33. Stein T. 2005. *Bacillus subtilis* antibiotics: structures, syntheses and specific functions. Mol Microbiol 56:845-857.
34. Ayed H B, Maali H, Hmidet N, Nasri M. 2015. Isolation and biochemical characterisation of a bacteriocin-like substance produced by *Bacillus amyloliquefaciens* An6. J Glob Antimicrob Resist 3:255-261.

35. Colenutt C, Cutting S M. 2014. Use of Bacius *subtilis* PXN21 spores for suppression of *Clostridium* dfcile infection symptoms in a murine model. FEMS Microbiol Lett 358:154-161.
36. Permpoonpattana P, Hong H A, Phetcharaburanin J, Huang J M, Cook J, Fairweather N F, Cutting S M. 2011. Immunization with *Bacillus* spores expressing toxin A peptide repeats protects against infection with *Clostridium difficile* strains producing toxins A and B. Infection and immunity 79:2295-2302.
37. Hong H A, Hitri K, Hosseni S, Kotowicz N, Bryan D, Mawas F, Wilkinson A J, van Broekhoven A, Kearsey J, Cutting S M. 2017. Mucosal Antibodies to the C Terminus of Toxin A Prevent Colonization of *Clostridium difficile*. Infect Immun 85.
38. Geeraerts S, Ducatelle R, Haesebrouck F, Van Immerseel F. 2015. *Bacillus amyloliquefaciens* as prophylactic treatment for *Clostridium* diifci-associated disease in a mouse model. J Gastroenterol Hepatol 30:1275-1280.
39. GuS, Chen D, Zhang J N, Lv X, Wang K, Duan L P, Nie Y, Wu X L. 2013. Bacterial community mapping of the mouse gastrointestinal tract. PLoS One 8:e74957.
40. Chun J, Bae K S. 2000. Phylogenetic analysis of *Bacillus subtilis* and related taxa based on partial gyrA gene sequences. Antonie Van Leeuwenhoek 78:123-127.
41. O'Toole G, Kaplan H B, Kolter R. 2000. Biofilm formation as microbial development. Annu Rev Microbial 54:49-79.
42. Hong H A, Ferreira W T, Hosseni S, Anwar S, Hitri K, Wilkinson A J, Vabjen W, Zentek J, Soloviev M, Cutting S M. 2017. The Spore Coat Protein CotE Facilitates Host Colonisation by *Clostridium difficile*. J Infect Dis doi: 10.1093/infdis/jix488.
43. Sambol S P, Tang J K, Merrigan M M, Johnson S, Gerding D N. 2001. Infection of hamsters with epidemiologically important strains of Costridium *difficile*. J Infect Dis 183:760-1766.
44. Ma Z, Wang N, Hu J, Wang S. 2012. Isolation and characterization of a new iturinic lipopeptide, mojavensin A produced by a marine-derived bacterium *Bacillus mojavensis* B062A. J Antibiot (Tokyo) 65:317-322.
45. Bechet M, Caradec T, Hussein W, Abderrahmani A, Chollet M, Leclere V, Dubois T, Lereclus D, Pupin M, Jacques P. 2012. Structure, biosynthesis, and properties of kurstakins, nonribosomal lipopeptides from *Bacillus* spp. Appl Microbiol Biotechnol 95:593-600.
46. Meena K R, Kanwar S S. 2015. Lipopeptides as the antifungal and antibacterial agents: applications in food safety and therapeutics. Biomed Res Int 2015:473050.
47. Duitman E H, Hamoen L W, Rembold M, Venema G, Seitz H, Saenger W, Bernhard F, Reinhardt R, Schmidt M, Ullrich C, Stein T, Leenders F, Vater J. 1999. The mycosubtilin synthetase of *Bacillus subtilis* ATCC6633: a multifunctional hybrid between a peptide synthetase, an amino transferase, and a fatty acid synthase. Proc Natl Acad Sci USA 96:13294-13299.
48. Razafindralambo H, Popineau Y, Deleu M, Hbid C, Jaques P, Thonart P, Paquot M. 1997. Surface-active properties of surfactin/Iturin A mixtures produced by *Bacillus subtilis*. Langmuir 13:6026.
49. Cui X, Mao S, Liu M, Yuan H, Du Y. 2008. Mechanism of surfactantmicelle formation. Langmuir 24:1077105.
50. Makovtzld A, Baram J, Shai Y. 2008. Antimicrobial lipopolypeptides composed of palmitoyl Di- and tricationic peptides: in vitro and in vivo activities, self-assembly to nanostructures, and a plausible mode of action. Biochemistry 47:10630-10636.
51. Horn J N, Romo T D, Grossfield A. 2013. Simulating the mechanism of antimicrobial lipopeptides with all-atom molecular dynamics. Biochemistry 52:5604-5610.
52. Horn J N, Sengillo J D, in D, Romo T D, Grossleld A. 2012. Characterization of a potent antimicrobial lipopeptide via coarse-grained molecular dynamics. Biochim Biophys Acta 1818:212-218.
53. Popiolskd™, Otsuka I, H-aI S, Muniz E C, Soldi V, Borsali R. 2016. Preparation of Polymeric Micelles of Poly(Ethylene Oxide-b-Lactic Acid) and their Encapsulation with Lavender Oil. Materials Research 19:1356-1365.
54. Malick A, Khodae N, Benkerroum N, Karboune S. 2017. Production of exopolysaccharides by selected *Bacillus* strains: Optimization of media composition to maximize the yield and structural characterization. Int J Biol Macromol 102:539-549.
55. Le N R, Go T H, Ie S M, Jeong S Y, Park G T, Hong C O, Son H J. 2014. In vitro evaluation of new functional properties of poly-gamma-glutamic acid produced by *Bacillus subtilis* D7. Saudi J Biol Sci 21:153-158.
56. Inbaraj B S, Kao T H, Tsai T Y, Chiu C P, Kumar R, Chen B H. 2011. The synthesis and characterization of poly (gamma-glutamic acid)-coated magnetite nanoparticles and their effects on antibacterial activity and cytotoxicity. Nanotechnology a:075101.
57. Orsod M, Joseph M, Huyop F. 2012. Characterization of Exopolysaccharides produced by *Bacillus ereus* and *Brachybacterium* sp. isolated from Asian sea bass (*Lates calcarifer*). Malaysian Journal of Microbiology 8:170.
58. Isa M H M, Coragia D E, Frazier R A, Jauregi P. 2007. Recovery and purification of surfactin from fermentation broth by a two-step ultrafiltration process. Journal of Membrane Science 296:51-57.
59. Jauregi P, Coutte F, Catiau L, Lecouturier D, Jacques P. 2013. Micelle size characterization of lipopeptides produced by *B. subtilis* and their recovery by the two-step ultrafiltration process. Separation and Purification Technology 104:175-182.
60. Fagan R P, Fairweather N F. 2014. Biogenesis and functions of bacterial S-layers. Nat Rev Microbiol 12:211-222.
61. Baranova E, Fronzes R, Garcia-Pino A, Van Gerven N, Papapostolou D, Pehau-Arnaudet G, Pardon E, Steyaert J, Howorka S, Remaut H. 2012. SbsB structure and lattice reconstruction unveil Ca2+ triggered S-layer assembly. Nature 487:119-122.
62. Lessa F C, Mu Y, Bamberg W M, Beldavs Z G, Dumyati G K, Dunn J R Farley M M, Horbauer S M, Meek J I, Phipps E C, Wilson L E, Winston L G, Cohen J A, Limbago B M, Fridkin S K, Gerding D N, McDonald L C. 2015. Burden of *Clostridium difficile* infection in the United States. N Engl J Med 372:825-834.
63. Bauer M P, Notermans D W, van Benthem B H, Brazier J S, Wilcox M H, Rupnik M, Monnet D L, van Dissel J T, KuUper E J. 2011. *Clostridium* dcile infection in Europe: a hospital-based survey. Lancet 377:63-73.
64. Kely D, King T, Aminov R. 2007. Importance of microbial colonization of the gut in early life to the development of immunity. Mutat Res 622:58-69.
65. Ege M J, Mayer M, Normand A C, Genuneit J, Cookson W O, Braun-Fahrlander C, Heederik D, Plarroux R, von Mutius E, Group GTS. 2011. Exposure to environmental microorganisms and childhood asthma. N Engl J Med 364:701-709.
66. Lopez-Serrano P, Perez-Cae J L, Perez-Fernandez M T, Fernandez-Font J M, Boixeda de Miguel D, Fernandez- 66. Rodriguez C M. 2010. Environmental risk factors in inflammatory bowel diseases. Investigating the hygiene hypothesis: a Spanish case-control study. Scand J Gastroenterol 45:1464-1471.
67. Strachan D P. 1989. Hay fever, hygiene, and household size. BMJ 99:1259-1260.
68. Lessa F C, Gould C V, McDonald L C. 2012. Current status of *Clostridium difficile* infection epidemiology. Clin Infect Dis 55 Suppl 2:S65-70.
69. Gupta A, Khanna S. 2014. Community-acquired *Clostridium difficile* infection: an increasing public health threat. Infect Drug Resist 7.63-72.
70. Bloomfield S F, Rook G A, Scott E A, Shanahan F, Stanwell-Smith R, Turner P. 2016. Time to abandon the hygiene hypothesis: new perspectives on allergic disease, the human microbiome, infectious disease prevention and the role of targeted hygiene. Perspect Public Health 136:213-224.
71. Ayukekbong J A, Ntemgwa M, Atabe A N. 2017. The threat of antimicrobial resistance in developing countries: causes and control strategies. Antimicrob Resist Infect Control 6:47.
72. Burke K E, Lamont J T. 2014. Costridium dfcile infection: a worldwide disease. Gut Liver 8:1-6.
73. Collins D A, Hawkey P M, Riley T V. 2013. Epidemiology of *Clostridium difficile* infection in Asia. Antimicrob Resist Infect Control 2:21.
74. Vater J. 1986. Upopetides, an attractive class of microbial surfactants. Prog Colloid Polym Sci 72:12-18.
75. Mnif I, Ghribi D. 2015. Review lipopeptides biosurfactants: Mean classes and new insights for industrial, biomedical, and environmental applications. Biopolymers 104:129-147.
76. Zhi Y, Wu Q, Xu Y. 2017. Genome and transcriptome analysis of surfactin biosynthesis in *Bacillus amyloliquefaciens* MT45. Sci Rep 7:40976.
77. Xu Z, Shao J, Li B, Yan X, Shen Q, Zhang R. 2013. Contribution of bacillomycin D in *Bacillus amyloliquefaciens* SQR9 to antifungal activity and biofilm formation. Appl Environ Microbiol 79:808-85.
78. Deleu M, Paquot M, Nylander T. 2008. Effect of fengycin, a lipopeptide produced by *Bacillus subtilis*, on model biomembranes. Biophys J 94:2667-2679.
79. Kim P I, Bai H, Bai D, Chae H, Chung S, Kim Y, Park R, Chi Y T. 2004. Purification and characterization of a lipopeptide produced by *Bacillus thuringiensis* CMB26. J Appl Microbiol 97.942-949.
80. Klich M A, Arthur K S, Lax A R, Bland J M. 1994. Iturin A: a potential new fungicide for stored grains. Mycopathologia 127:123-127.
81. Yoshida 5, Hiradate S, Tsukamoto T, Hatakeda K, Shirata A. 2001. Antimicrobial Activity of Culture Filtrate of *Bacillus amyloliquefaciens* RC-2 Isolated from Mulberry leaves. Phytopathology 91:181-187.
82. LIu J, He D, Li X Z, Gao S, Wu H, Lu W, Gao X, Zhou T. 2010. Gamma-polyglutamic acid (g-PGA) produced by *Bacillus amyloliquefaciens* Co6 promoting its colonization on fruit surface. Int J Food Microbiol 142:190-197.
83. Smith C J, Markowitz S M, Macrina F L. 1981. Transferable tetracycline resistance in *Clostridium difficile*. Antimicrob Agents Chemother 19:997-1003.
84. Wust J, Sullivan N M, Hardegger U, Wilkins T D. 1982. Investigation of an outbreak of antibiotic-associated colitis by various typing methods. Journal of clinical microbiology 16:1096-110.
85. Phetcharaburanin J, Hong H A, Colenutt C, Bianconi I, Sempere L, Permpoonpattana P, Smith K, Dembek M, Tan S, Brisson M C, Brison A R, Fairweather N F, Cutting S M. 2014. The spore-associated protein BclA1 affects the susceptibility of animals to colonization and infection by *Clostridium difficile*. Mol Microbiol 92:1025-1038.
86. Nicholson W L, Setlow P. 1990. Sporulation, germination and outgrowth., p 391-450. In Harwood. C R, Cutting. S M (ed), Molecular Biological Methods for *Bacillus*. John Wiley & Sons Ltd., Chichester, U K.
87. Lau J T, Whelan F J, Herath I, LIe C H, Collins S M, Bereik P, Surette M G. 2016. Capturing the diversity of the human gut microbiota through culture-enriched molecular profiling. Genome Med 8:72.
88. Youseef N H, Duncan K E, Nagle D P, Savage K N, Knapp R M, McInerney M J. 2004. Comparison of methods to detect biosurfactant production by diverse microorganisms. J Microbiol Methods 56:339-347.
89. CISI. 2010. Methods for antimicrobial dilution and disk susceptibility testing of infrequently isolated or fastidious bacteria; approved guideline—Second Ed M45-A2. Institute CaLS, USA.
90. EFSA. 2012. Guidance on the assessment of bacterial susceptibility to antimicrobials of human and veterinary importance. EFSA Journal 10:2740.

The invention claimed is:

1. An antibiotic composition comprising precipitated micelles comprising: (i) an antibiotic, wherein the antibiotic is Chlorotetaine, and (ii) a lipopeptide selected from the group consisting of a member of the Surfactin family, a member of the Iturin family and a member of the Fengycin family, wherein the lipopeptide facilitates the formation of micelles, and wherein the micelle incorporates or absorbs the antibiotic.

2. An antibiotic composition according to claim 1, wherein each micelle has an average diameter of between 1 nm and 500 nm, or between 1 nm and 300 nm, or between 1 nm and 160 nm, or between 3 nm and 160 nm.

3. An antibiotic composition according to claim 1, wherein the composition further comprises a glycolipid, and wherein the glycolipid is a Rhamnolipid and/or a Sophorolipd.

4. An antibiotic composition according to claim 3, wherein the glycolipid is a Rhamnolipid, and the Rhamnolipid is a Mono or Di Rhamnolipid.

5. A composition according to claim 1, wherein the composition comprises a member of the Surfactin family; and further comprises a Rhamnolipid and/or a Sophorolipid; and/or (ii) Difficidin or Oxydifficidin.

6. An antibiotic composition according to claim 1, wherein the composition further comprises Di-O-acetate lactone, and/or: a further lipopeptide selected from a group consisting of: Mycosubtilin; Mojavensin A; and Kurstakin.

7. A composition according to claim 1, wherein the lipopeptide is a member of the Iturin family, and a member of the Surfactin family.

8. A composition according to claim 1, wherein the member of the Iturin Family is selected from a group consisting of: Iturin A [SEQ ID NO:1], Iturin AL [SEQ ID NO: 2], Iturin C [SEQ ID NO:3], Mycosubtilin [SEQ ID NO:4], Bacillomycin D [SEQ ID NO:5], Bacillomycin F [SEQ ID NO:6], Bacillomycin L [SEQ ID NO:7], Bacillomycin LC [SEQ ID NO:8] and Bacillopeptin A, B or C [SEQ ID NO: 17].

9. A composition according to claim 1, wherein the member of the Iturin family is Iturin A [SEQ ID NO:1].

10. A composition according to claim 1, wherein the member of the Surfactin family is selected from a group consisting of: Esperin [SEQ ID NO: 9], Lichenysin [SEQ ID NO: 10], Pumilacidin [SEQ ID NO: 11] and Surfactin [SEQ ID NO: 12].

11. A composition according to claim 1, wherein the antibiotic composition comprises the $C_{15}$ isoform of Iturin A, and the $C_{15}$ isoform of Surfactin.

12. A dietary supplement or foodstuff comprising the antibiotic composition according to claim 1.

13. A method of treating, preventing or ameliorating a bacterial infection, the method comprising administering or having administered, to a subject in need of such treatment, a therapeutically effective amount of the antibiotic composition according to claim 1.

14. A method according claim 13, wherein the bacterial infection which is treated, prevented or ameliorated is a Gram-positive bacterial infection, and wherein the Gram-positive bacteria is a member of the phylum Firmicutes.

15. A method according to claim 13, wherein the bacterium is *Clostridium* spp.

16. A method according to claim 13, wherein the bacterium is *Staphylococcus* spp.

17. A method according to claim 13, wherein the bacterial infection which is treated, prevented or ameliorated is a Gram-negative bacterial infection, and wherein the Gram-negative bacteria is an Enterobaceriaceae.

18. A method according to claim 13, where in the bacterium is *Vibrio* spp.

19. A method according to claim 13, wherein the bacterial infection which is treated, prevented or ameliorated is a *Mycobacterium* spp., infection.

20. A method of treating, preventing or ameliorating a *C. difficile* infection, the method comprising administering or having administered to a subject in need of such treatment, a therapeutically effective amount of an antibiotic composition according to claim 1.

21. A precipitated micelle comprising a lipopeptide, wherein the micelle has incorporated or absorbed an antibiotic, wherein the antibiotic is chlorotetaine.

22. The antibiotic composition of claim 1, wherein the antibiotic composition is lyophilized.

23. The antibiotic composition of claim 1, wherein the precipitated micelles are lyophilized.

24. A method according to claim 14, wherein the Gram-positive bacteria are selected from the group consisting of *Clostridium* spp., *Bacillus* spp., *Listeria* spp., *Mycobacterium* spp., *Lactobacillus, Staphylococcus* spp., *Streptococcus* spp. and *Enterococcus* spp.

25. A method according to claim 17, wherein the Gram-negative bacteria are selected from the group consisting of *Salmonella* spp., *Escherichia* spp., *Campylobacter* spp., *Pseudomonas* spp. and *Vibrio* spp.

26. A method according to claim 15, wherein the *Clostridium* spp. is *C. difficile*.

27. A method according to claim 16, wherein the *Staphylococcus* spp. is *S. aureus*.

28. A method according to claim 18, wherein the *Vibrio* spp. is selected from the group consisting of *V. harveyi* or and *V. parahaemolyticus*.

29. A method according to claim 19, wherein the *Mycobacterium* spp. is selected from the group consisting of *Mycobacterium tuberculosis* and *Mycobacterium leprae*.

30. A composition of claim 10, wherein the surfactin is selected from the group consisting of the $C_{12}$, $C_{13}$, $C_{14}$, $C_{15}$, $C_{16}$, and $C_{17}$ isoform.

31. A composition of claim 9, wherein the Iturin A is selected from the group consisting of the $C_{14}$, $C_{15}$ and $C_{16}$ isoforms.

32. A composition according to claim 4, wherein the Rhamnolipid is selected from the group consisting of the $C_8$, $C_{8:2}$, $C_{10}$, $C_{12}$, $C_{12:2}$, $C_{14}$ and $C_{14:2}$ isoform.

33. A composition according to claim 7, wherein the member of the Iturin family and a member of the Surfactin family are used in a ratio of between 1:10 and 10:1, or between 1:5 and 5:1, or between 1:3 and 3:1, or between 1:2 and 2:1.

34. A composition according to claim 6, wherein the Mycosubtilin is the $C_{17}$ isoform.

35. A composition according to claim 6, wherein the Mojavensin A is the $C_{16}$ isoform.

36. A composition according to claim 6, wherein the Kurstakin is selected from the group consisting of the $C_{13}$ and the $C_{15}$ isoform.

* * * * *

UNITED STATES PATENT AND TRADEMARK OFFICE
CERTIFICATE OF CORRECTION

| | | |
|---|---|---|
| PATENT NO. | : 12,171,734 B2 | Page 1 of 1 |
| APPLICATION NO. | : 16/970708 | |
| DATED | : December 24, 2024 | |
| INVENTOR(S) | : Cutting et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 289 days.

Signed and Sealed this
Eighth Day of July, 2025

Coke Morgan Stewart
*Acting Director of the United States Patent and Trademark Office*